(12) United States Patent
Hirano et al.

(10) Patent No.: US 6,956,050 B2
(45) Date of Patent: Oct. 18, 2005

(54) IMIDAZOLE COMPOUNDS AS ANTI-INFLAMMATORY AND ANALGESIC AGENTS

(75) Inventors: Misato Hirano, Aichi (JP); Satoru Iguchi, Aichi (JP); Kazunari Nakao, Aichi (JP); Tatsuya Yamagishi, Aichi (JP)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/409,836

(22) Filed: Apr. 9, 2003

(65) Prior Publication Data

US 2003/0220372 A1 Nov. 27, 2003

Related U.S. Application Data

(60) Provisional application No. 60/372,346, filed on Apr. 12, 2002.

(51) Int. Cl.[7] ............... A61K 31/4164; A61K 31/4178; C07D 233/64
(52) U.S. Cl. ............. 514/396; 514/341; 514/365; 514/393; 546/275.1; 546/274.1; 548/331.5; 548/343.5; 548/202; 548/302.7
(58) Field of Search ............. 548/331.5, 343.5, 548/202, 302.7; 546/275.1, 274.1; 514/341, 365, 393, 396

(56) References Cited

FOREIGN PATENT DOCUMENTS

| EP | 1 122 243 A1 | 10/1999 |
|---|---|---|
| WO | WO 97/22341 | 6/1997 |
| WO | WO-9722341 A1 * | 6/1997 |
| WO | WO 99/47497 | 9/1999 |
| WO | WO 00/64888 | 11/2000 |
| WO | WO 02/32422 | 4/2002 |

* cited by examiner

Primary Examiner—Laura L. Stockton
(74) Attorney, Agent, or Firm—Suzanne M. Harvey; David R. Kurlandsky; Charles W. Ashbrook

(57) ABSTRACT

This invention provides a compound of the formula (I):

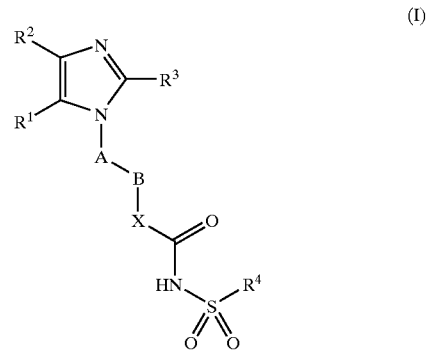

wherein:
$R^1$ represents a hydrogen atom, an alkyl group, etc.; $R^2$ represents a hydrogen atom, a halogen atom, etc.; $R^3$ represents a hydrogen atom, an alkyl group, etc.; $R^4$ represents an aryl group, etc.; A represents an aryl[1], etc; B represents an alkylene etc.; X represents NH, etc.;
or a pharmaceutically acceptable ester of such compound, and pharmaceutically acceptable salts thereof.

These compounds are useful for the treatment of medical conditions mediated by prostaglamndin such as pain, fever or inflammation, etc. This invention also provides a pharmaceutical composition comprising the above compound.

14 Claims, No Drawings

IMIDAZOLE COMPOUNDS AS ANTI-INFLAMMATORY AND ANALGESIC AGENTS

This application claims the benefit of U.S. Provisional Application No. 60/372,346 filed Apr. 12, 2002.

TECHNICAL FIELD

This invention relates to imidazole compounds, and their pharmaceutically acceptable salts, pharmaceutical compositions containing them, and their medical uses. The compounds of this invention have activity as prostaglandin $E_2$ receptor antagonists, and these are useful in the treatment or alleviation of pain and inflammation and other inflammation-associated disorders, such as arthritis, and in treating or preventing disorders or medical conditions selected from pain, inflammatory diseases and the like.

BACKGROUND ART

Prostaglandins are mediators of pain, fever and other symptoms associated with inflammation. Prostaglandin $E_2$ ($PGE_2$) is the predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis or the like.

Four $PGE_2$ receptor subtypes ($EP_1$, $EP_2$, $EP_3$ and $EP_4$) displaying different pharmacological properties have been cloned. The $EP_4$ subtype, a Gs-coupled receptor, stimulates cAMP production, and is distributed in a wide variety of tissue suggesting a major role in $PGE_2$-mediated biological events.

WO99/47497 discloses carboxylic acids and acylsulfonamides compounds as prostaglandin-receptor antagonists. Although heteroaryl compounds synthesized are described in WO00/64888, it relates to peroxisome proliferataor-activated receptors(PPAR) ligands.

The invention addresses the problem of providing $EP_4$ receptor modulators (e.g., agonists and antagonists) which have improved $EP_4$ receptor modulating activities (e.g., angonist or antagonist activities).

BRIEF DISCLOSURE OF THE INVENTION

The present invention provides a compound of the following formula (I):

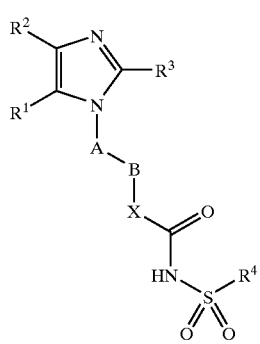

(I)

wherein:
either $R^1$ represents a hydrogen atom, an alkyl group having from 1 to 6 carbon atoms, an aryl group or a heteroaryl group; and $R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group; or $R^1$ and $R^2$ groups are joined together to form an alkylene chain having 3 to 6 carbon atoms;

$R^3$ represents a hydrogen atom, a halogen atom, an alkyl group having from 1 to 6 carbon atoms, an amino group, mono- or di-alkylamino groups, with alkyl group(s) having from 1 to 6 carbon atoms, a haloalkyl group having from 1 to 6 carbon atoms, a cycloalkyl group having from 3 to 8 carbon atoms, a cycloalkenyl group having from 3 to 10 carbon atoms, an aralkyl group, an aryl group or a heteroaryl group;

$R^4$ represents an aryl group, or a heteroaryl group;

A represents an aryl[1] group having from 6 to 10 carbon atoms or an heteroaryl[1] group having from 5 to 7 atoms, wherein 1 to 4 of said atoms of the heteroaryl[1] group are independently selected from the group consisting of sulfur atoms, oxygen atoms and nitrogen atoms;

B represents an alkylene group having from 1 to 6 carbon atoms;

X represents NH, N[$(C_1-C_6)$alkyl], oxygen or sulfur;

said aryl groups have from 6 to 14 carbon atoms;

said heteroaryl groups are 5- to 14-membered aromatic heterocyclic groups containing from 1 to 4 heteroatoms selected from the group consisting of sulfur atoms, oxygen atoms and nitrogen atoms;

said aryl groups and said heteroaryl groups are unsubstituted or are substituted by at least one substituent selected from the group consisting of substituents α, defined below;

said aralkyl groups are alkyl groups having from 1 to 6 carbon atoms and which are substituted by at least one aryl group as defined above;

said substituents α are selected from the group consisting of alkyl group having from 1 to 6 carbon atoms, an aryl group defined above, a heteroaryl group defined above, hydroxy groups, halogen atom, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group, with alkyl group(s) having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, with alkyl group(s) having from 1 to 6 carbon atoms in the alkyl and alkoxy part, alkylsulfonylamino group having from 1 to 6 carbon atoms and aminosulfonyl group;

with the proviso that said aryl groups and said heteroaryl groups in said substituents α are not substituted by an aryl group or an heteroaryl group: or a pharmaceutically acceptable ester of such compound, or a pharmaceutically acceptable salt thereof.

The imidazole compounds of this invention have an antagonistic action towards prostaglandin and are thus useful in therapeutics, particularly for the treatment of a disorder or condition selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures or bone fracture, immune and autoimmune diseases such as systemic lupus erythematosus; AIDS(acquired immuno deficiency syndrome), gastrointestinal cancers such as colon cancer ; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease;

thrombosis; occlusive vascular disease; presurgery; and anti-coagulation, or the like in mammalian, especially humans.

The present invention provides a pharmaceutical composition for the treatment of a disorder or condition mediated by prostaglandin, in a mammal including a human, which comprises a compound of formula (I);

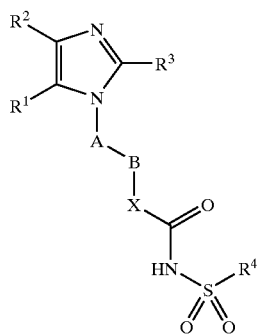

(I)

wherein:
either $R^1$ represents a hydrogen atom, an alkyl group having from 1 to 6 carbon atoms, an aryl group or a heteroaryl group; and
$R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group; or $R^1$ and $R^2$ groups are joined together to form an alkylene chain having 3 to 6 carbon atoms;
$R^3$ represents a hydrogen atom, a halogen atom, an alkyl group having from 1 to 6 carbon atoms, an amino group, mono- or di-alkylamino groups, with alkyl group(s) having from 1 to 6 carbon atoms, a haloalkyl group having from 1 to 6 carbon atoms, a cycloalkyl group having from 3 to 8 carbon atoms, a cycloalkenyl group having from 3 to 10 carbon atoms, an aralkyl group, an aryl group or a heteroaryl group;
$R^4$ represents an aryl group, or a heteroaryl group;
A represents an aryl[1] group having from 6 to 10 carbon atoms or an heteroaryl[1] group having from 5 to 7 atoms, wherein 1 to 4 of said atoms of one heteroaryl[1] group are independently selected from the group consisting of sulfur atoms, oxygen atoms and nitrogen atoms;
B represents an alkylene group having from 1 to 6 carbon atoms;
X represents NH, N[$(C_1-C_6)$alkyl], oxygen or sulfur;
said aryl groups have from 6 to 14 carbon atoms;
said heteroaryl groups are 5- to 14-membered aromatic heterocyclic groups containing from 1 to 4 heteroatoms selected from the group consisting of sulfur atoms, oxygen atoms and nitrogen atoms;
said aryl groups and said heteroaryl groups are unsubstituted or are substituted by at least one substituent selected from the group consisting of substituents α, defined below;
said aralkyl groups are alkyl groups having from 1 to 6 carbon atoms and which are substituted by at least one aryl group as defined above;
said substituents α are selected from the group consisting of alkyl group having from 1 to 6 carbon atoms, an aryl group defined above, a heteroaryl group defined above, hydroxy groups, halogen atom, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group having from 1 to 6 carbon atoms in the alkyl and alkoxy part, alkylsulfonylamino group having from 1 to 6 carbon atoms and aminosulfonyl group;
with the proviso that said aryl groups and said heteroaryl groups in said substituents α are not substituted by an aryl group or an heteroaryl group: and a pharmaceutically acceptable diluent or carrier.

Further, the present invention also provides a pharmaceutical composition for the treatment of a disorder or condition selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing sspondylitis, bursitis, burns including radiation and corrosive chemical injuries, sunburns, pain following surgical and dental procedures, bone fracture, immune and autoimmune diseases such as systemic lupus erythematosus; AIDS(acquired immuno deficiency syndrome), gastrointestinal cancers such as colon cancer; cellular neoplastic transformations or metastic tumor growth; Diabetic retinopathy, tumor angiogenesis; prostanoid-induced smooth muscle contraction associated with dysmenorrhea, premature labor, allergic rhinitis, atopic dermatitis, asthma or eosinophil related disorders, Hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease;

thrombosis; occlusive vascular disease; presurgery; and anti-coagulation, or the like, which comprises a therapeutically effective amount of the aryl or heteroaryl fused imidazole compound of formula (I) or its pharmaceutically acceptable salt together with a pharmaceutically acceptable diluent or carrier.

Also, the present invention provides a method for the treatment of a disorder or condition mediated by prostaglandin, in a mammalian including a human, which comprises administering to said subject a therapeutically effective amount of a compound of formula (I);

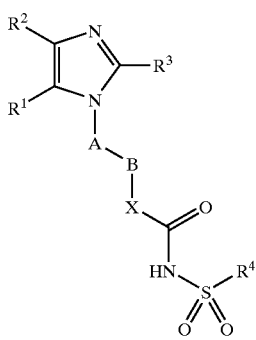

(I)

wherein:
either $R^1$ represents a hydrogen atom, an alkyl group having from 1 to 6 carbon atoms, an aryl group or a heteroaryl group; and
$R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group; or $R^1$ and $R^2$ groups are joined together to form an alkylene chain having 3 to 6 carbon atoms;
$R^3$ represents a hydrogen atom, a halogen atom, an alkyl group having from 1 to 6 carbon atoms, an amino group, mono- or di-alkylamino groups, with alkyl group(s) having from 1 to 6 carbon atoms, a haloalkyl group having from 1 to 6 carbon atoms, a cycloalkyl group having from 3 to 8 carbon atoms, a cycloalkenyl group having from 3 to 10 carbon atoms, an aralkyl group, an aryl group or a heteroaryl group;
$R^4$ represents an aryl group, or a heteroaryl group;
A represents an aryl$^1$ group having from 6 to 10 carbon atoms or an heteroaryl$^1$ group having from 5 to 7 atoms, wherein 1 to 4 of said atoms of one heteroaryl$^1$ group are independently selected from the group consisting of sulfur atoms, oxygen atoms and nitrogen atoms;
B represents an alkylene group having from 1 to 6 carbon atoms;
X represents NH, N[($C_1$–$C_6$)alkyl], oxygen or sulfur;
said aryl groups have from 6 to 14 carbon atoms;
said heteroaryl groups are 5- to 14-membered aromatic heterocyclic groups containing from 1 to 4 heteroatoms selected from the group consisting of sulfur atoms, oxygen atoms and nitrogen atoms;

said aryl groups and said heteroaryl groups are unsubstituted or are substituted by at least one substituent selected from the group consisting of substituents α, defined below;
said aralkyl groups are alkyl groups having from 1 to 6 carbon atoms and which are substituted by at least one aryl group as defined above;
said substituents α are selected from the group consisting of alkyl group having from 1 to 6 carbon atoms, an aryl group defined above, a heteroaryl group defined above, hydroxy groups, halogen atom, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group having from 1 to 6 carbon atoms in the alkyl and alkoxy part, alkylsulfonylamino group having from 1 to 6 carbon atoms and aminosulfonyl group;
with the proviso that said aryl groups and said heteroaryl groups in said substituents α are not substituted by an aryl group or an heteroaryl group: or a pharmaceutically acceptable ester of such compound, or a pharmaceutically acceptable salt thereof.

Further, the present invention provides a method for the treatment of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing sspondylitis, bursitis, burns including radiation and corrosive chemical injuries, sunburns, pain following surgical and dental procedures, bone fracture, immune and autoimmune diseases such as systemic lupus erythematosus; AIDS, gastrointestinal cancers such as colon cancer; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease; thrombosis; occlusive vascular disease;

presurgery; and anti-coagulation or the like, in a mammalian subject, which comprises administering to said subject a therapeutically effective amount of a compound of formula (I);

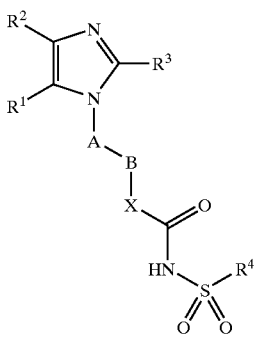

(I)

wherein:
either R¹ represents a hydrogen atom, an alkyl group having from 1 to 6 carbon atoms, an aryl group or a heteroaryl group; and
R² represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group; or R¹ and R² groups are joined together to form an alkylene chain having 3 to 6 carbon atoms;
R³ represents a hydrogen atom, a halogen atom, an alkyl group having from 1 to 6 carbon atoms, an amino group, mono- or di-alkylamino groups, with alkyl group(s) having from 1 to 6 carbon atoms, a haloalkyl group having from 1 to 6 carbon atoms, a cycloalkyl group having from 3 to 8 carbon atoms, a cycloalkenyl group having from 3 to 10 carbon atoms, an aralkyl group, an aryl group or a heteroaryl group;
R⁴ represents an aryl group, or a heteroaryl group;
A represents an aryl¹ group having from 6 to 10 carbon atoms or an heteroaryl¹ group having from 5 to 7 atoms, wherein 1 to 4 of said atoms of one heteroaryl¹ group are independently selected from the group consisting of sulfur atoms, oxygen atoms and nitrogen atoms;
B represents an alkylene group having from 1 to 6 carbon atoms;
X represents NH, N[(C₁–C₆)alkyl], oxygen or sulfur;
said aryl groups have from 6 to 14 carbon atoms;
said heteroaryl groups are 5- to 14-membered aromatic heterocyclic groups containing from 1 to 4 heteroatoms selected from the group consisting of sulfur atoms, oxygen atoms and nitrogen atoms;
said aryl groups and said heteroaryl groups are unsubstituted or are substituted by at least one substituent selected from the group consisting of substituents α, defined below;
said aralkyl groups are alkyl groups having from 1 to 6 carbon atoms and which are substituted by at least one aryl group as defined above;
said substituents α are selected from the group consisting of alkyl group having from 1 to 6 carbon atoms, an aryl group defined above, a heteroaryl group defined above, hydroxy groups, halogen atom, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group having from 1 to 6 carbon atoms in the alkyl and alkoxy part, alkylsulfonylamino group having from 1 to 6 carbon atoms and aminosulfonyl group;
with the proviso that said aryl groups and said heteroaryl groups in said substituents α are not substituted by an aryl group or an heteroaryl group: or a pharmaceutically acceptable ester of such compound, or a pharmaceutically acceptable salt thereof.

Also, the present invention provides a pharmaceutical formulation comprising a compound of formula (I), a pharmaceutically acceptable diluent or carrier and, optionally, one or more other pharmacologically active ingredients.

Also, the present invention provides combination, including a pharmaceutical formulation, comprising a compound of formula (I), or an ester or salt thereof and, one or more other pharmacologically active ingredient(s) selected from a COX-2 selective, COX-1 selective or non-selective NSAID (nonsteroidal anti-inflammatory drug), opioid, anticonvulsant, antidepressant, local anesthetic, disease-modifying anti-rheumatoid drug, or steroid.

DETAILED DESCRIPTION OF THE INVENTION

As used herein, the term "halogen" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "alkanoyl" means a group having carbonyl such as R'—C(O)— wherein R' is $C_{1-6}$ alkyl, phenyl or $C_{3-6}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, cycloheptyl-C(O)—, and the like.

As used herein, the term "aryl" means a monocyclic or bicyclic aromatic carbocyclic ring of 6 to 14 carbon atoms, preferably 6 to 10 carbon atoms including, but not limited to, phenyl, naphthyl, indanyl, preferably phenyl and naphthyl.

As used herein, the term "aryl¹" means a divalent aromatic hydrocarbon ring having from 6 to 14 carbon atoms such as phenylene and naphthylene, preferably a p-phenylene group.

As used herein, the term "heteroaryl¹" means a divalent heteroaromatic ring having from 5 to 7 ring atoms containing from 1 to 4 heteroatoms selected from the group consisting of sulfur atoms, oxygen atoms and nitrogen atoms, such as pyridylene pyrazolylene, furylene, thienylene, oxazolylene, tetrazolylene, thiazolylene, imidazolylene, thiadiazolylene, pyrimidinylene, pyrrolylene, thiophenylene, pyrazinylene, pyridazinylene, isooxazolylene, isothiazolylene, triazolylene, furazanylene and the like, preferably a pyridylene group.

As used herein, the term "aralkyl" means an alkyl radical which is substituted by an aryl group as defined above, e.g. benzyl The term "alkylene", as used herein, means saturated hydrocarbon (straight chain or branched) wherein a hydrogen atom is removed from each of the terminal carbons such as methylene, ethylene, methylethylene, propylene, butylene, pentylene, hexylene and the like.

The term "cycloalkyl", as used herein, means a saturated carbocyclic radical ring of 3 to 8 carbon atoms, including, but not limited to, cyclopropyl, cyclobutyl, cyclohexyl, cycloheptyl, cyclooctyl, cyclononyl, cyclodecyl and the like.

The term "cycloalkenyl", as used herein, means a unsaturated carbocyclic radical ring of 3 to 10 carbon atoms having at least one double bond including, but not limited to, cyclopropenyl, cyclobutenyl, cyclohexenyl, cycloheptenyl, cyclooctenyl, cyclononenyl, cyclodecenyl and the like.

The term "haloalkyl", as used herein, means an alkyl radical which is substituted by halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

The term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "heteroaryl" means a 5- to 14-membered aromatic heterocyclic ring which consists of from 1 to 4 heteroatoms independently selected from the group consisting of N, O and S, including, but not limited to, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

Where the compounds of formula (I) contain hydroxy groups, they may form esters. Examples of such esters include esters with a hydroxy group and esters with a carboxy group. The ester residue may be an ordinary protecting group or a protecting group which can be cleaved in vivo by a biological method such as hydrolysis.

The term "ordinary protecting group" means a protecting group, which can be cleaved by a chemical method such as hydrogenolysis, hydrolysis, electrolysis or photolysis.

The term "protecting group which can be cleaved in vivo by a biological method such as hydrolysis" means a protecting group which is cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of such ordinary protecting groups for an ester of a hydroxy group include: lower aliphatic acyl groups, for example: alkanoyl groups, such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups, such as the chloroacetyl, dichloroacetyl, trichloroacetyl, and trifluoroacetyl groups; alkoxyalkylcarbonyl groups, such as the methoxyacetyl group; and unsaturated alkylcarbonyl groups, such as the acryloyl, propioloyl, methacryloyl, crotonoyl, isocrotonoyl and (E)-2-methyl-2-butenoyl groups; more preferably, the lower aliphatic acyl groups having from 1 to 6 carbon atoms; aromatic acyl groups, for example: arylcarbonyl groups, such as the benzoyl, α-naphthoyl and β-naphthoyl groups; halogenated arylcarbonyl groups, such as the 2-bromobenzoyl and 4-chlorobenzoyol groups; lower alkylated arylcarbonyl groups, such as the 2,4,6-trimethylbenzoyl and 4-toluoyl groups; lower alkoxylated arylcarbonyl groups, such as the 4-anisoyl group; nitrated arylcarbonyl groups, such as the 4-nitrobenzoyl and 2-nitrobenzoyl groups; lower alkoxycarbonylated arylcarbonyl groups, such as the 2-(methoxycarbonyl)benzoyl group; and arylated arylcarbonyl groups, such as the 4-phenylbenzoyl group; alkoxycarbonyl groups, for example: lower alkoxycarbonyl groups, such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(lower alkyl)silyl-substituted lower alkoxycarbonyl groups, such as the 2,2,2-trichloroethoxycarbonyl and 2-trimethylsilylethoxycarbonyl groups; tetrahydropyranyl or tetrahydrothiopyranyl groups, such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups, such as: tetrahydrofuran-2-yl and tetrahydrothiofuran-2-yl groups; silyl groups, for example: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri(lower alkyl)silyl groups substituted by 1 or 2 aryl groups, such as the diphenylmethylsilyl, diphenylbutylsilyl, diphenylisopropylsilyl and phenyldiisopropylsilyl groups; alkoxymethyl groups, for example: lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups; lower alkoxylated lower alkoxymethyl groups, such as the 2-methoxyethoxymethyl group; and halo(lower alkoxy)methyl groups, such as the 2,2,2-trichloroethoxymethyl and bis(2-chloroethoxy)methyl groups; substituted ethyl groups, for example: lower alkoxylated ethyl groups, such as the 1-ethoxyethyl and 1-(isopropoxy)ethyl groups; and halogenated ethyl groups, such as the 2,2,2-trichloroethyl group; aralkyl groups, for example: lower alkyl groups substituted by from 1 to 3 aryl groups, such as the benzyl, α-naphthylmethyl, β-naphthylmethyl, diphenylmethyl, triphenylmethyl, α-naphthyldiphenylmethyl and 9-anthrylmethyl groups; and lower alkyl groups substituted by from 1 to 3 substituted aryl groups, where one or more of the aryl groups is substituted by one or more lower alkyl, lower alkoxy, nitro, halogen or cyano substituents, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups: such as the vinyloxycarbonyl and aryloxycarbonyl groups; and aralkyloxycarbonyl groups in which the aryl ring may be substituted by 1 or 2 lower alkoxy or nitro groups: such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991);

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

Throughout this application, various publications are referenced by citation or number. The disclosures of these publications in their entireties are hereby incorporated by reference into this application.

In the compounds of formula (I), $R^1$ represents preferably, a hydrogen atom, an alkyl group having from 1 to 6 carbon atoms, an aryl group having from 6 to 10 carbon atoms or a heteroaryl group having from 5 to 7 ring atoms; said aryl groups and said heteroaryl groups are unsubstituted or are substituted by at least one substituent selected from the group consisting of substituents α; more preferably, a hydrogen atom, an alkyl group having from 1 to 6 carbon atoms or an unsubstituted aryl group having from 6 to 10 carbon atoms, more preferably, ahydrogen atom, methyl or phenyl.

In the compounds of formula (I), $R^2$ represents preferably a hydrogen atom, a halogen atom, an alkyl group having from 1 to 6 carbon atoms, a cycloalkyl group having from 3 to 8 carbon atoms, an aralkyl group, an aryl group or a heteroaryl group; more preferably, a hydrogen atom, a halogen atom, an alkyl group having from 1 to 6 carbon atoms, a cycloalkyl group having from 3 to 8 carbon atoms, an aralkyl group, an aryl group or a heteroaryl group;

said aryl groups and said heteroaryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, alkanoylamino groups having from 1 to 6 carbon atoms, di-alkylamino group, with alkyl group(s) having from 1 to 6 carbon atoms, haloalkyl groups having from 1 to 6 carbon atoms, carbamoyl groups and cyano groups; more preferably, a hydrogen atom, an alkyl group having from 1 to 6 carbon atoms, a cycloalkyl group having from 3 to 8 carbon atoms, an aryl group having from 6 to 10 carbon atoms or a heteroaryl group having from 5 to 7 atoms, wherein 1 to 4 of said atoms are independently selected from the group consisting of sulfur atoms, oxygen atoms and nitrogen atoms; said aryl groups and said heteroaryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, alkanoylamino groups having from 1 to 6 carbon atoms, di-alkylamino group, with alkyl group(s) having from 1 to 6 carbon atoms, haloalkyl groups having from 1 to 6 carbon atoms and carbamoyl groups; more preferably, a hydrogen atom, an alkyl group having from 1 to 6 carbon atoms, an aryl group having from 6 to 10 carbon atoms or a heteroaryl group having from 5 to 7 atoms, wherein 1 to 4 of said atoms are independently selected from the group consisting of sulfur atoms, oxygen atoms and nitrogen atoms; said aryl groups are unsubstituted or are substituted by at least one substituent selected from the group consisting of substituents α, defined below; said substituents α are selected from the group consisting of alkyl groups having from 1 to 6 carbon atoms, halogen atoms, alkoxy groups having from 1 to 6 carbon atoms, haloalkyl groups having from 1 to 6 carbon atoms and carbamoyl groups; more preferably, an aryl group having from 6 to 10 carbon atoms; said aryl groups are unsubstituted or are substituted by at least one substituent selected from the group consisting of substituents α, defined below; said substituents α are selected from the group consisting of alkyl groups having from 1 to 6 carbon atoms and halogen atoms; more preferably, an aryl group having from 6 to 10 carbon atoms; said aryl groups are unsubstituted or are substituted by at least one halogen atom.

In the compounds of formula (I), $R^3$ represents preferably, a hydrogen atom, an alkyl group having from 1 to 6 carbon atoms, an amino group, mono- or di-alkylamino group, with alkyl group(s) having from 1 to 6 carbon atoms, a haloalkyl group having from 1 to 6 carbon atoms, an aryl group having from 6 to 10 carbon atoms; said aryl groups and said heteroaryl groups are unsubstituted or are substituted by at least one substituent selected from the group consisting of substituents α; more preferably, a hydrogen atom, an alkyl group having from 1 to 6 carbon atoms, an amino group, a haloalkyl group having from 1 to 6 carbon atoms, an aryl group having from 6 to 10 carbon atoms; more preferably, a hydrogen atom, an alkyl group having from 1 to 6 carbon atoms, an amino group or an aryl group having from 6 to 10 carbon atoms; more preferably, an alkyl group having from 1 to 6 carbon atoms or an amino group.

In the compounds of formula (I), $R^4$ represents an aryl or a heteroaryl group; said aryl groups and said heteroaryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, haloalkoxy groups having from 1 to 6 carbon atoms, alkanoyl groups having from 1 to 6 carbon atoms, alkanoylaminoalkyl groups having from 1 to 6 carbon atoms in the alkanoyl and alkyl part, haloalkyl groups having from 1 to 6 carbon atoms, carbamoyl groups, cyano groups and aminosulfonyl groups; more preferably, a aryl group having from 6 to 10 carbon atoms, or a heteroaryl group having from 5 to 7 atoms, wherein 1 to 4 of said atoms are independently selected from the group consisting of sulfur atoms, oxygen atoms and nitrogen atoms; said aryl groups and said heteroaryl groups are unsubstituted or are substituted by at least one substituent selected from the group consisting of substituents α, defined below; and said substituents α are selected from the group consisting of alkyl groups having from 1 to 6 carbon atoms, hydroxy groups, halogen atoms, alkoxy groups having from 1 to 6 carbon atoms, alkanoyl groups having from 1 to 6 carbon atoms, haloalkyl groups having from 1 to 6 carbon atoms, carbamoyl groups, cyano groups and aminosulfonyl groups; more preferably, a aryl group having from 6 to 10 carbon atoms, or a heteroaryl group; said heteroaryl groups are selected from the group consisting of pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl and furazanyl; said aryl groups and said heteroaryl groups are unsubstituted or are substituted by at least one substituent selected from the group consisting of substituents α, defined below ; and said substituents α are selected from the group consisting of alkyl groups having from 1 to 6 carbon atoms, hydroxy groups, halogen atoms, alkoxy groups having from 1 to 6 carbon atoms, alkanoyl groups having from 1 to 6 carbon atoms, haloalkyl groups having from 1 to 6 carbon atoms, carbamoyl groups, cyano groups and aminosulfonyl groups; more preferably, a aryl group having from 6 to 10 carbon atoms; said aryl groups is unsubstituted or are substituted by at least one substituent selected from the group consisting of substituents α, defined below; and said substituents α are selected from the group consisting of alkyl groups having from 1 to 6 carbon atoms, halogen atoms, alkoxy groups having from 1 to 6 carbon atoms and cyano groups; more preferably, phenyl, phenyl substituted by at least one substituent selected from the group consisting of substituents α, defined below; and said substituents α are selected from the group consisting of methyl groups, halogen atomsmethoxy groups and cyano groups.

In the compounds of formula (I), A represents preferably, an aryl$^1$ group having from 6 to 10 carbon atoms or an hetero aryl$^1$ group having from 5 to 7 atoms, wherein 1 to 4 of said atoms are independently selected from the group consisting of sulfur atoms, oxygen atoms and nitrogen atoms; more preferably, a phenylene or pyridylene, more preferably, a phenylene.

In the compounds of formula (I), B represents preferably ethylene.

In the compounds of formula (I), X represents preferably, NH, oxygen or sulfur.

Preferred individual compounds of this invention are following:

2-[4-(4-phenyl-1H-imidazole-1-yl)phenyl]ethyl (4-methylphenyl)sulfonylcarbamate;

2-[4-(2-amino-4,5-diphenyl-1H-imidazol-1-yl)phenyl]ethyl (4-methylphenyl) sulfonylcarbamate;

2-[4-(2-ethyl-4-phenyl-1Himidazole-1-yl)phenyl]ethyl (4-methylphenyl) sulfonylcarbamate;

N-[({2-[4-(2-ethyl-4-phenyl-1H-imidazol-1-yl)phenyl]ethyl}amino)carbonyl]-4-methylbenzenesulfonamide;

2-chloro-N-[({2-[4-(2-ethyl-4-phenyl-1H-imidazol-1-yl)phenyl]ethyl}amino)carbonyl]benzenesulfonamide;

2-[4-(2,4-diphenyl-1H-imidazol-1-yl)phenyl]ethyl (4-methylphenyl)sulfonylcarbamate;

2-[4-(2-butyl-4-phenyl-1H-imidazol-1-yl)phenyl]ethyl (2-chlorophenyl) sulfonylcarbamate;

2-[4-(2-isobutyl-4-phenyl-1H-imidazol-1-yl)phenyl]ethyl (2-chlorophenyl) sulfonylcarbamate;

2-[4-(2-isopropyl-4-phenyl-1H-imidazol-1-yl)phenyl]ethyl (2-chlorophenyl) sulfonylcarbamate;

N-[({2-[4-(2-ethyl-4-phenyl-1H-imidazol-1-yl)phenyl]ethyl}amino)carbonyl]-5-methyl-2-pyridinesulfonamide;

4-chloro-N-[({2-[4-(2-ethyl-4-phenyl-1H-imidazol-1-yl)phenyl]ethyl}amino)carbonyl]benzenesulfonamide;

4-fluoloro-N-[({2-[4-(2-ethyl-4-phenyl-1H-imidazol-1-yl)phenyl]ethyl}amino) carbonyl]benzenesulfonamide;

2-[4-(2-tert-butyl-4-phenyl-1H-imidazol-1-yl)phenyl]ethyl (2-chlorophenyl) sulfonylcarbamate; and 4-chloro-N-[({2-[4-(2-isopropyl-4-phenyl-1H-imidazol-1-yl)phenyl]ethyl}amino) carbonyl]benzenesulfonamide or an ester of such compound, and salts thereof.

Most preferred individual compounds of this invention are following:

2-[4-(2-amino-4,5-diphenyl-1H-imidazol-1-yl)phenyl]ethyl (4-methylphenyl) sulfonylcarbamate;

2-[4-(2-ethyl-4-phenyl-1Himidazole-1-yl)phenyl]ethyl (4-methylphenyl) sulfonylcarbamate;

N-[({2-[4-(2-ethyl-4-phenyl-1H-imidazol-1-yl)phenyl]ethyl}amino)carbonyl]-4-methylbenzenesulfonamide;

2-chloro-N-[({2-[4-(2-ethyl-4-phenyl-1H-imidazol-1-yl)phenyl]ethyl}amino) carbonyl]benzenesulfonamide;

2-[4-(2-butyl-4-phenyl-1H-imidazol-1-yl)phenyl]ethyl (2-chlorophenyl) sulfonylcarbamate;

2-[4-(2-isobutyl-4-phenyl-1H-imidazol-1-yl)phenyl]ethyl (2-chlorophenyl) sulfonylcarbamate;

2-[4-(2-isopropyl-4-phenyl-1H-imidazol-1-yl)phenyl]ethyl (2-chlorophenyl) sulfonylcarbamate;

4-chloro-N-[({2-[4-(2-ethyl-4-phenyl-1H-imidazol-1-yl)phenyl]ethyl}amino) carbonyl]benzenesulfonamide;

N-[({2-[4-(2-ethyl-4-phenyl-1H-imidazol-1-yl)phenyl]ethyl}amino)carbonyl]-4-methoxybenzenesulfonamide; and 2-[4-(2-tert-butyl-4-phenyl-1H-imidazol-1-yl)phenyl]ethyl (2-chlorophenyl) sulfonylcarbamate;

or a ester of such compound, and salts thereof.

General Synthesis

The compounds of the present invention may be prepared by a variety of processes well known for the preparation of compounds of this type, for example as shown in the following reaction Schemes. Unless otherwise indicated $R^1$ through $R^4$ and A, B and X in the reaction Schemes and discussion that follow are defined as above.

The following reaction Schemes. illustrate the preparation of compounds of formula (I).

Scheme 1

This illustrates the preparation of compounds of formula (I).

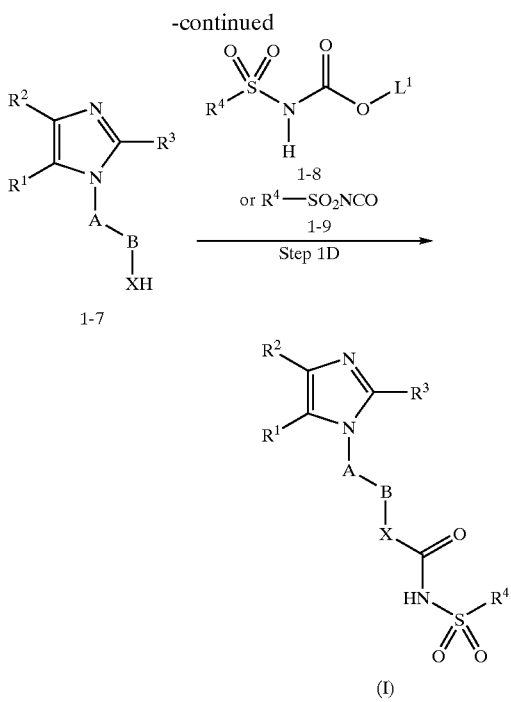

In the above formula, $L^1$ represents an alkyl group having from 1 to 6 carbon atoms, a substituted alkyl group having from 1 to 6 carbon atoms, an aryl group having from 6 to 10 carbon atoms or a substituted aryl group having from 6 to 10 carbon atoms.

Step 1A

In this Step, a 2-carbonyl-amine compound of formula 1-3 may be prepared by substitution of a halogenated 2-carbonyl compound of formula 1-2 with an amine compound of formula 1—1 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride and dichloroethane; ethers, such as diethyl ether, diisopropyl ether, tetrahydrofuran and dioxane; ketones, such as acetone, methylethylketone and methylvinylketone; N,N-dimethylformamide(DMF), dimethylsulfoxide(DMSO); and alcohols, such as methanol, ethanol propanol and isopropanol. Of these solvents, we prefer acetone.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from 0° C. to 150° C. The time required for the reaction may also vary widely, depending on many factors, notably the reaction temperature and the nature of the reagents and solvent employed. However, provided that the reaction may be effected under the preferred conditions outlined above, a period of from 10 minutes to 60 hours, more preferably from 1 hour to 30 hours, will usually suffice.

This reaction may be carried out in the presence or absence of a base. There is likewise no particular restriction on the nature of the bases used, and any base commonly used in reactions of this type may equally be used here. Examples of such bases include: an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine.

This reaction may be carried out in the presence a suitable catalyst. There is likewise no particular restriction on the nature of the catalysts used, and any catalysts commonly used in reactions of this type may equally be used here. Examples of such catalysts include: potassium iodide, sodium iodide.

Step 1B

In this Step, a 2-carbonyl-amide compound of formula 1-6 may be prepared by acylation of the 2-carbonyl-amine compound of formula 1-3, prepared as described in Step 1A with acylating agents selected from the groups consisting of formula 1-4 and 1-5 in an inert solvent.

The acylation reaction may be carried out by conventional methods. Examples of suitable acylating agents include: an acid halide, an acid anhydride or trialkyl orthoformate, and the like.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride and dichloroethane; ethers, such as diethyl ether, diisopropyl ether, tetrahydrofuran and dioxane. Of these solvents, we prefer the halogenated hydrocarbons.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −50° C. to 100° C., more preferably from −20° C. to 50° C. The time required for the reaction may also vary widely, depending on many factors, notably the reaction temperature and the nature of the reagents and solvent employed. However, provided that the reaction may be effected under the preferred conditions outlined above, a period of from 1 minute to 10 hours, more preferably from 10 minutes to 5 hours, will usually suffice.

This reaction may be carried out in the presence or absence of a base. There is likewise no particular restriction on the nature of the bases used, and any base commonly used in reactions of this type may equally be used here. Examples of such bases include: pyridine, picoline, 4-(N,N-dimethylamino)pyridine, triethylamine, tributylamine, diisopropylethylamine, N-methylmorphorine and N-methylpiperidine.

Step 1C

In this Step, an imidazole compound of formula 1-7 may be prepared by the cyclization of the 2-carbonyl-amide compound of formula 1-6, prepared as described in Step 1B under conditions known to those skilled in the art. (e.g., *Chem. Ber.*, 380 (1957)).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; ethers, such as diethyl ether, diisopropyl ether, tetrahydrofuran and dioxane; alcohols, such as methanol, ethanol, propanol, isopropanol and butanol; and organic acids, such as acetic acid and propionic acid. Of these solvents, we prefer the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from room temperature to 150° C. The time required for the reaction may also vary widely, depending on many factors, notably the reaction temperature and the nature of the reagents and solvent employed. However, provided that the reaction may be effected under the preferred conditions outlined above, a period of from 10 minutes to 60 hours, more preferably from 1 hour to 30 hours, will usually suffice.

This reaction may be carried out in the presence or absence of an acid catalyst. Examples of suitable acids include: hydrochoric acid and acetic acid.

This reaction may be carried out in the presence of a suitable additive agent. Examples of suitable additive agents include: ammonium acetate.

Step 1D

In this Step, the desired compound of formula (I), which is a compound of the present invention, may be prepared by the reacting the compound of formula 1-7, prepared as described in Step 1C with compounds selected from the groups consisting of formula 1-8 and 1-9 in an inert solvent.

The reaction may be carried out in the absence or presence of a reaction inert solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, xylene, o-dichlorobenzene, nitrobenzene and pyridine; halogenated hydrocarbons, such as methylene chloride, chloroform, carbon tetrachloride and dichloroethane; ethers, such as diethyl ether, diisopropyl ether, tetrahydrofuran and dioxane; ethyl acetate, acetonitrile, NAN-dimethylformamide, dimethylsulfoxide. Of these solvents, we prefer the halogenated hydrocarbons and pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 24 hours, more preferably from 20 minutes to 5 hours, will usually suffice.

This reaction may be carried out in the presence or absence of a base. There is likewise no particular restriction on the nature of the bases used, and any base commonly used in reactions of this type may equally be used here. Examples of such bases include: pyridine, picoline, triethylamine, tributylamine, diisopropylethylamine, N-methylmorphorine, N-methylpiperidine, 4-(N,N-dimethylamino)pyridine.

Compounds of formula 1-2, 1-4, 1-5, 1-8 or 1-9 may be a known compound or readily prepared by known methods (e.g., *Heterocycles*, 1994, 37, 796).

Scheme 2

This illustrates the preparation of compounds of formula (Ia) wherein X represents NH or N[($C_1$–$C_6$)alkyl].

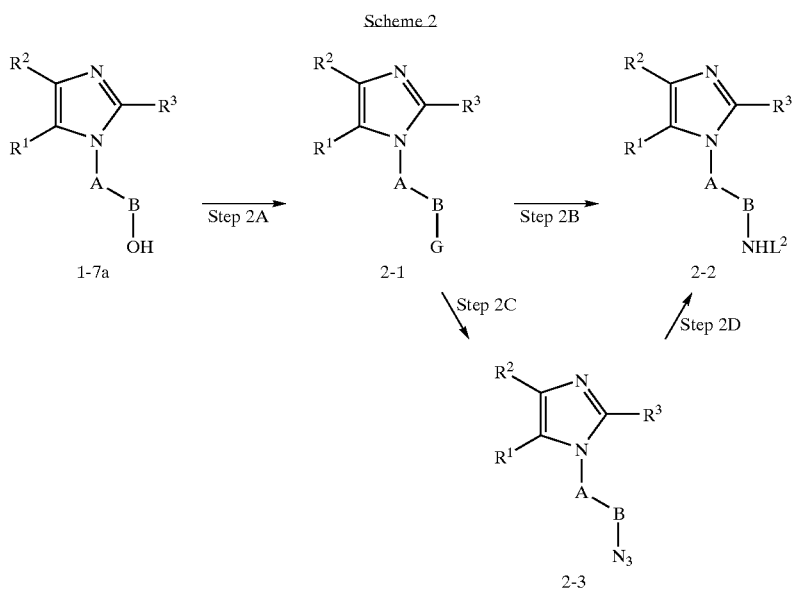

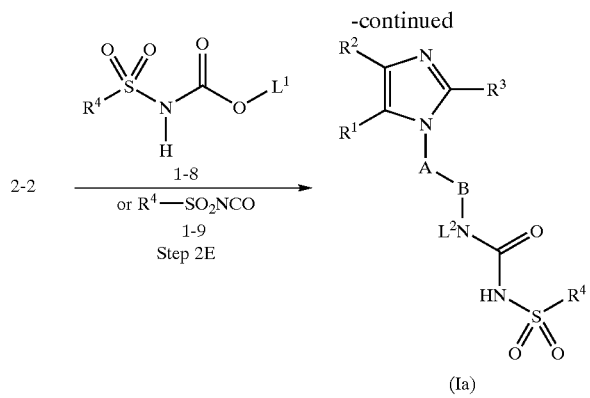

In the above formula, $L^2$ represents a hydrogen atom or an alkyl group having from 1 to 6 carbon atoms.

G represents a leaving group. Example of suitable leaving groups includes: halogen atoms, such as chlorine, bromine and iodine; sulfonic esters such as TfO (triflates), MsO (mesylates), TsO (tosylates); and the like.

Step 2A

In this Step, an imidazole compound of formula 1-7a, prepared as described in Step 1C in Scheme 1 (compounds of formula 1-7 wherein X is oxygen), may be converted to compound with a leaving group G of formula 2-1 under conditions known to those skilled in the art.

For example, the hydroxy group of the compound of formula 1-7a may be converted to the halogen atom using a halogenating agent in the presence or absence of a reaction inert solvent. Preferred halogenating agents include: chlorinating agents, such as thionyl chloride, oxalyl chloride, para-toluenesulfonyl chloride, methanesulfonyl chloride, hydrogen chloride, phosphorus trichloride, phosphorus pentachloride, N-chlorosuccinimide (NCS), phosphorus oxychloride, or phosphorus reagents such as triphenylphosphine, tributyl phosphine or triphenylphosphite in the presence of halogen source such as carbon tetrachloride, chlorine, NCS; brominating agents, such as hydrogen bromide, N-bromosuccinimide (NBS), phosphorus tribromide, trimethylsilyl bromide or phosphorus reagents such as triphenylphosphine, tributyl phosphine or triphenylphosphite in the presence of halogen source such as carbon tetrabromide, bromine or NBS; and iodinating agents, such as hydroiodic acid, phosphorus triiodide, or phosphorus reagents such as triphenylphosphine, tributyl phosphine or triphenylphosphite in the presence of halogen source such as iodine.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, o-dichlorobenzene, nitrobenzene, pyridine, and xylene; halogenated hydrocarbons, such as methylene chloride, chloroform, carbon tetrachloride and 1,2-dichloroethane; and ethers, such as diethyl ether, diisopropyl ether, tetrahydrofuran and dioxane. Of these solvents, we prefer the aromatic hydrocarbons, halogenated hydrocarbons and ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 5 hours, will usually suffice.

Alternatively, a hydroxy group of the compound of formula 1-7a may be converted to the sulfonate group using a sulfonating agent in the presence of, or absence of a base. Example of such sulfonating agents includes: para-toluenesulfonyl chloride, para-toluenesulfonic anhydride, methanesulfonyl chloride, methanesulfonic anhydride, trifluoromethanesulfonic anhydride, or the like in the presence of, or absence of a reaction-inert solvent. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of a reaction inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, o-dichlorobenzene, nitrobenzene, pyridine, and xylene; halogenated hydrocarbons, such as methylene chloride, chloroform, carbon tetrachloride and 1,2-dichloroethane; and ethers, such as diethyl ether, diisopropyl ether, tetrahydrofuran and dioxane; N,N-dimethylformamide, and dimethylsulfoxide The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 5 hours, will usually suffice.

Step 2B

In this Step, an imidazole compound of formula 2—2 may be prepared by the amination of the above obtained compound of formula 2-1 with $L^2$-$NH_2$ wherein $L^2$ is as defined above in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water, aliphatic hydrocarbons, aliphatic hydrocarbons, such as hexane, heptane and petroleum ether; aromatic hydrocarbons, such as benzene, toluene o-dichlorobenzene, nitrobenzene, pyridine, and xylene; halogenated hydrocarbons, such as methylene chloride, chloroform, carbon tetrachloride and 1,2-dichloroethane; ethers, such as tetrahydrofuran and dioxane; and alcohols, such as methanol, ethanol, propanol, isopropanol, butanol and ethylene glycol. Of these solvents, we prefer the aromatic hydrocarbons, ethers, and alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

This reaction may be carried out in the presence or absence of a base. There is likewise no particular restriction on the nature of the bases used, and any base commonly used in reactions of this type may equally be used here. Examples of such bases include: an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine, dimethylaminopyridine, 1,8-diazabicyclo[5.4.0]undec-7-ene.

Step 2C

In this Step, an azide compound of formula 2-3 may be prepared by the nucleophilic displacement of the above obtained compound of formula 2-1 with azide in an inert solvent.

Examples of suitable azide agents include sodium azide or lithium azide.

This reaction may be carried out in the presence of a suitable additive agent. Examples of such additive agents include: sodium iodide, potassium iodide, 1,4,7,10.13-pentaoxacyclopentadecane(15-Crown-5) or 1,4,7,10-tetraoxacyclododecane (12-Crown-4).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; aromatic hydrocarbons, such as benzene, toluene, o-dichlorobenzene, nitrobenzene, pyridine, and xylene; ethers, such as tetrahydrofuran and dioxane and N,N-dimethylformamide and dimethoxyethane. Of these solvents, we prefer the water and N,N-dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

Step 2D

In this Step, which is an alternative to Step 2B, the amine compound of formula 2-2 may be prepared by carrying out reduction of the azide compound of formula 2-3, prepared as described in Step 2C.

The reduction may also be carried out under known hydrogenation conditions in the presence of a metal catalyst such as Lindlar catalysts, Raney nickel catalysts, palladium catalysts or platinum catalysts (preferably Lindlar catalysts, palladium catalysts or platinum catalysts). This reaction may be carried out under hydrogen atmosphere in a reaction inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetic acid, alcohols, such as methanol, ethanol; ethyl acetate, tetrahydrofuran, and N,N-dimethylformamide. Of these solvents, we prefer the alcohols and NAN-dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

Step 2E

In this Step, the desired compound of formula (Ia), which is a compound of the present invention, may be prepared by the reacting the compound of formula 2—2, prepared as described in Step 2B and 2D with compounds selected from the groups consisting of formula 1-8 or 1-9 in an inert solvent.

This reaction is essentially the same as and may be carried out in the same manner as and using the same reagents and reaction conditions as Step 1D in Scheme 1.

Scheme 3

This illustrates the alternative preparation of compounds of formula (I).

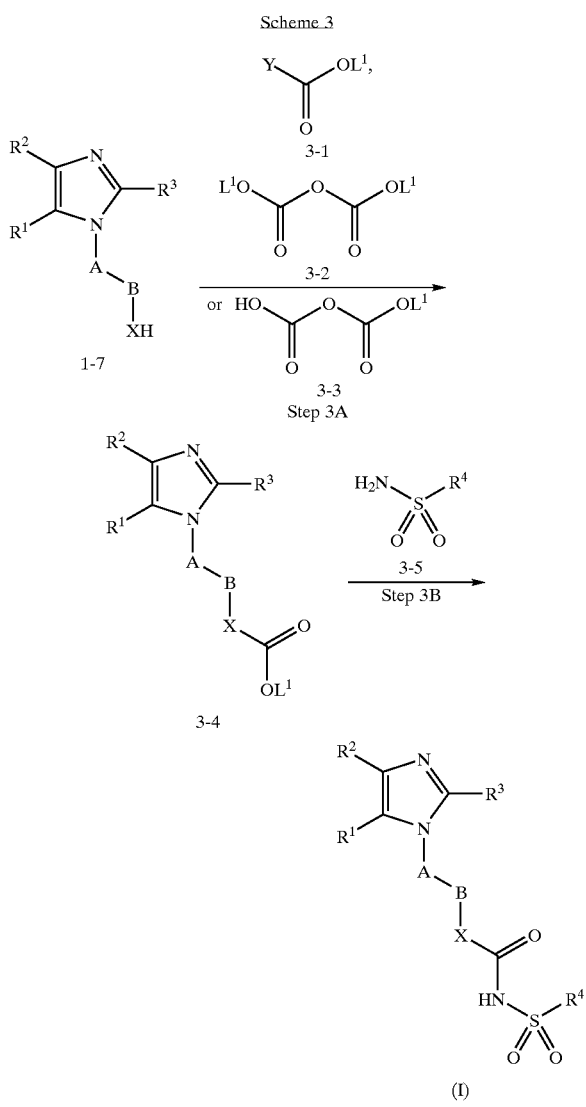

In the above formula, Y represents a halogen atom, for example, chlorine, bromine and iodine.

Step 3A

In this Step, a carbonyl imidazole compound of formula 3-4 may be prepared by the coupling of an imidazole compound of formula 1-7, prepared as described in Step 1C in Scheme 1 with compounds selected from the groups consisting of formula 3-1,3-2 and 3—3 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, o-dichlorobenzene, nitrobenzene, pyridine and xylene; halogenated hydrocarbons, such as methylene chloride, chloroform, carbon tetrachloride and 1,2-dichloroethane; ethers, such as diethyl ether, diisopropyl ether, tetrahydrofuran and dioxane; N,N-dimethylformamide, dimethylsulfoxide. Of these solvents, we prefer the halogenated hydrocarbons and pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0 to 150° C. The time required for the reaction may also vary widely, depending on many factors, notably the reaction temperature and the nature of the reagents and solvent employed. However, provided that the reaction may be effected under the preferred conditions outlined above, a period of from 10 minutes to 24 hours, more preferably from 20 minutes to 5 hours, will usually suffice.

This reaction may be carried out in the presence or absence of a base. Examples of suitable bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, pyridine or dimethylaminopyridine.

Step 3B

In this Step, the desired compound of formula (I), which is a compound of the present invention, may be prepared by the reacting the compound of formula 3-4, prepared as described in Step 3A with a sulfonamide compound of formula 3-5 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, o-dichlorobenzene, nitrobenzene, pyridine and xylene; halogenated hydrocarbons, such as methylene chloride, chloroform, carbon tetrachloride and dichloroethane; ethers, such as diethyl ether, diisopropyl ether, tetrahydrofuran and dioxane; acetonitrile, N,N-dimethylformamide, N,N-dimethylsulfoxide. Of these solvents, we prefer N,N-dimethylformamide and acetonitrile.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to 150° C. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

This reaction may be carried out in the presence or absence of a base. Examples of suitable bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, pyridine or dimethylaminopyridine, 1,8-diazabicyclo[5.4.0]undec-7-ene.

Compounds of formula 3-1, 3-2, 3—3 or 3-5 may be a known compound or readily prepared by known methods.
Scheme 4

This illustrates the preparation of compounds of formula (I).

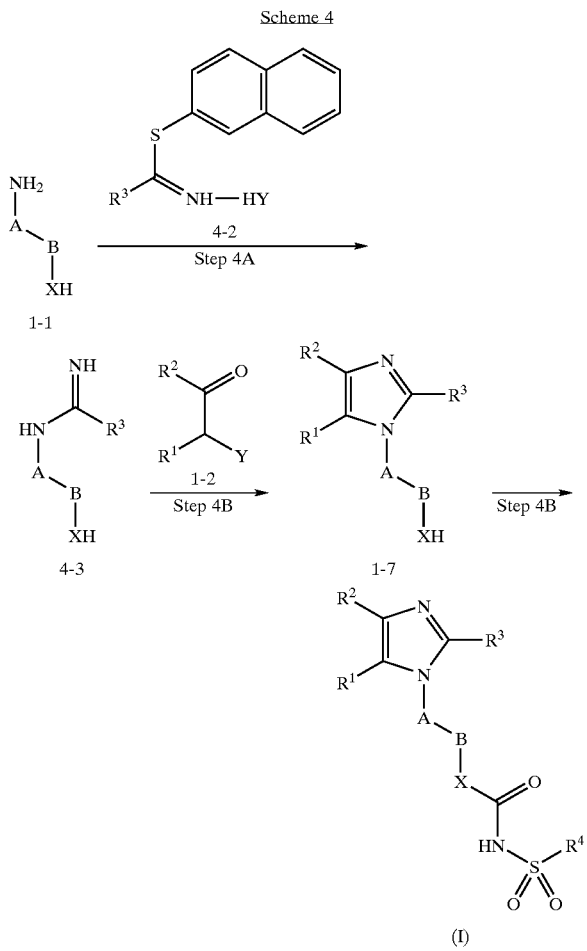

Step 4A

In this Step, an amine compound of formula 1—1 may be converted to an amidine compound of formula 4-3 by reacting with a compound of formula 4-2 under conditions known to those skilled in the art (e.g., *Tetrahedron Lett.*, 38. 179(1997)).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene o-dichlorobenzene, nitrobenzene, pyridine, and xylene; halogenated hydrocarbons, such as methylene chloride, chloroform, carbon tetrachloride and dichloroethane; and ethers, such as diethyl ether, diisopropyl ether, tetrahydrofuran, dimethoxyethane and dioxane; alcohols, such as methanol, ethanol, propanol, isopropanol and butanol; dimethylformamide (DMF), dimethylsulfoxide (DMSO) or acetonirile. Of these solvents, we prefer the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to 100° C. The time required for the reaction may also vary widely, depending on many factors, notably the reaction temperature and the nature of the reagents and solvent employed. However, provided that the reaction may be effected under the preferred conditions outlined above, a period of from 1 minute to 2 days, more preferably from 20 minutes to 24 hours, will usually suffice.

Step 4B

In this Step, an imidazole compound of formula 1-7 may be prepared by the condensation of the above obtained compound of formula 4-3 with the halogenated 2-carbonyl compound of formula 1-2 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene o-dichlorobenzene, nitrobenzene, pyridine, and xylene; halogenated hydrocarbons, such as methylene chloride, chloroform, carbon tetrachloride and dichloroethane; and ethers, such as diethyl ether, diisopropyl ether, dimethoxyethane (DME), tetrahydrofuran and dioxane; alcohols, such as methanol, ethanol, propanol, isopropanol and butanol. Of these solvents, we prefer the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 300° C., more preferably from 0° C. to 250° C. The time required for the reaction may also vary widely, depending on many factors, notably the reaction temperature and the nature of the reagents and solvent employed. However, provided that the reaction may be effected under the preferred conditions outlined above, a period of from 1 minute to 2 days, more preferably from 20 minutes to a day, will usually suffice.

This reaction may be carried out in the presence or absence of a base. There is likewise no particular restriction on the nature of the bases used, and any base commonly used in reactions of this type may equally be used here. Examples of such bases include: an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine.

Step 4C

In this Step, the desired compound of formula (I), which is a compound of the present invention, may be prepared by the reacting the compound of formula 1-7, prepared as described in Step 4B.

This reaction is essentially the same as and may be carried out in the same manner as and using the same reagents and reaction conditions as Step 1D in Scheme 1 and Steps 3A and 3B in Scheme 3.

Compounds of formula 4-2 may be a known compound or readily prepared by known methods (e.g., *Tetrahedron Lett.*, 38. 179(1997)).

Scheme 5

This illustrates the preparation of compounds of formula (Ib) wherein $R^{3a}$ represents an alkyl group having from 1 to 6 carbon atoms; a haloalkyl group having from 2 to 6 carbon atoms, a cycloalkyl group having from 3 to 8 carbon atoms, a cycloalkenyl group having from 3 to 10 carbon atoms, an aralkyl group.

Scheme 5

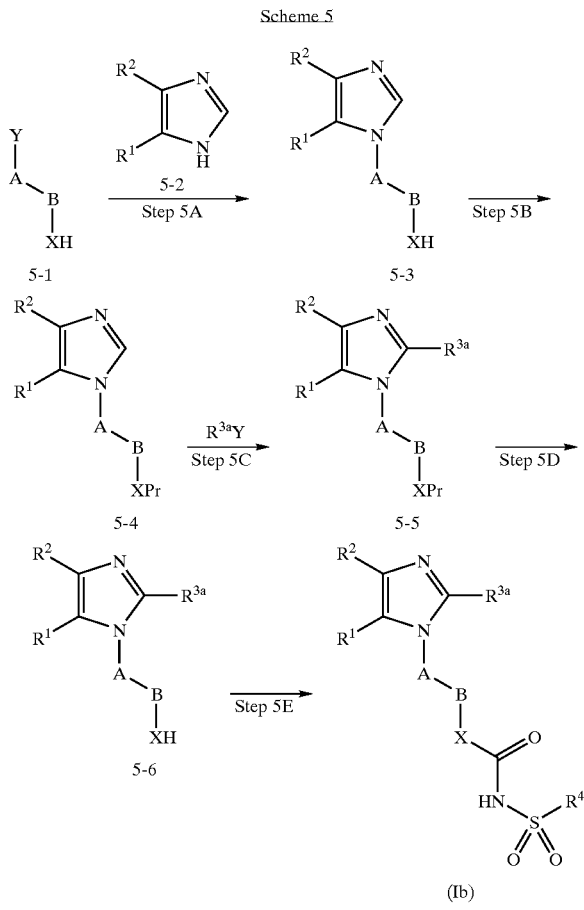

In the above formula, Pr represents a protecting group group. The term "protecting group", as used herein, means a hydroxy, thiol or amino protecting group which is selected from typical hydroxy, thiol or amino protecting groups described in Protective Groups in Organic Synthesis edited by T. W. Greene et al. (John Wiley & Sons, 1991). Typical hydroxy, thiol or amino protecting groups include benzyl, $C_2H_5O(C=O)-$, $CH_3(C=O)-$, t-butyldimethylsilyl (TBS), t-butyldiphenylsilyl, benzyloxycarbonyl represented as Z and t-buthoxycarbonyl represented as t-Boc or Boc.

Step 5A

In this Step, an imidazole compound of formula 5-3 may be prepared by the coupling of a halide compound of formula 5-1 with a N-unsubstituted imidazole compound of formula 5-2 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, xylene and nitrobenzene; halogenated hydrocarbons, such as methylene chloride, chloroform, carbon tetrachloride and dichloroethane; ethers, such as diethyl ether, diisopropyl ether, tetrahydrofuran and dioxane; alcohols, such as methanol, ethanol, propanol, isopropanol and butanol; and dimethylformamide (DMF), dimethylsulfoxide (DMSO), 1,3-dimethyl-2-imidazolidinone(DMI) or acetonirile. Of these solvents, we prefer the aromatic hydrocarbons or DMI.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 250° C., more preferably from room temperature to 200° C. The time required for the reaction may also vary widely, depending on many factors, notably the reaction temperature and the nature of the reagents and solvent employed. However, provided that the reaction may be effected under the preferred conditions outlined above, a period of from 10 minutes to 60 hours, more preferably from 1 hour to 50 hours, will usually suffice.

This reaction may be carried out in the presence of a base. There is likewise no particular restriction on the nature of the bases used, and any base commonly used in reactions of this type may equally be used here. Examples of such bases include: an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, cesium carbonate, sodium hydride or potassium hydride, or an amine such as triethylamine, tributylamine, diisopropylethylamine, pyridine or dimethylaminopyridine.

This reaction may be carried out in the presence of a suitable additive. There is likewise no particular restriction on the nature of the catalysts used, and any catalysts commonly used in reactions of this type may equally be used here. Examples of such catalysts include: tetrakis (triphenylphosphine)-palladium, bis(triphenylphosphine) palladium(II) chloride, copper(0), copper(I) acetate, copper (I) bromide, copper(I) chloride, copper(I) iodide, copper(I) oxide, copper(I) trifluoromethanesulfonate, copper(II) acetate, copper(II) bromide, copper(II) chloride, copper(II) iodide, copper(II) oxide, 1,10-phenanthroline, dibenzanthracene(DBA) or copper(II) trifluoromethanesulfonate.

Step 5B

In these Steps, a protected compound of formula 5-4 may be prepared from a compound of formula 5-3, prepared as described in Step 5A, by converting the XH group into a protected X group. The steps may be carried out by using, for example, the compound of formula 5-3, appropriate silyl halides, aralkyl halide, acid halides, acid anhydride and acids, such as benzyl, t-butyldimethylsilyl (TBS) chloride, t-butyldiphenylsilylchloride, Z-chloride and t-BocCl or Boc$_2$O, using the methods described in Protective Groups in Organic Synthesis edited by T. W. Greene et al. (John Wiley & Sons, 1991).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride and dichloroethane; and ethers, such as diethyl ether, diisopropyl ether, tetrahydrofuran and dioxane; and DMF and DMSO. Of these solvents, we prefer the halogenated hydrocarbons.

This reaction may be carried out in the presence or absence of a base. There is likewise no particular restriction on the nature of the bases used, and any base commonly used in reactions of this type may equally be used here. Examples of such bases include: pyridine, imidazole, picoline, 4-(N,N-dimethylamino)pyridine, triethylamine, tributylamine, diisopropylethylamine, N-methylmorphorine and N-methylpiperidine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 24 hours, more preferably from 20 minutes to 5 hours, will usually suffice.

Step 5C

In this Step, a 2-substituted imidazole compound of formula 5—5 may be prepared by the alkylation of the compound of formula 5-4, prepared as described in Step 5B with halide reagents $R^{3a}Y$ in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene o-dichlorobenzene, nitrobenzene, and xylene; and ethers, such as diethyl ether, diisopropyl ether, tetrahydrofuran and dioxane. Of these solvents, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 100° C., more preferably from −100° C. to the room temperature. The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 5 hours, will usually suffice.

This reaction may be carried out in the presence of a base. There is likewise no particular restriction on the nature of the bases used, and any bases commonly used in reactions of this type may equally be used here. Examples of such bases include: lithium, alkyllithium, such as n-butyllithium, tert-butyllithiun, sec-butyllithium, aryllithium such as phenylithium.

Step 5D

In this Step, a 2-substituted imidazole compound of formula 5-6 may be prepared by the deprotection of the compound of formula 5—5, prepared as described in Step 5C, according to known procedures such as those described in Protective Groups in Organic Synthesis edited by T. W. Greene et al. (John Wiley & Sons, 1991).

Typical amino protecting groups include benzyl represented as Bn, benzyloxycarbonyl represented as Cbz or Z and t-But-O—C(=O)— represented as t-Boc or Boc. In the case of Bn or Z protection, the removal of the amino protecting groups may be carried out under, for example, known hydrogenolysis conditions in the presence of a metal catalyst under hydrogen atmosphere or in the presence of hydrogen sources such as formic acid or ammonium formate in a reaction inert solvent. If desired, the reaction is carried out under acidic conditions, for example, in the presence of hydrochloric acid or acetic acid. A preferred metal catalyst is selected from, for example, palladium catalysts such as Pd—C. Preferred reaction inert solvents include, but are not limited to, methanol, ethanol, ethyl acetate, THE or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed. In the case of Boc protection, the removal of the amino protecting groups may be carried out under, for example, known acid hydrolysis conditions in a reaction inert solvent or without solvent. If desired, the reaction is carried out under acidic conditions, for example, in the presence of hydrochloric acid or trifluoroacetic acid with a reaction inert scavenger of t-butyl cations. Preferred reaction inert scavenger of t-butyl cations include, but are not limited to, benzene, thiophenol, anisole, thioanisole, thiocresole, cresole, or dimethyl sulfide. Preferred reaction inert solvents include, but are not limited to, methanol, ethanol, ethyl acetate, dioxane or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed.

Step 5E

In this Step, the desired compound of formula (Ib), which is a compound of the present invention, may be prepared by the sulfonating the compound of formula 5-6, prepared as described in Step 5D.

This reaction is essentially the same as and may be carried out in the same manner as and using the same reagents and reaction conditions as Step 1 D in Scheme 1 and Steps 3A and 3B in Scheme 3.

Compounds of formula 5-1, 5-2 and $R^{3a}Y$ may be a known compound or readily prepared by known methods.

Scheme 6

This illustrates the preparation of compounds of formula (Ic) wherein $R^{3b}$ represents an aryl group or a heteroaryl group.

Scheme 6

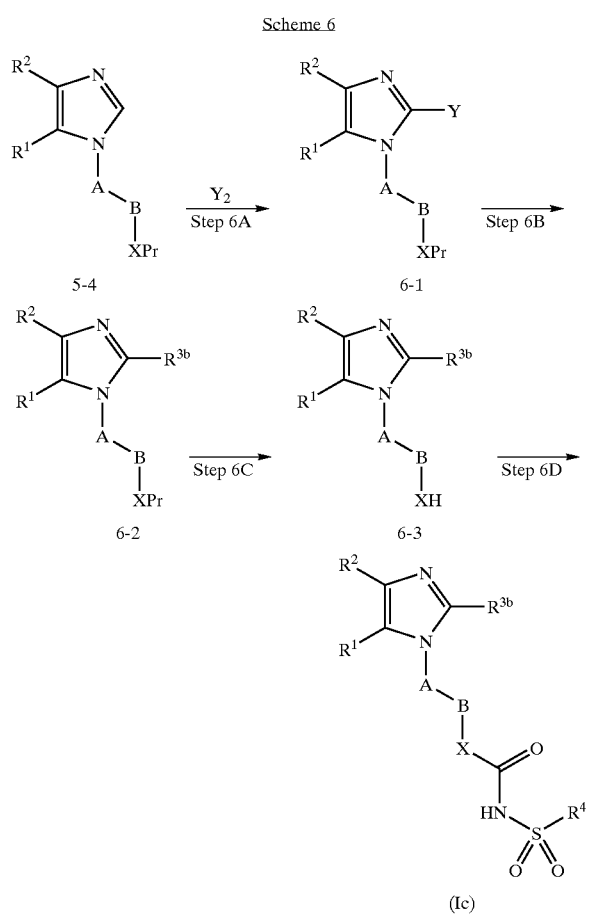

In the above formula, $R^{3b}$ represents an aryl group or a heteroaryl group.

Step 6A

In this Step, an imidazole compound of formula 6-1 may be prepared by halogenation of a compound of formula 5-4, prepared as described in Step 5B with halogenating agents. Under conditions known to those skilled in the art.

For example, the hydrogen atom of the compound of formula 5-4 may be converted to the halogen atom using a halogenating agent in the presence or absence of a reaction inert solvent. Preferred halogenating agents include: chlorinating agents, such as chlorine, N-chlorosuccinimide (NCS), trichloroacetylchloride, brominating agents, such as bromine, N-bromosuccinimide (NBS); and iodinating agents, such as iodine and N-iodosuccinimide (NIS).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene o-dichlorobenzene, nitrobenzene, pyridine, and xylene; and ethers, such as diethyl ether, diisopropyl ether, tetrahydrofuran and dioxane, Of these solvents, we prefer tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from −100° C. to 100° C. The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 12 hours, will usually suffice.

This reaction may be carried out in the presence of a base. There is likewise no particular restriction on the nature of the bases used, and any base commonly used in reactions of this type may equally be used here. Examples of such bases include: lithium, alkyllithium, such as n-butyllithium, tert-butyllithium, sec-butyllithium, aryllithium such as phenyllithium.

Step 6B

In this Step, a 2-substituted imidazole compound of formula 6-2 may be prepared by the coupling of the above obtained compound of formula 6-1 with $R^{3b}B(OH)_2$ wherein $R^{3b}$ is as defined above in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene o-dichlorobenzene, nitrobenzene, pyridine, and xylene; halogenated hydrocarbons, such as methylene chloride, chloroform, carbon tetrachloride and dichloroethane; and ethers, such as diethyl ether, diisopropyl ether, dimethoxyethane (DME), tetrahydrofuran and dioxane. Of these solvents, we prefer the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to 150° C. The time required for the reaction may also vary widely, depending on many factors, notably the reaction temperature and the nature of the reagents and solvent employed. However, provided that the reaction may be effected under the preferred conditions outlined above, a period of from 1 minute to 2 days, more preferably from 20 minutes to a day, will usually suffice.

This reaction may be carried out in the presence a suitable catalyst. There is likewise no particular restriction on the nature of the catalysts used, and any catalysts commonly used in reactions of this type may equally be used here. Examples of such catalysts include: tetrakis (triphenylphosphine)-palladium, bis(triphenylphosphine) palladium(II) chloride, palladium(II) acetate, palladium(II) chloride, bisacetonitriledichloropalladium(0), bis (dibenzylideneacetone)palladium(0), tris (dibenzylideneacetone)dipalladium(0), [1,1'-bis (diphenylphosphino)ferrocene]palladium(II) dichloride, copper(0), copper(I) acetate, copper(I) bromide, copper(I) chloride, copper(I) iodide, copper(I) oxide, copper(II)

trifluoromethanesulfonate, copper(II) acetate, copper(II) bromide, copper(II) chloride, copper(II) iodide, copper(II) oxide, or copper(II) trifluoromethanesulfonate.

The reaction may be carried out in the presence of, or absence of a base. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine, dimethylaminopyridine; lithium hydroxide, sodium hydroxide, potassium hydroxide, barium hydroxide, sodium carbonate, potassium carbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, 1,8-diazabicyclo[5.4.0]undecan, picoline, 4-(N,N-dimethylamino)pyridine, triethylamine, tributylamine, diisopropylethylamine, N-methylmorphorine or N-methylpiperidine.

Step 6C

In this Step, a 2-substituted imidazole compound of formula 6-3 may be prepared by the deprotection of the compound of formula 6-2, prepared as described in Step 6B, according to known procedures such as those described in Protective Groups in Organic Synthesis edited by T. W. Greene et al. (John Wiley & Sons, 1991).

This reaction is essentially the same as and may be carried out in the same manner as and using the same reagents and reaction conditions as Step 5D in Scheme 5.

Step 6D

In this Step, the desired compound of formula (Ic), which is a compound of the present invention, may be prepared by the sulfonating the compound of formula 6-3, prepared as described in Step 6C.

This reaction is essentially the same as and may be carried out in the same manner as and using the same reagents and reaction conditions as Step 1D in Scheme 1 and Steps 3A and 3B in Scheme 3.

Compounds of formula $R^{3b}B(OH)_2$ may be a known compound or readily prepared by known methods (*Eur. J. Org. Chem.*, 20, 2000, 3483).

Scheme 7

This illustrates the alternative preparation of compounds of formula (Id) wherein $R^3$ represents $NH_2$.

Scheme 7

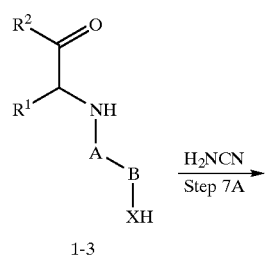

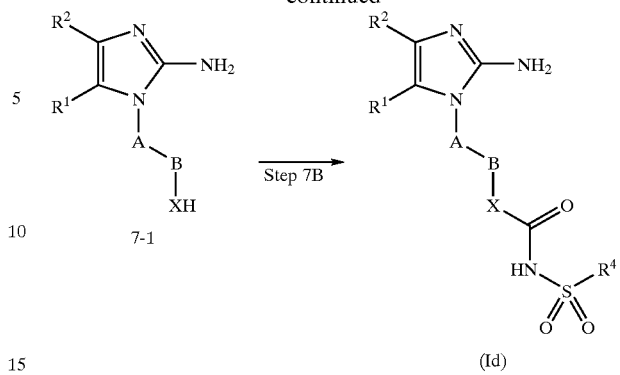

Step 7A

In this Step, a 2-aminoimidazole compound of formula 7-1 may be prepared from the 2-carbonyl-amine compound of formula 1-3, prepared as described in Step 1A in Scheme 1 by treating with aminitrile under conditions known to those skilled in the art (e.g., *Eur. J. Med. Chem. Chim. Ther.* 34, 225 (1999)).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: such as benzene, toluene, o-dichlorobenzene, nitrobenzene, pyridine, and xylene; halogenated hydrocarbons, such as methylene chloride, chloroform, carbon tetrachloride and dichloroethane; and ethers, such as diethyl ether, diisopropyl ether, tetrahydrofuran and dioxane; alcohols, such as methanol, ethanol, propanol, isopropanol and butanol; dimethylformamide (DMF), dimethylsulfoxide (DMSO). Of these solvents, we prefer the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the 150° C., The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 12 hours, will usually suffice.

Step 7B

In this Step, the desired compound of formula (Id), which is a compound of the present invention, may be prepared by the sulfonating the compound of formula 7-1, prepared as described in Step 7A.

This reaction is essentially the same as and may be carried out in the same manner as and using the same reagents and reaction conditions as Step 1D in Scheme 1 and Steps 3A and 3B in Scheme 3.

Scheme 8

This illustrates the alternative preparation of compounds of formula (I).

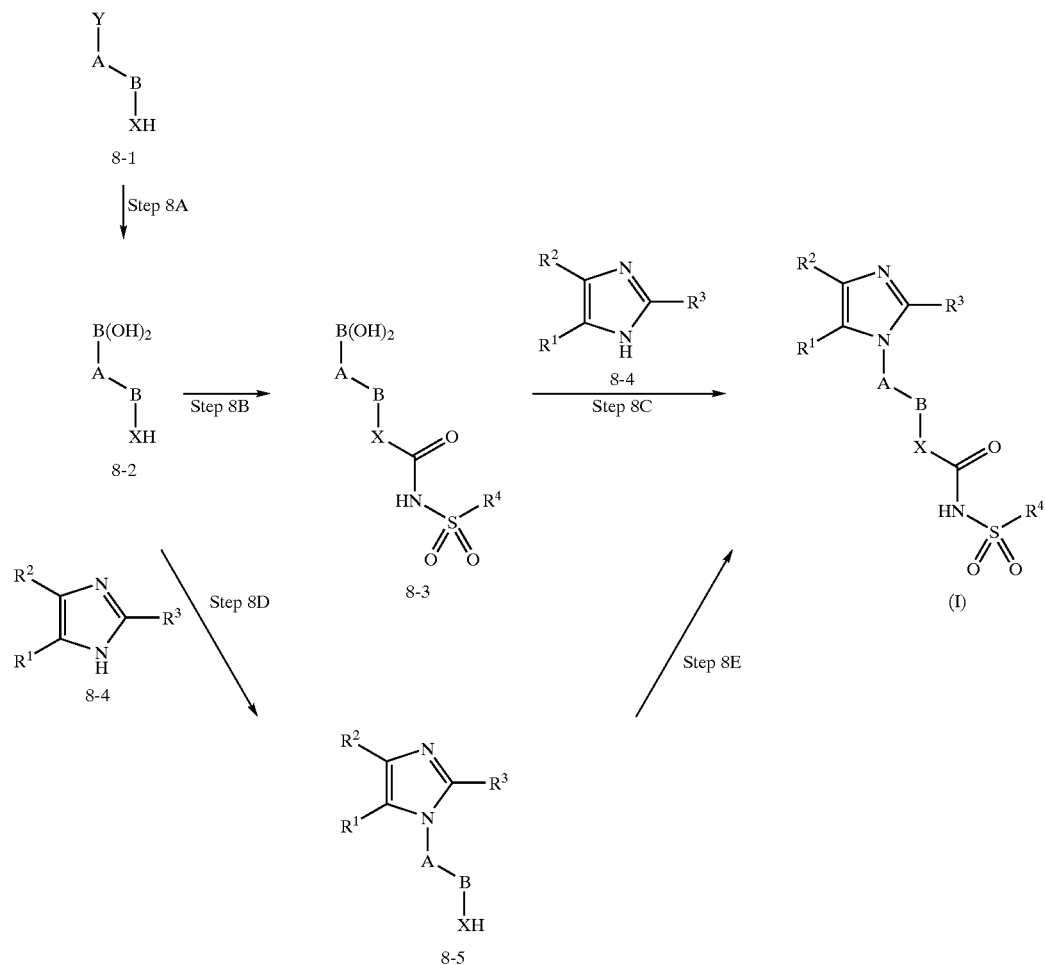

Scheme 8

Step 8A

In this Step, a boronic acid compound of formula 8-2 may be prepared from halo compound of formula 8-1 under conditions known to those skilled in the art.

For example, the halogen atom of the compound of formula 8-1 may be converted to the boronic acid using B(OR') wherein R' represents an alkyl group having from 1 to 6 carbon atoms in the presence or absence of a reaction inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; and ethers, such as diethyl ether, diisopropyl ether, tetrahydrofuran and dioxane. Of these solvents, we prefer the aliphatic hydrocarbons and ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 2 days, more preferably from 20 minutes to 60 hours, will usually suffice.

This reaction may be carried out in the presence of a base. There is likewise no particular restriction on the nature of the bases used, and any base commonly used in reactions of this type may equally be used here. Examples of such bases include: lithium, alkyllithium, such as n-butyllithium, tert-butyllithiun, sec-butyllithium and aryllithium such as phenylithium.

This reaction may be followed by an acidic hydrolysis in the presence of an acid to obtain the compound of formula 7-2. Example of suitable acids includes: hydrochloric acid, sulfuric acid, and hydrobromic acid.

Step 8B

In this Step, a sulfonamide compound of formula 8-3 may be prepared by the sulfonamidecarbonyl formation of the above obtained compound of formula 8-2 with suitable reagents.

This reaction is essentially the same as and may be carried out in the same manner as and using the same reagents and reaction conditions as Step 1C in Scheme 1 and Steps 3A and 3B in Scheme 3.

Step 8C

In this Step, the desired compound of formula (I), which is a compound of the present invention, may be prepared by the reacting the compound of formula 8-3, prepared as described in Step 8B with an imidazole compound formula 8-4 in an inert solvent under conditions known to those skilled in the art (e.g., *Tetrahedron Lett.*, 1998, 39, 2933 and *Tetrahedron Lett.*, 1998, 39, 2941).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, xylene, nitrobenzene, and pyridine; halogenated hydrocarbons, such as methylene chloride, chloroform, carbon tetrachloride and dichloroethane; ethers, such as diethyl ether, diisopropyl ether, tetrahydrofuran and dioxane; ethyl acetate, acetonitrile, N,N-dimethylformamide, dimethylsulfoxide. Of these solvents, we prefer the halogenated hydrocarbons and pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 10 day, more preferably from 20 minutes to 5 days, will usually suffice.

This reaction may be carried out in the presence a suitable catalyst. There is likewise no particular restriction on the nature of the catalysts used, and any catalysts commonly used in reactions of this type may equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride.

This reaction may be carried out in the presence of a suitable additive agent. Examples of such additive agents include: tiphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl or triphenylarsine.

This reaction may be carried out in the presence or absence of a base. There is likewise no particular restriction on the nature of the bases used, and any base commonly used in reactions of this type may equally be used here. Examples of such bases include: lithium hydroxide, sodium hydroxide, potassium hydroxide, barium hydroxide, sodium carbonate, potassium carbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, 1,8-diazabicyclo[5.4.0]undecan, picoline, 4-(N,N-dimethylamino)pyridine, triethylamine, tributylamine, diisopropylethylamine, N-methylmorphorine and N-methylpiperidine.

This reaction may be carried out in the presence or absence of a dehydrating reagent. There is likewise no particular restriction on the nature of the dehydrating reagents used, and any dehydrating reagents commonly used in reactions of this type may equally be used here. Examples of such dehydrating reagents include: molecular sieves.

Step 8D

In this Step, the desired compound of formula 8-5 may be prepared by the reacting the compound of formula 8-2, prepared as described in Step 8A with an imidazole compound formula 8-4 in an inert solvent.

This reaction is essentially the same as and may be carried out in the same manner as and using the same reagents and reaction conditions as Step 8C in Scheme 8.

Step 8E

In this Step, the desired compound of formula (I), which is a compound of the present invention, may be prepared from the compound of formula 8-5, prepared as described in Step 8D in an inert solvent.

This reaction is essentially the same as and may be carried out in the same manner as and using the same reagents and reaction conditions as Step 1D in Scheme 1 and Steps 3A and 3B in Scheme 3.

Compounds of formula 8-1 and 8-4 may be a known compound or readily prepared by known methods.

In the above Schemes, examples of suitable solvents include a mixture of any two or more of those solvents described in each Step.

Scheme 9

This illustrates the preparation of compound of formula (Ie) wherein $R^1$ and $R^2$ groups are optionally joined together to form an alkylene chain.

Scheme 9

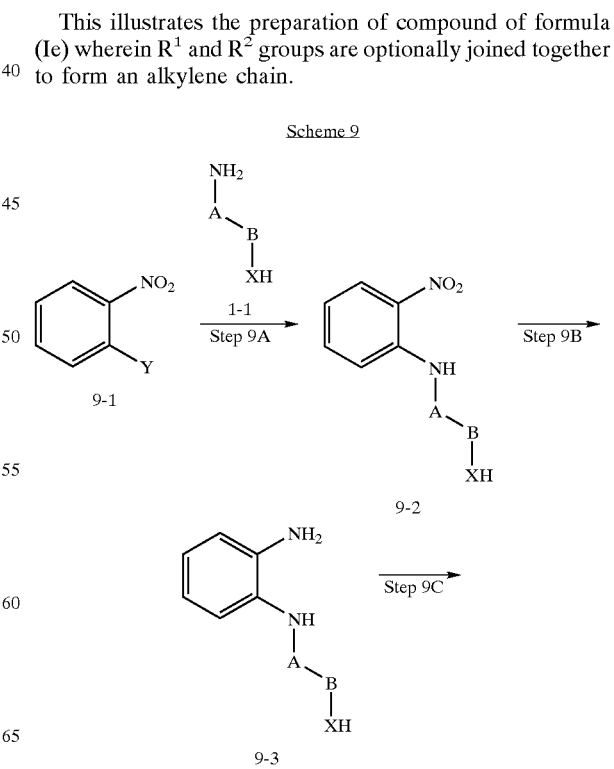

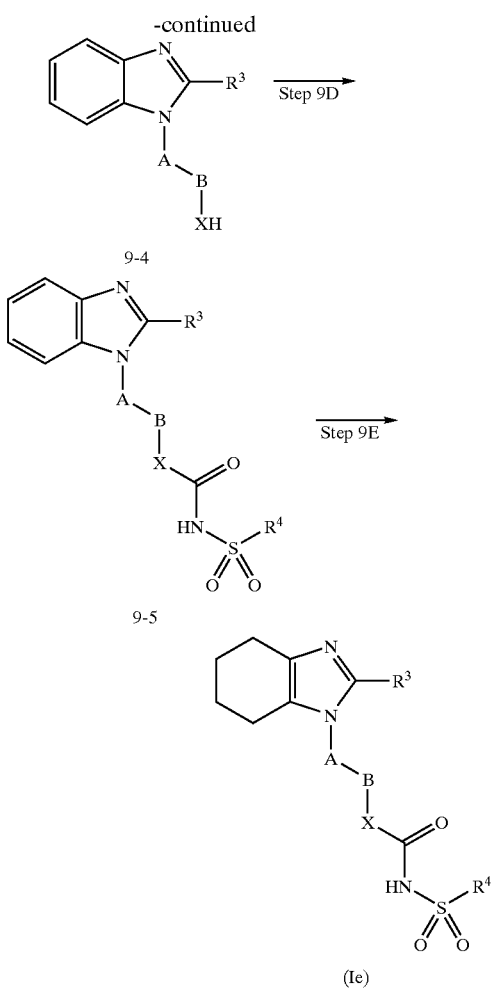

Step 9A

In this Step, an aminonitrobenzene compound of formula 9-2 may be prepared by the amination of a nitrobenzene compound of formula 9-1 with the compound of formula 1—1 in an inert solvent. The amination may be carried out in the absence or presence of a base in a reaction inert solvent or without solvent. A preferred base is selected from, for example, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine in the presence or absence of a reaction inert solvent. Preferred reaction inert solvents include, for example, benzene, toluene, xylene, o-dichlorobenzene, nitrobenzene, pyridine, dichloromethane, dichloroethane, tetrahydrofuran, dimethylformamide (DMF), dioxane, dimethylsulfoxide (DMSO) or mixtures thereof. Reaction temperatures are generally in the range of −100 to 250° C., preferably in the range of 0 to 150° C. Reaction times are, in general, from 1 minute to a day, preferably from 20 minutes to 5 hours.

Step 9B

In this Step, a diaminobenzene compound of formula 9-3 may be prepared by the reduction of an aminonitrobenzene compound of formula 9-2, prepared as described in Step 9A with a reducing agent in an inert solvent.

The reduction may be carried out in the presence of a suitable reducing agent in a reaction inert solvent or without solvent. A preferred reducing agent is selected from, for example, LiAlH$_4$, LiBH$_4$, Fe, Sn or Zn. When a reducing reagent is Fe, Sn or Zn, if desired, the reaction is carried out under acidic conditions in the presence of water. Preferred reaction inert solvents include, for example, methanol, ethanol, diglyme, benzene, toluene, xylene, o-dichlorobenzene, dichloromethane, dichloroethane, tetrahydrofuran, dioxane, or mixtures thereof. Reaction temperatures are generally in the range of −100 to 250° C., preferably in the range of 0 to 150° C. Reaction times are, in general, from 1 minute to a day, preferably from 20 minutes to 5 hours. The reduction may also be carried out under known hydrogenation conditions in the presence of a metal catalyst under hydrogen atmosphere or in the presence of hydrogen sources such as hydrazine or formic acid. If desired, the reaction is carried out under acidic conditions, for example, in the presence of hydrochloric acid or acetic acid. A preferred metal catalyst is selected from, for example, nickel catalysts such as Raney nickel, palladium catalysts such as Pd—C, platinum catalysts such as PtO$_2$, or ruthenium catalysts such as RuCl$_2$ (Ph$_3$P)$_3$. Preferred reaction inert solvents include, for example, methanol, ethanol, ethyl acetate, THF or mixtures thereof. The reaction may be carried out at a temperature in the range from of −100 to 150° C., preferably in the range of 0° C. to 100° C. Reaction times are, in general, from 1 minute to a day, preferably from 20 minutes to 5 hours.

Step 9C

In this Step, an imidazole compound of formula 9-4 may be prepared by the cyclization of the diaminobenzene compound of formula 9-3, prepared as described in Step 9B under conditions known to those skilled in the art.

The compound of formula 9-3 may be cyclized to form a benzimidazole or imidazopyridine ring by any synthetic procedure applicable to structure-related compounds known to those skilled in the art (for example, see Grimmett, M. R. Imidazoles and Their Benzo Derivatives: (iii) Synthesis and Applications. In *Comprehensive Heterocyclic Chemistry*, Kevin T. Potts, Eds.; Pergamon Press Ltd.: Oxford, UK, 1984; Vol. 5, pp457–498., Grimmett, M. R. Imidazoles. In *Comprehensive Heterocyclic Chemistry II*, Ichiro Shinkai, Eds.; Elsevier Science Ltd.: Oxford, UK, 1996; Vol. 3, pp77–220., Townsend L. B; Wise D. S. Bicyclo 5–6 Systems: Three Heteroatoms 2:1. In *Comprehensive Heterocyclic Chemistry II*, Christopher A. Ramsden, Eds.; Elsevier Science Ltd.: Oxford, UK, 1996; Vol. 7, pp283–349). For example, the compound of formula 9-3 is reacted with an appropriate cyclizing reagent to give the compound of formula 9-4 in a reaction inert solvent in the presence or absence of a coupling reagent. If desired, this reaction may be catalyzed by an acid such as para-toluenesulfonic acid or camphorsulfonic acid. Suitable cyclizing reagents include, for example, a carboxylic acid, an amino carboxylic acid, an acid anhydride (e.g., acetic anhydride, isobutyric anhydride, benzoic anhydride, isonicotinic anhydride and the like), a formamidine (e.g., formamidine alkylate such as formamidine acetate), an alkyl carbonyl halide (e.g., a cycloalkyl carbonyl halide, bicyclic or bicyclic-heterocyclic-carbonyl halide, spirocarbocyclic- or spiro-heterocyclic-carbonyl halide), an aryl or an aryl alkyl carbonyl halide (e.g., phenylacethyl halide), an heteroaryl carboxylic acid (e.g., a piperidinyl carboxylic acid compound), trialkyl orthoformate (e.g., triethyl orthoformate), and the like. Suitable reaction inert solvents include, for example, benzene, toluene, xylene, o-dichlorobenzene, nitrobenzene, dichloromethane, dichloroethane, tetrahydrofuran (THF), dimethylformamide (DMF), dioxane, dimethylsulfoxide (DMSO) or mixtures thereof. Suitable coupling reagents are those typically used in peptide synthesis including, for example, dicyclohexylcarbodiimide (DCC), diisopropylcarbodiimide (DIPC), 1-ethyl-3-(3-dimethylaminopropyl) carbodiimide (WSC), benzotriazole-1-yloxy-tris (dimethylamino)phosphonium hexafluorophosphate (BOP), diphenylphosphorylazide (DPPA), or the like. The reaction may be carried out at a temperature in the range from of −100° C. to 250° C., preferably in the range of 0° C. to the reflux temperature. Reaction times are, in general, from 1 minute to a few days, preferably from 30 minutes to 48 hours.

Step 9D

In this Step, a sulfonamidecarbonyl compound of formula 9-5 may be prepared by the sulfonating the compound of formula 9-4, prepared as described in Step 9C.

This reaction is essentially the same as and may be carried out in the same manner as and using the same reagents and reaction conditions as Step 1D in Scheme 1 and Steps 3A and 3B in Scheme 3.

Step 9E

In this Step, the desired compound of formula (Ie), which is a compound of the present invention, may be prepared by the reduction the compound of formula 9-5, prepared as described in Step 9D.

This reaction is essentially the same as and may be carried out in the same manner as and using the same reagents and reaction conditions as Step 1D in Scheme 1 and Steps 3A and 3B in Scheme 3.

The reduction may be carried out under known hydrogenation conditions in the presence of a metal catalyst under hydrogen atmosphere or in the presence of hydrogen sources such as hydrazine or formic acid. If desired, the reaction is carried out under acidic conditions, for example, in the presence of hydrochloric acid or acetic acid. A preferred metal catalyst is selected from, for example, nickel catalysts such as Raney nickel, platinum catalysts such as $PtO_2$, or ruthenium catalysts such as $RuCl_2$ $(Ph_3P)_3$, rhodium catalysts such as Rh—C. Preferred reaction inert solvents include, for example, methanol, ethanol, ethyl acetate, THF or mixtures thereof. The reaction may be carried out at a temperature in the range from of −100 to 150° C., preferably in the range of 0° C. to 100° C. Reaction times are, in general, from 1 minute to a day, preferably from 20 minutes to 5 hours. If necessary, this reduction may be carried out under the adequate pressure in the range from about 0.5 to 10 kg/cm$^2$, preferably in the range from 1 to 6 kg/cm$^2$.

This reaction may be carried out in the presence or absence of an acid catalyst. Examples of suitable acids include: hydrochloric acid, acetic acid, sulfuric acid, nitric acid, methanesulfonic acid, benzenesulfonic acid, and p-toluenesulfonic acid.

Compounds of formula 9-1 may be a known compound or readily prepared by known methods.

In the above Schemes from 1 to 9, examples of suitable solvents include a mixture of any two or more of those solvents described in each Step.

The optically active compounds of this invention can be prepared by several methods. For example, the optically active compounds of this invention may be obtained by chromatographic separation, enzymatic resolution or fractional crystallization from the final compounds.

Several cycloalkylene amide compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, pharmaceutically acceptable esters of said compounds and pharmaceutically acceptable salts of said compounds, of said esters or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deuterium, i.e., $^2H$, can afford therapeutic advantage resulting from greater metabolic stability, for example increased in vivo half-life or reduced dosage requirement and, hence, may be preferred in some circumstances. Isotopically labeled compounds of formula (I) of this invention and prodrugs thereof can generally be prepared by carrying out the procedure disclosed in above-disclosed Schemes and/or Examples and Preparations below, by submitting a readily available isotopically labeled reagent for a non-isotopically labeled reagent.

The present invention includes acid addition and base salt forms of the compounds (I).

Certain compounds of the present invention are capable of forming pharmaceutically acceptable non-toxic cations. Pharmaceutically acceptable non-toxic cation of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine (i.e., N-benzyl-2-phenyletylamine), benzathine (i.e., N,N-dibenzylethylenediamine), choline, diolamine (i.e., diethanolamine), ethylenediamine, glucosamine, glycine, guanidine, guanine, meglumine(i.e., N-methylglucamine), nicotinamide, olamine(i.e., ethanolamine), ornithine, procaine, proline, pyridoxine, serine, tyrosine, valine and tromethamine(i.e., tris or tris (hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, (i.e., 1,2-ethanedisulfontate), estolate (i.e., laurylsulfate), gluceptate (i.e., gluscoheptonate), gluconate, 3-hydroxy-2-naphthoate, xionofoate (i.e., 1-hydrroxy-2-naphthoate), isethionate, (i.e., 2-hydroxyethanesulfonate), mucaten (i.e., galactarate), 2-naphsylate (i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1.1'-methylene-bis-(2-hydroxy-3-naphthoate). The acid addition salts can be prepared by conventional procedures.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compounds of formula (I) in which one or both of L and W include hydroxy groups by making an ester of the hydroxy group. When only one of L and W includes hydroxy group, only mono-ester are possible. When both L and W include hydroxy, mono- and di-esters (which can be the same or different) can be made. Typical esters are simple alkanoate esters, such as acetate, propionate, butyrate, etc. In addition, when L or W includes a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

When the compounds of the formula (I) of this invention may form solvates such as hydrates, such solvates are included within the scope of this invention.

Also, the compounds of formula (I) may be expected more effective therapeutic effects with being co-administered with a COX-2 selective NSAID.

Further, the present invention also encompasses a combination, including a pharmaceutical composition, for the treatment of inflammation, rheumatoid arthritis, pain, common cold, osteoarthritis, neuropathic pain, brain tumor, diuresis, or the like, which comprises a therapeutically effective amount of a compound of formula (I) or salt or ester thereof and a COX-2 selective NSAID.

The compounds of the invention may advantageously be employed in combination with one or more other therapeutic ingredients selected from, a COX-2 selective, COX-1 selective or non-selective NSAIDs, opioids, anticonvulsants, antidepressants, local anesthetics, disease-modifying anti-rheumatoid drugs, or steroid.

The combination with a COX-2 selective NSAID is particularly favored for use in the prophylaxis and treatment of pain and arthritis. Examples of a, COX-2 selective NSAID are nimesulide, celecoxib, rofecoxib and valdecoxib.

The compounds of Formula (I) have been found to possess an activity as prostaglandin $E_2$ receptor antagonist, preferably as $EP_4$ receptor antagonist. Preferably, these compounds are useful as an analgesic, anti-inflammatory, diuretic, and the like, in mammalian subjects, especially humans in need of such agents. The affinity, antagonist activities and analgesic activity can be demonstrated by the following tests respectively.

Method for Assessing Biological Activities
In Vitro Assays
Rat EP Receptor Cell Membrane Binding Assay:
Stable Expression of Rat EP1, 2, 3 and 4 Receptors in the Human Embryonic Kidney (HEK293) Cell Line The cDNA clones of rat EP1, 2, 3 and 4 receptors are obtained by polymerase chain reaction (PCR) from rat kidney or heart cDNA libraries (Clontech). Human embryonic kidney cells (HEK 293) are stably transfected with expression vectors for rat EP1, 2, 3 and 4 receptors in according to the method described in the article; the journal of biological chemistry vol. 271 No.39, pp23642–23645.
Preparation of Membrane Fraction:

The EP1, 2, 3 and 4 transfectant are grown in Dulbecco's modified Eagle's medium containing 10% fetal calf serum, 100 U/ml penicillin, 100 µg/ml streptomycin and 600 µg/ml G418 (selection medium) at 37° C. in a humidified atmosphere of 5% $CO_2$ in air. For the membrane preparation, cells are harvested with phosphate buffered saline (PBS) and centrifuged at 400×g for 5 min. The pellet is suspended with child (4° C.) PBS containing 1 mom Pefabloc (4-(2-aminoethyl)-benzenesulfonyl fluoride (AEBSF)), 10 µM Phosphoramidon, 1 µM Pepstatin A, 10 µM Elastatinal, 100 µM Antipain. Cells are lysed with ultrasonic cell disrupter for 20-sec sonication. Then cell mixtures are centrifuged at 45,000×g for 30 minutes. The pellet is resuspended in assay buffer (10 mM 2-morpholinoeth-anesulfonic acid (MES)-KOH, 1 mM etylenediamine tetra-acetic acid (EDTA), 10 mM $MgCl_2$, pH 6.0 ), and protein concentration is determined by Bradford method (Bio-Rad assay). This membrane preparation is stored at −80° C. freezer until use for binding assay.
Binding Assay:
Membrane Binding Assay

[$^3$H]-$PGE_2$ membrane binding assays are performed in the reaction mixture of 10 mM MES/KOH (pH6.0), 10 mM $MgCl_2$, 1 mM EDTA, 1 nM [$^3$H]-$PGE_2$ (Amersham TRK431, 164Ci/mmol), 2~10 µg of protein from membrane fraction (rat EP1, 2, 3 and 4/HEK293 transfectant) and test compound (total volume is 0.1 ml in 96 well polypropylene plate). Incubation is conducted for 60 min at room temperature prior to separation of the bound and free radioligand by rapid filtration through glass fiber filters (Printed Filtermat B, 1205–404, glass fiber, double thickness, size 102×258 mm, Wallac inc., presoaked in 0.2% polyethylenimine). Filters are washed with assay buffer and the residual [$^3$H]-$PGE_2$ bound to the filter is determined by liquid scintillation counter (1205 Betaplate™). Specific binding is defined as the difference between total binding and nonspecific binding which is determined in the presence of 10 µM $PGE_2$.
cAMP Assay in Rat $EP_4$ Transfectant HEK293 cells expressing rat $EP_4$ receptors (r$EP_4$ cells) are maintained in DMEM containing 10% FCS and 600 µg/ml geneticin. For harvesting r$EP_4$ cells, culture medium is aspirated and cells in 75 $cm^2$ flask are washed with 10 ml of phosphate buffered saline (PBS). Another 10 ml of PBS is added to the cells and incubated for 20 min at room temperature. Rat $EP_4$ cells are harvested by pipetting and centrifuged at 300 g for 4 min. Cells are resuspended in DMEM without neutral red at a density of 5×10$^5$ cells/ml. The cells (70 µl) are mixed with 70 µl of DMEM (without neutral red) containing 2 mM IBMX (PDE inhibitor), 1 nM PGE$_2$ and test compounds in PCR-tubes, and incubated at 37° C. for 10 min. The reaction is stopped by heating at 100° C. for 10 min with thermal cycler. Concentration of cAMP in reaction mixtures is determined with SPA cAMP Kit (Amersham) according to the manufacture's instruction.
Reference: Eur. J. Pharmacol. 340 (1997) 227–241

In Vivo Assays

Carrageenan Induced Mechanical Hyperalgesia in Rats:

Male 4-week-old SD rats (Japan SLC) were fasted over night. Hyperalgesia was induced by intraplantar injection of λ-carrageenin (0.1 ml of 1% w/v suspension in saline, Zushikagaku). The test compounds (1 ml of 0.1% methylcellulose/100 g body weight) were given per orally at 5.5 hours after the carrageenin injection. The mechanical pain threshold was measured by analgesy meter (Ugo Basile) at 4, 5, 6.5 and 7.5 hours after the carrageenin injection and the change of pain threshold was calculated.
Reference: Randall L. O. & Selitto I. J., Arch. Int. Pharmacodyn. 111, 409–419, 1957

Prostaglandin E$_2$(PGE$_2$)-Induced Thermal Hyperalgesia in Rats:

Male 4-week-old SD rats (Japan SLC) were fasted over night. Hyperalgesia was induced by intraplantar injection of 100 ng of PGE$_2$ in 5% DMSO/saline (100 ul) into the right hindpaw of the rats. Animals were given orally or intravenously either vehicle (po: 0.1% methyl cellulose, iv: 10% DMSO/saline) or a test compound 15 or 5 min. prior to PGE$_2$ injection, respectively. Rats were placed in plastic cages of plantar test apparatus (Ugo Basile) and the mobile radiant heat source was focused on right hind paw of the rats. The thermal paw-withdrawal latency (sec.) was measured at 15 min after PGE$_2$ injection and the change in withdrawal threshold was calculated.
Reference: Hargreaves K. et al., Pain 32, 77–88, 1988.

Most of the compounds prepared in the working examples appearing hereafter demonstrate higher affinity for EP$_4$-receptors than for EP1, 2 and 3-receptors.

Pharmaceutically acceptable salts of the compounds of formula (I) include the acid addition and base salts (including disalts) thereof. Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, and tosylate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of

Pharmaceutical Salts: Properties, Selection, and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g.

D$_2$O, d$_6$-acetone, d$_6$-DMSO.

Also within the scope of the invention are clathrates, drug-host inclusion complexes wherein, in contrast to the aforementioned solvates, the drug and host are present in non-stoichiometric amounts. For a review of such complexes, see J Pharm Sci, 64 (8), 1269–1288 by Haleblian (August 1975).

Hereinafter all references to compounds of formula (I) include references to salts thereof and to solvates and clathrates of compounds of formula (I) and salts thereof. The invention includes all polymorphs of the compounds of formula (I) as hereinbefore defined.

Also within the scope of the invention are so-called "prodrugs" of the compounds of formula (I). Thus certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula (I), including compounds exhibiting more than one type of isomerism, and mixtures of one or more thereof. Cis/trans isomers may be separated by conventional techniques well known to those skilled in the art, for example, fractional crystallisation and chromatography. Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2$H and $^3$H, carbon, such as $^{13}$C and $^{14}$C, nitrogen, such as $^{15}$N, oxygen, such as $^{17}$O and $^{18}$O, phosphorus, such as $^{32}$P, sulphur, such as $^{35}$S, fluorine, such as $^{18}$F, and chlorine, such as $^{36}$Cl.

Substitution of the compounds of the invention with isotopes such as deuterium, i.e. $^2$H, may afford certain therapeutic advantages resulting from greater metabolic stability, for example, increased in vivo half-life or reduced dosage requirements, and hence may be preferred in some circumstances.

Certain isotopic variations of the compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Isotopic variations of the compounds of formula (I) can generally be prepared by conventional techniques known to those skilled in the art or by processes analogous to those described in the accompanying Examples and Preparations using appropriate isotopic variations of suitable reagents.

The compounds of formula (I) may be freeze-dried, spray-dried, or evaporatively dried to provide a solid plug, powder, or film of crystalline or amorphous material. Microwave or radio frequency drying may be used for this purpose.

The compounds of the invention may be administered alone or in combination with other drugs and will generally be administered as a formulation in association with one or more pharmaceutically acceptable excipients. The term "excipient" is used herein to describe any ingredient other than the compound of the invention. The choice of excipient will to a large extent depend on the particular mode of administration.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
| --- | --- |
| Compound of formula (I) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection. Formulations for topical administration may be formulated to be immediate and/or modified release. Modified release formulations include delayed-, sustained-, pulsed-, controlled dual-, targeted and programmed release. Thus compounds of the invention may be formulated in a more solid form for administration as an implanted depot providing long-term release of the active compound.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 10 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the compound of the invention, a suitable powder base such as lactose or starch and a performance modifier such as l-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff".

Formulations for inhaled/intranasal administration may be formulated to be immediate and/or modified release. Modified release formulations include delayed-, sustained-, pulsed-, controlled dual-, targeted and programmed release.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

The compounds of the invention may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be, delivered by iontophoresis.

Formulations for ocular/andial administration may be formulated to be immediate and/or modified release. Modified release formulations include delayed-, sustained-, pulsed-, controlled dual-, targeted, or programmed release.

Enabling Technologies

The compounds of the invention may be combined with soluble macromolecular entities such as cyclodextrin or polyethylene glycol-containing polymers to improve their solubility, dissolution rate, taste-masking, bioavailability and/or stability.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

The compounds of the invention can be administered via either the oral, parenteral or topical routes to mammals. In general, these compounds are most desirably administered to humans in doses ranging from 0.1 mg to 3000 mg, preferably from 1 mg to 500 mg, which may be administered in a single dose or in divided doses throughout the day, although variations will necessarily occur depending upon the weight and condition of the subject being treated, the disease state being treated and the particular route of administration chosen.

These dosages are based on an average human subject having a weight of about 65 to 70 kg. The physician will readily be able to determine doses for subjects whose weight falls outside this range, such as infants and the elderly.

For example, a dosage level that is in the range of from 0.01 mg to 10 mg per kg of body weight per day is most desirably employed for treatment of pain associated with inflammation.

EXAMPLES

The invention is illustrated in the following non-limiting examples in which, unless stated otherwise: all operations were carried out at room or ambient temperature, that is, in the range of 18–25° C; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Low-resolution mass spectral data (ESI) were obtained on a Quattro II (Micromass) mass spectrometer or a ZMD (Micromass). NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; hp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

Analytical condition for LC-MS(Waters LC-MS system (LC as 2690, ZMD as MS)): Column YMC CombiScreen basic 4.6 mm×50 mm, Flow rate 1 mL/min.; Mobile phase 20% MeOH/80% 0.1% $HCO_2H$ in $H_2O$ programmed over 5 min to 90% MeOH/10% 0.1% $HCO_2H$ in H2O. Hold for 5 min.; Wave length 220–400 nm. MS detector ApcI Cone 30 Volts.

Example 1

2-[4-(4-PHENYL-1H-IMIDAZOLE-1-YL)PHENYL]ETHYL (4-METHYLPHENYL)SULFONYLCARBAMATE

STEP. 1 4-(2-Hydroxyethyl)phenylboronic acid

To a stirred solution of 4-bromophenethylalcohol (5.00 g, 24.9 mmol) in tetrahydrofuran (80 mL) was added a solution of 1.5 M n-BuLi in hexane (39.8 mL, 59.7 mmol) at −78° C. over 30 min. After 1 hour, a solution of triisopropyl borate (8.61 mL, 37.3 mmol) in tetrahydrofuran (20 mL) was added slowly to the mixture at −78° C. The resulting mixture was warmed to room temperature, and treated with 2 M HCl (100 mL) for 1 hour. This mixture was extracted with dichloromethane and the combined organic phase was dried ($MgSO_4$) and concentrated under reduced pressure. The residue was purified by flash column chromatography on silica gel eluting with dichloromethane/methanol (20:1) to afford 2.61 g (63%) of the title compound as white solids: MS (ESI) m/z 165 [M−H]−, $^1$H-NMR ($CD_3OD$) δ 2.77 (2H, t, J=7.2 Hz), 3.70 (2H, t, J=7.2 Hz), 7.13–7.19 (2H, m), 7.48–7.64 (2H, m).

STEP 2. 4-{2-[({[(4-Methylphenyl)sulfonyl]amino}carbonyl)oxy]ethyl}phenylboronic acid 4-(2-Hydroxyethyl)phenylboronic acid (1.00 g, 6.02 mmol) was treated with pyridine (90 mL) and p-toluenesulfonylisocyanate (1.01 mL, 6.63 mmol) at room temperature for 2 hours. The mixture was poured into ice-2M HCl (200 mL) and extracted with ethyl acetate, and the organic fraction was dried ($MgSO_4$). After removal of solvent, the residue was purified flash column chromatography on silica gel eluting with dichloromethane/methanol to give 2.20 g (quant.) of the title compound as white solids: MS (ESI) m/z 381 [M+$NH_4$]+, 362 [M−H]−, $^1$H-NMR (DMSO-$d_6$) δ 2.40 (3H, s), 2.81 (2H, t, J=6.6 Hz), 4.18 (2H, t, J=6.6 Hz), 7.13 (2H, d, J=7.7 Hz), 7.40 (2H, d, J=8.6 Hz), 7.67–7.75 (2H, m), 7.97 (1H, s), 11.95 (1H, br).

STEP 3. 2-[4-(4-Phenyl-1H-imidazole-1-yl)phenyl[ethyl (4-methylphenyl)sulfonylcarbamate A mixture of 4-{2-[({[(4-Methylphenyl)sulfonyl]amino}carbonyl)oxy]ethyl}phenylboronic acid (100 mg, 0.28 mmol), 4-phenylimidazole (40 mg, 0.28 mmol), Copper(II) acetate (50 mg, 0.28 mmol), triethylamine (115 μL, 0.83 mmol), molecular sieves 4A (100 mg), and dichloromethane (4 mL) was stirred at room temperature for 1 week. Insoluble materials were removed by Celite pad, the filtrate was diluted with dichloromethane, and washed with water. The combined organic phase was dried ($MgSO_4$) and concentrated under reduced pressure. The residue was purified by TLC with dichloromethane/methanol (10:1) to afford 58 mg (46%) of the title compound as white solids: MS (ESI) m/z 462 [M+H]+, 460 [M−H]−, $^1$H-NMR (DMSO-$d_6$) δ 2.35 (3H, s), 2.88 (2H, t, J=6.5 Hz), 4.23 (2H, t, J=6.5 Hz), 7.22–7.43 (7H, m), 7.62 (2H, d, J=8.3 Hz), 7.74 (2H, d, J=8.3 Hz), 7.86 (2H, d, J=7.3 Hz), 8.26 (1H, s), 8.32 (1H, s).

Example 2

2-[4-(4,5-DIPHENYL-1H-IMIDAZOLE-1-YL)PHENYL]ETHYL (4-METHYLPHENYL)SULFONYLCARBAMATE

The title compound was prepared according to the procedure described in step 3 of Example 1 from 4,5-diphenylimidazole and 4-{2-[({[(4-Methylphenyl)sulfonyl]amino}carbonyl)oxy]ethyl}phenylboronic acid: MS (ESI) m/z 538 [M+H]+, 536 [M−H]−, $^1$H-NMR ($CDCl_3$) δ 2.43 (3H, s), 2.84 (2H, t, J=6.6 Hz), 4.22–4.28 (2H, m), 6.86–6.95 (2H, m), 7.03–7.08 (4H, m), 7.21–7.52 (10H, m), 7.73 (1H, s), 7.85–7.90 (2H, m).

Example 3

2-[4-(2-AMINO-5-METHYL-4-PHENYL-1H-IMIDAZOL-1-YL)PHENYL]ETHYL (4-METHYLPHENYL)SULFONYLCARBAMATE

STEP. 1 2-{[4-(2-hydroxyethyl)phenyl]amino}-1-phenyl-1-propanone

A mixture of 4-aminophenethyl alcohol (690 mg, 5.0 mmol), 2-bromopropiophenone (2.1 g, 10 mmol) potassium carbonate (690 mg, 5.0 mmol) in DMF (50 mL) was stirred at ambient temperature for 3 days. The mixture was partitioned between ethyl acetate and water. The combined organic phase was dried ($Na_2SO_4$) and concentrated under reduced pressure. The residue was purified by flash column chromatography on silica gel eluting with hexane/ethyl acetate (2:1) to afford the title compound quantitatively as yellow oil: $^1$H-NMR ($CDCl_3$) δ 1.49 (2H, d, J=6.9 Hz), 2.74 (2H, t, J=6.4 Hz), 3.79 (2H, t, J=6.4 Hz), 4.65 (1H, br), 5.11 (1H, m), 6.65 (2H, d, J=8.4 Hz), 7.05 (2H, d, J=8.6 Hz), 7.48–7.65 (3H, m), 8.03 (2H, d, J=7.2 Hz).

STEP 2. 2-[4-(2-amino-5-methyl-4-phenyl-1H-imidazol-1-yl)phenyl]ethanol

A mixture of 2-{[4-(2-hydroxyethyl)phenyl]amino}-1-phenyl-1-propanone (1.3 g, 5.0 mmol) and cyanamide (420 mg, 10 mmol) in ethanol (60 mL) was refluxed for 16 h. After removal of solvent, the residue was diluted with dichloromethane. The organic layer was washed with water, dried ($Na_2SO_4$) and concentrated under reduced pressure. The residue was purified by flash column chromatography on silica gel eluting with ethyl acetate/ethanol (10:1) to give 490 mg (33%) of the title compound as yellow solids: $^1$H-NMR ($CDCl_3$) δ 2.16 (3H, s), 2.96 (2H, t, J=5.6 Hz), 3.96 (2H, t, J=5.6 Hz), 4.24 (1H, br), 7.29–7.21 (2H, m), 7.46–7.38 (4H, m), 7.66–7.63 (2H, m).

STEP 3. 2-[4-(2-amino-5-methyl-4-phenyl-1H-imidazol-1-yl)phenyl]ethyl (4-methylphenyl)sulfonylcarbamate A mixture of 2-[4-(2-amino-5-methyl-4-phenyl-1H-imidazol-1-yl)phenyl]ethanol (100 mg, 0.34 mmol) and p-toluenesulfonylisocyanate (67 mg, 0.34 mmol) in dichloromethane (5 mL) was stirred at 0° C. for 10 min. It was washed with water and organic phase was dried over $Na_2SO_4$. After removal of solvent, the residue was purified by TLC with dichloromethane/methanol (10:1) to afford 8 mg (4.8%) of the title compound as white solids: MS (ESI) m/z 491 [M+H]$^+$, 489 [M−H]$^−$, $^1$H-NMR (CDCl$_3$) δ 2.27 (s, 3H), 2.87 (2H, t, J=5.9 Hz), 3.50 (3H, s), 4.24 (2H, t, J=5.7 Hz), 7.56–7.15 (11H, m), 7.83–7.80 (2H, m).

Example 4

2-[4-(2-AMINO-4,5-DIPHENYL-1H-IMIDAZOL-1-YL)PHENYL]ETHYL (4-METHYLPHENYL) SULFONYLCARBAMATE

STEP. 1 2-{[4-(2-hydroxyethyl)phenyl]amino}-1-phenyl-1-propanone

The title compound was prepared according to the procedure described in step 1 of Example 3 from desyl bromide: MS (ESI) m/z 331 [M]$^+$.

STEP 2. 2-[4-(2-amino-5-methyl-4-phenyl-1H-imidazol-1-yl)phenyl]ethanol

The title compound was prepared according to the procedure described in step 2 of Example 3 from 2-{[4-(2-hydroxyethyl)phenyl]amino}-1-phenyl-1-propanone: MS (ESI) m/z 355 [M]$^+$.

STEP 3. 2-[4-(2-amino-5-methyl-4-phenyl-1H-imidazol-1-yl)phenyl]ethyl (4-methylphenyl)sulfonylcarbamate The title compound was prepared according to the procedure described in step 3 of Example 3 from 2-[4-(2-amino-5-methyl-4-phenyl-1H-imidazol-1-yl)phenyl] ethanol: MS(ESI) m/z 553 [M+H]$^+$, 551 [M−H]$^−$, $^1$H-NMR (CDCl$_3$)δ 2.24 (3H, s), 2.66 (2H, t, J=6.9 Hz), 3.93 (2H, t, J=6.9 Hz), 5.94 (2H, br), 7.23–6.99 (6H, m), 7.60 (2H, d, J=8.2 Hz).

Example 5

2-[4-(2-ETHYL-4-PHENYL-1H-IMIDAZOLE-1-YL)PHENYL]ETHYL (4-METHYLPHENYL) SULFONYLCARBAMATE MONO-P-TOLUENESULFONATE SALT

STEP 1. 2-[4-(4-phenyl-1H-imidazol-1-yl)phenyl]ethanol

A mixture of 4-phenylimidazole (4.32 g, 30 mmol), Bromophenethyl alcohol (10.5 ml, 75 mmol), CuBr (10.4 g, 72 mmol) and Na$_2$CO$_3$ (3.8 g, 36 mmol) in 1,3-dimethyl-2-imidazolidinone (100 mL) was stirred at 180° C. for 36 h. After cooling, to the mixture was added 25% NH$_3$ aq. (50 mL). After 30 min, insoluble materials were removed by Celite filtration and washed with dichloromethane. The aqueous layer was extracted with dichloromethane. The organic phase was dried (MgSO$_4$) and concentrated under reduced pressure. To the residue was added diisopropylether (100 mL) and the flask was cooled to 0° C. Filtration of the diisopropylether gave 4.01 g of the title compound as colorless solid (51%): MS (ESI) m/z 265 [M+H]$^{+,}$ $^1$H-NMR (CDCl$_3$) δ 2.94 (2H, t, J=6.4 Hz), 3.93 (2H, br), 7.26–7.30 (2H, m), 7.35–7.44 (5H, m), 7.55 (1H, d, J=1.2 Hz), 7.82–7.86 (3H, m).

STEP 2. 1-[4-(2-{[tert-butyl(dimethyl)silyl]oxy}ethyl) phenyl]-4-phenyl-1H-imidazole To a stirred mixture of 2-[4-(4-phenyl-1H-imidazol-1-yl) phenyl]ethanol (5.36 g, 20.3 mmol) and imidazole (2.7 g, 40.6 mmol) in dichloromethane (100 mL) was added TBSCl (3.67 g, 24.3 mmol) at 0° C. and the reaction mixture was stirred at room temperature for 2 h. The volatile components were removed under reduced pressure, and the residue was purified by flash column chromatography on silica gel eluting with hexane/ethyl acetate (gradient elution from 5:1 to 2:1) to afford 5.6 g (73%) of the title compound as white solids: $^1$H-NMR (CDCl$_3$)δ0.00 (6H, s), 0.88 (9H, s), 2.87 (2H, t, J=6.6 Hz), 3.84 (2H, t, J=6.6 Hz), 7.26-7.30 (2H, m), 7.35–7.44 (5H, m), 7.54–7.55 (1H, m), 7.82 (1H, br), 7.85 (2H, d, J=1.2 Hz).

STEP 3. 1-[4-(2-{[tert-butyl(dimethyl)silyl]oxy}ethyl) phenyl]-2-ethyl-4-phenyl-1H-imidazole To a stirred solution of 1-[4-(2-{[tert-butyl(dimethyl) silyl]oxy}ethyl)phenyl]-4-phenyl-1H-imidazole (1.89 g, 5.0 mmol) in tetrahydrofuran (40 mL) was added a solution of 1.5 M n-BuLi in hexane (3.5 mL, 5.5 mmol) at −78° C. over 10 min. After 30 min, a solution of ethyl iodide (2.0 mL, 25.0 mmol) in tetrahydrofuran (10 mL) was added slowly to the mixture at −78° C. The resultant mixture was warmed to room temperature and stirred for 2 h. To the reaction mixture was added water and the volatile components were removed under reduced pressure. The aqueous phase was extracted with ethyl acetate and the combined organic phase was dried (MgSO$_4$) and concentrated under reduced pressure. Purification by flash column chromatography on silica gel eluting with hexane/ethyl acetate (gradient elution from 10:1 to 6:1) to afford 1.86 g (92%) of the title compound as pale yellow oil: MS (ESI) m/z 379 [M+H]$^{+1}$H-NMR (CDCl$_3$)δ0.00 (6H, s), 0.88 (9H, s), 1.26 (3H, t, J=7.5 Hz), 2.73 (2H, q, J=7.5 Hz), 2.91 (2H, t, J=6.6 Hz), 3.89 (2H, t, J=6.6 Hz), 7.22–7.28 (4H, m), 7.33–7.41 (4H, m), 7.81 (2H, d, J=7.1 Hz).

STEP 4. 2-[4-(2-ethyl-4-phenyl-1H-imidazol-1-yl)phenyl] ethanol

To a stirred solution of 1-[4-(2-{[tert-butyl(dimethyl) silyl]oxy}ethyl)phenyl]-2-ethyl-4-phenyl-1H-imidazole (1.84 g, 4.6 mmol) in tetrahydrofuran (25 mL) was added tetrabutylammonium fluoride (1.84 g, 6.9 mmol) at 0° C. After 1 h, the reaction mixture was partitioned between ethyl acetate and water. The aqueous phase was extracted with ethyl acetate and the combined organic phase was dried (MgSO$_4$) and concentrated under reduced pressure. Purification by flash column chromatography on silica gel eluting with hexane/ethyl acetate (gradient elution from 1:1 to 0:1) to afford 1.44 g (quant) of the title compound as colorless amorphous : MS (ESI) m/z 293 [M+H]$^{+1}$H-NMR (CDCl$_3$) δ1.26 (3H, t, J=7.5 Hz), 2.72 (2H, q, J=7.5 Hz), 2.95 (2H, t, J=6.6 Hz), 3.93 (2H, t, J=6.6 Hz), 7.22–7.28 (4H, m), 7.34–7.41 (4H, m), 7.79 (2H, d, J=7.1 Hz).

STEP 5. 2-[4-(2-ethyl-4-phenyl-1H-imidazole-1-yl)phenyl] ethyl (4-methylphenyl) sulfonylcarbamate To a stirred mixture of 2-[4-(2-ethyl-4-phenyl-1H-imidazol-1-yl)phenyl]ethanol (168 mg, 0.57 mmol) and triethylamine (87 mg, 0.86 mmol) in dichloromethane (6 mL) was added p-toluenesulfonyl isocyanate (124 mg, 0.63 mmol). The resulting mixture was stirred at room temperature for 3 h. After removal of solvent, the residue was purified by flash column chromatography on silica gel eluting with dichloromethane/methanol (20:1) to afford 1.10 g (56%) of the title compound as white solids: MS (ESI) m/z 490 [M+H]$^+$, 488 [M−H]$^−$, $^1$H-NMR (CDCl$_3$)δ7.92–7.89 (2H, m), 7.79–7.75 (2H, m), 7.38–7.12 (10H, m), 4.28 (2H, t, J=6.3 Hz), 2.87 (2H, t, J=6.3 Hz), 2.68 (2H, q, J=7.5 Hz), 2.44 (3H, s), 1.13 (3H, t, J=7.5 Hz).

The title compound was also prepared according to the procedure described in step 3 of Example 1 from 2-ethyl-4-phenylimidazole (J. Med. Chem., 1986, 29, 1065) and 4-{2-[({[(4-Methylphenyl)sulfonyl]amino}carbonyl)oxy] ethyl}phenylboronic acid:

STEP 6. 2-[4-(2-ethyl-4-phenyl-1H-imidazole-1-yl)phenyl] ethyl (4-methylphenyl)sulfonylcarbamate mono-p-toluenesulfonate salt A mixture of 2-[4-(2-ethyl-4-phenyl-1H-imidazole-1-yl) phenyl]ethyl (4-methylphenyl)sulfonylcarbamate (157 mg, 0.320 mmol), p-toluenesulfonic acid (61 mg, 0.320 mmol) in acetone (2 ml) was stirred at room temperature for 1 h. The reaction mixture was evaporated to afford the title compound as white solids: MS (ESI) m/z 490 [M+H]$^+$, 488 [M−H]$^−$.

Example 6

N-[({2-[4-(2-ETHYL-4-PHENYL-1H-IMIDAZOL-1-YL)PHENYL]ETHYL}AMINO)CARBONYL]-4-METHYLBENZENESULFONAMIDE MONO-P-TOLUENESULFONATE SALT

STEP 1.1-[4-(2-chloroethyl)phenyl]-2-ethyl-4-phenyl-1H-imidazole

To a stirred solution of 2-[4-(2-ethyl-4-phenyl-1H-imidazol-1-yl)phenyl]ethanol (step 4 of EXAMPLE 5, 1.13 g, 3.9 mmol) in dichloroethane (40 mL) was added thionyl chloride (0.375 mL, 4.63 mmol) and the resulting mixture was stirred at 80° C. After 0.5 h, the mixture was concentrated. The residue was dissolved in water and extracted with dichloromethane. The organic layer was washed with brine, dried (MgSO$_4$), and concentrated. Purification by flash column chromatography on silica gel eluting with hexane/ethyl acetate (2:1) to afford 1.04 g (87%) of the title compound as pale orange amorphous: $^1$H-NMR (CDCl$_3$)δ1.26 (2H, t, J=7.5 Hz), 2.72 (3H, q, J=7.5 Hz), 3.15 (2H, t, J=6.6 Hz), 3.78 (2H, t, J=6.6 Hz), 7.20–7.40 (9H, m), 7.79 (2H, dd, J=7.1, 1.3 Hz).

STEP 2. 1-[4-(2-azidoethyl)phenyl]-2-ethyl-4-phenyl-1H-imidazole

To a stirred solution of 1-[4-(2-chloroethyl)phenyl]-2-ethyl-4-phenyl-1H-imidazole (1.1 g, 3.4 mmol) and KI (566 mg, 3.4 mmol) in DMF (7 mL) was added sodium azide (443 mg, 6.8 mmol), and then the resulting mixture was stirred overnight at 100° C. The reaction mixture was poured into water, and extracted with ethyl acetate. The organic layer was washed with water and brine, then dried (MgSO$_4$). After removal of solvent, the crude product was purified by flash column chromatography on silica gel eluting with hexane/ethyl acetate (2:1) to afford 960 mg (89%) of the title compound as pale yellow amorphous: MS (ESI) m/z 318 [M+H]$^+$, $^1$H-NMR (CDCl$_3$)δ1.26 (2H, t, J=7.5 Hz), 2.72 (3H, q, J=7.7 Hz), 2.98 (2H, t, J=6.6 Hz), 3.59 (2H, t, J=6.6 Hz), 7.20–7.41 (9H, m), 7.79 (2H, dd, J=7.1, 1.3 Hz).

STEP 3. 2-[4-(2-ethyl-4-phenyl-1H-imidazol-1-yl)phenyl]ethylamine

To a solution of 1-[4-(2-azidoethyl)phenyl]-2-ethyl-4-phenyl-1H-imidazole (960 mg, 3.0 mmol) in methanol (50 mL) was added 10% Pd—C (50 mg). The resulting mixture was stirred for 4 h under hydrogen atmosphere. The mixture was filtered through a pad of Celite and the filtrate was concentrated to afford 900 mg (94%) of the title compound as colorless amorphous: MS (ESI) m/z 292 [M+H]$^{+1}$H-NMR (CDCl$_3$) δ1.26 (2H, t, J=7.5 Hz), 2.72 (3H, q, J=7.7 Hz), 2.84 (2H, t, J=6.6 Hz), 3.01–3.06 (2H, br), 7.20–7.40 (9H, m), 7.81 (2H, dd, J=7.1, 1.2 Hz).

STEP 4. N-[({2-[4-(2-ethyl-4-phenyl-1H-imidazol-1-yl)phenyl]ethyl}amino)carbonyl]-4-methylbenzenesulfonamide The title compound was prepared according to the procedure described in step 3 of Example 3 from 2-[4-(2-ethyl-4-phenyl-1H-imidazol-1-yl)phenyl]ethylamine. MS (ESI) m/z 489 [M+H]$^+$, 487 [M−H]$^−$, $^1$H-NMR (CDCl$_3$)δ1.24 (3H, t, J=7.7 Hz), 2.43 (3H, s), 2.72 (2H, q, J=7.5 Hz), 2.89 (2H, t, J=7.0 Hz), 3.54 (2H, t, J=7.0 Hz), 6.64 (1H, br), 7.24–7.40 (9H, m), 7.70 (2H, d, J=8.3 Hz), 7.79 (2H, d, J=6.9 Hz).

STEP 5. N-[({2-[4-(2-ethyl-4-phenyl-1H-imidazol-1-yl)phenyl]ethyl}amino)carbonyl]-4-methylbenzenesulfonamide mono-p-toluenesulfonate salt The title compound was prepared according to the procedure described in step 6 of Example 5 from N-[({2-[4-(2-ethyl-4-phenyl-1H-imidazol-1-yl)phenyl]ethyl}amino) carbonyl]-4-methylbenzenesulfonamide: MS (ESI) m/z 489 [M+H]$^+$, 487 [M−H]$^−$.

Example 7

2-[4-(2-ETHYL-4-PHENYL-1H-IMIDAZOL-1-YL)PHENYL]ETHYL (2-CHLOROPHENYL)SULFONYLCARBAMATE MONO-P-TOLUENESULFONATE SALT

STEP 1. 2-[4-(2-ethyl-4-phenyl-1H-imidazol-1-yl)phenyl] ethyl (2-chlorophenyl) sulfonylcarbamate The title compound was prepared according to the procedure described in step 3 of Example 3 from 2-[4-(2-ethyl-4-phenyl-1H-imidazol-1-yl)phenyl]ethanol and 2-chlorobenzensulfonyl isocyanate: MS (ESI) m/z 510 [M+H]$^+$, 508 [M−H]$^−$, $^1$H-NMR (DMSO-d$_6$) δ 1.17 (3H, t, J=7.3 Hz), 2.64 (2H, q, J=7.5 Hz), 2.80 (2H, t, J=6.8 Hz), 3.23 (2H, t, J=6.6 Hz), 7.19 (1H, t, J=7.3 Hz), 7.30–7.40 (6H, m), 7.74 (2H, d, J=9.9 Hz), 7.80 (2H, d, J=7.0 Hz), 7.97 (1H, br).

STEP 2. 2-[4-(2-ethyl-4-phenyl-1H-imidazol-1-yl)phenyl] ethyl (2-chlorophenyl) sulfonylcarbamate mono-p-toluenesulfonate salt The title compound was prepared according to the procedure described in step 6 of Example 5 from 2-[4-(2-ethyl-4-phenyl-1H-imidazol-1-yl)phenyl]ethyl (2-chlorophenyl) sulfonylcarbamate: MS (ESI) m/z 510 [M+H]$^+$, 508 [M−H]$^−$.

Example 8

2-CHLORO-N-[({2-[4-(2-ETHYL-4-PHENYL-1H-IMIDAZOL-1-YL)PHENYL]ETHYL}AMINO) CARBONYL]BENZENESULFONAMIDE MONO-P-TOLUENESULFONATE SALT

STEP 1. 2-chloro-N-[({2-[4-(2-ethyl-4-phenyl-1h-imidazol-1-yl)phenyl]ethyl}amino) carbonyl]benzenesulfonamide The title compound was prepared according to the procedure described in step 1 of Example 7 from 2-[4-(2-ethyl-4-phenyl-1H-imidazol-1-yl)phenyl]ethylamine and 2-chlorobenzensulfonyl isocyanate. MS (ESI) m/z 509 [M+H]$^+$, 507 [M−H]$^−$, $^1$H-NMR (DMSO-d$_6$) δ 1.17 (3H, t, J=7.3 Hz), 2.63 (2H, q, J=7.5 Hz), 2.73 (2H, t, J=7.1 Hz), 3.19–3.27 (2H, m), 6.45 (1H, br), 7.20 (1H, t, J=7.3 Hz), 7.30–7.41 (6H, m), 7.49–7.55 (1H, m), 7.61 (1H, br), 7.73 (1H, s), 7.80 (2H, d, J=8.4 Hz), 8.03 (1H, dd, J=7.31 Hz).

STEP 2. 2-chloro-N-[({2-[4-(2-ethyl-4-phenyl-1H-imidazol-1-yl)phenyl]ethyl}amino) carbonyl] benzenesulfonamide mono-p-toluenesulfonate salt The title compound was prepared according to the procedure described in step 6 of Example 5 from 2-chloro-N-[({2-[4-(2-ethyl-4-phenyl-1H-imidazol-1-yl)phenyl] ethyl}amino)carbonyl]benzenesulfonamide: MS (ESI) m/z 509 [M+H]$^+$, 507 [M−H]$^−$.

Example 9

2-[4-(2,4-DIPHENYL-1H-IMIDAZOL-1-YL) PHENYL]ETHYL (4-METHYLPHENYL) SULFONYLCARBAMATE MONO-P-TOLUENESULFONATE SALT

STEP 1. 1-[4-(2-{[tert-butyl(dimethyl)silyl]oxy}ethyl) phenyl]-2-iodo-4-phenyl-1H-imidazole To a stirred solution of 1-[4-(2-{[tert-butyl(dimethyl) silyl]oxy}ethyl)phenyl]-4-phenyl-1H-imidazole (750 mg, 2.0 mmol) in tetrahydrofuran (10 mL) was added a solution of 1.5 M n-BuLi in hexane (1.4 mL, 2.2 mmol) at −78° C. over 10 min. After 30 min, a solution of iodine (300 mg, 2.4 mmol) in tetrahydrofuran (10 mL) was added slowly to the mixture at −78° C. The resultant mixture was warmed to room temperature and stirred for 2 h. To the reaction mixture was added water (30 mL) and the volatile components were removed under reduced pressure. The aqueous phase was extracted with ethyl acetate (4×20 mL) and the combined organic phase was dried ($MgSO_4$) and concentrated under reduced pressure. Purification by flash column chromatography on silica gel eluting with hexane/ethyl acetate (gradient elution from 10:1 to 8:1) to afford 600 mg (60%) of the title compound as pale yellow oil: $^1$H-NMR (CDCl$_3$) δ 0.00 (6H, s), 0.88 (9H, s), 2.91 (2H, t, J=6.6 Hz), 3.89 (2H, t, J=6.6 Hz), 7.26–7.43 (7H, m), 7.46 (1H, m), 7.78–7.82 (2H, m).

STEP 2. 1-[4-(2-{[tert-butyl(dimethyl)silyl]oxy}ethyl) phenyl]-2,4-diphenyl-1H-imidazole A mixture of 1-[4-(2-{[tert-butyl(dimethyl)silyl] oxy}ethyl)phenyl]-2-iodo-4-phenyl-1H-imidazole (594 mg, 1.2 mmol), phenylboronic acid (287 mg, 2.4 mmol), 2M aqueous $K_2CO_3$ (3 mL) and bis(triphenylphosphine) palladium(II) chloride (165 mg, 0.24 mmol) in dimethoxyethane (10 mL) was heated at 90° C. for 16 h. After cooling, insoluble materials were removed by Celite pad and the filtrate was washed with 2N NaOH and brine, dried over ($MgSO_4$) and concentrated under reduced pressure. Purification by flash column chromatography on silica gel eluting with hexane/ethyl acetate (gradient elution from 30:1 to 10:1) to afford 390 mg (73%) of the title compound as pale yellow amorphous: $^1$H-NMR (CDCl$_3$)δ0.00 (6H, s), 0.89 (9H, s), 2.87 (2H, t, J=6.6 Hz), 3.86 (2H, t, J=6.6 Hz), 7.18–7.33 (7H, m), 7.39–7.52 (5H, m), 7.82 (1H, s), 7.89–7.93 (2H, m).

STEP 3. 2-[4-(2,4-diphenyl-1H-imidazol-1-yl)phenyl] ethanol

The title compound was prepared according to the procedure described in step 4 of Example 5 from 1-[4-(2-{[tert-butyl(dimethyl)silyl]oxy}ethyl)phenyl]-2,4-diphenyl-1H-imidazole. MS (ESI) m/z 341 [M+H]$^+$.

STEP 4. 2-[4-(2,4-diphenyl-1H-imidazol-1-yl)phenyl]ethyl (4-methylphenyl) sulfonylcarbamate The title compound was prepared according to the procedure described in step 3 of Example 3 from 2-[4-(2,4-diphenyl-1H-imidazol-1-yl)phenyl]ethanol. MS (ESI) m/z 489 [M+H]$^+$, 487 [M−H]$^-$, $^1$H-NMR (CDCl$_3$)δ2.43 (3H, s), 2.92 (2H, t, J=7.0 Hz), 3.54 (2H, t, J=7.0 Hz), 7.14–7.15 (3H, m), 7.24–7.34 (3H, m), 7.37–7.43 (5H, m), 7.80–7.90 (5H, m).

STEP 5. 2-[4-(2,4-diphenyl-1H-imidazol-1-yl)phenyl]ethyl (4-methylphenyl) sulfonylcarbamate mono-p-toluenesulfonate salt The title compound was prepared according to the procedure described in step 6 of Example 5 from 2-[4-(2,4-diphenyl-1H-imidazol-1-yl)phenyl]ethyl (4-methylphenyl) sulfonylcarbamate: MS (ESI) m/z 489 [M+H]$^+$, 487 [M−H]$^-$.

Example 10

2-[4-(2-ETHYL-5-METHYL-4-PHENYL-1H-IMIDAZOL-1-YL)PHENYL]ETHYL (4-METHYLPHENYL)SULFONYLCARBAMATE MONO-P-TOLUENESULFONATE SALT

STEP 1. 2-[4-(2-ethyl-5-methyl-4-phenyl-1H-imidazol-1-yl)phenyl]ethanol

To a stirred solution of 2-{[4-(2-hydroxyethyl)phenyl] amino}-1-phenyl-1-propanone (step 1 in EXAMPLE 3, 1.2 g, 4.5 mmol) in dichloromethane (10 mL) was added propionyl chloride (1.0 mL, 11.1 mmol) at ambient temperature. After 1 h, the reaction mixture was partitioned between ethyl acetate (30 mL) and water (10 mL). The aqueous phase was extracted with ethyl acetate (3×30 mL) and the combined organic phase was dried ($MgSO_4$) and concentrated under reduced pressure. To the residue was added ammonium acetate (7.7 g, 100 mmol) and AcOH (15 mL) and the mixture was heated at 100° C. for 10 h. After cooling, the mixture was diluted with MeOH and basified with 4N NaOH aq. at 0° C. After 30 min, volatile components were removed under reduced pressure. The aqueous phase was extracted with dichloromethane (4×20 mL) and the combined organic phase was dried ($MgSO_4$) and concentrated under reduced pressure. Purification by flash column chromatography on silica gel eluting with hexane/ethyl acetate (gradient elution from 1:1 to 1:2) to afford 0.32 g (23%) of the title compound as brown amorphous: $^1$H-NMR (CDCl$_3$)δ1.19 (3H, t, J=7.5 Hz), 2.16 (3H, s), 2.57 (3H, q, J=7.5 Hz), 2.97 (2H, t, J=6.4 Hz), 3.96 (2H, t, J=6.4 Hz), 7.19–7.26 (3H, m), 7.38–7.43 (4H, m), 7.79 (2H, dd, J=7.1, 1.4 Hz).

STEP 2. 2-[4-(2-ethyl-5-methyl-4-phenyl-1H-imidazol-1-yl)phenyl]ethyl (4-methylphenyl)sulfonylcarbamate The title compound was prepared according to the procedure described in step 3 of Example 3 from 2-[4-(2-ethyl-5-methyl-4-phenyl-1H-imidazol-1-yl)phenyl]ethanol: MS (ESI) m/z 504 [M+H]$^+$, 502 [M−H]$^-$, $^1$H-NMR (CDCl$_3$) δ1.15 (3H, t, J=7.5 Hz), 2.15 (3H, s), 2.44 (3H, s), 2.54 (2H, q, J=7.5 Hz), 2.94 (2H, t, J=6.6 Hz), 3.54 (2H, t, J=6.4 Hz), 7.12 (2H, d, J=8.3 Hz), 7.26–7.32 (5H, m), 7.40 (2H, t, J=7.7 Hz), 7.69 (2H, d, J=7.0 Hz), 7.87 (2H, d, J=8.4 Hz).

STEP 3. 2-[4-(2-ethyl-5-methyl-4-phenyl-1H-imidazol-1-yl)phenyl]ethyl (4-methylphenyl)sulfonylcarbamate mono-p-toluenesulfonate salt The title compound was prepared according to the procedure described in step 6 of Example 5 from 2-[4-(2-ethyl-5-methyl-4-phenyl-1H-imidazol-1-yl)phenyl]ethyl (4-methylphenyl)sulfonylcarbamate: MS (ESI) m/z 504 [M+H]$^+$, 502 [M−H]$^-$.

Example 11

2-[4-(2-ETHYL-4-PHENYL-1H-IMIDAZOL-1-YL) PHENYL]ETHYL (4-FLUOROPHENYL) SULFONYLCARBAMATE MONO-SODIUM SALT

STEP 1. 2-[4-(2-ethyl-4-phenyl-1H-imidazol-1-yl)phenyl] ethyl (4-fluorophenyl) sulfonylcarbamate The title compound was prepared according to the procedure described in step 3 of Example 3 from 2-[4-(2-ethyl-4-phenyl-1H-imidazol-1-yl)phenyl]ethanol (step 4 of example 5) and 4-fluorobenzensulfonyl isocyanate: MS (ESI) m/z 494 [M+H]$^+$, 492 [M−H]$^-$, $^1$H-NMR (DMSO-d$_6$) δ1.17 (3H, t, J=7.4 Hz), 2.65 (2H, q, J=7.5 Hz), 2.92 (2H, t, J=7.5 Hz), 4.24 (2H, t, J=7.5 Hz), 7.22 (2H, t, J=7.4 Hz), 7.34–7.49 (5H, m), 7.77–7.82 (4H, m), 7.91–7.97 (4H, m).

STEP 2. 2-[4-(2-ethyl-4-phenyl-1H-imidazol-1-yl)phenyl] ethyl (4-fluorophenyl) sulfonylcarbamate mono-sodium salt To a solution of 2-[4-(2-ethyl-4-phenyl-1H-imidazol-1-yl)phenyl]ethyl (4-fluorophenyl)sulfonylcarbamate (80 mg, 0.162 mmol) in methanol (5 mL) was added 2M aqueous NaOH (81 μL, 0.162 mmol). The resulting mixture was stirred at room temperature for 30 min and concentrated to afford the title compound as white solids: MS (ESI) m/z 494 [M +H]$^+$, 492 [M−H]$^-$.

Example 12

2-[4-(2-ETHYL-4-PHENYL-1H-IMIDAZOL-1-YL) PHENYL]ETHYL (4-CHLOROPHENYL) SULFONYLCARBAMATE MONO-SODIUM SALT

STEP 1. 2-[4-(2-ethyl-4-phenyl-1H-imidazol-1-yl)phenyl] ethyl (4-chlorophenyl) sulfonylcarbamate The title compound was prepared according to the procedure described in step 3 of Example 3 from 2-[4-(2-ethyl-4-phenyl-1H-imidazol-1-yl)phenyl]ethanol and 4-chlorobenzensulfonyl isocyanate: MS (ESI) m/z 510 [M+H]$^+$, 508 [M−H]$^-$, $^1$H-NMR (DMSO-d$_6$)δ1.17 (3H, t, J=7.4 Hz), 2.65 (2H, q, J=7.4 Hz), 2.92 (2H, t, J=6.8 Hz), 4.23 (2H, t, J=6.3 Hz), 7.23 (2H, t, J=7.2 Hz), 7.34–7.44 (5H, m), 7.68 (2H, d, J=8.7 Hz), 7.76–7.90 (6H, m).

STEP 2. 2-[4-(2-ethyl-4-phenyl-1H-imidazol-1-yl)phenyl] ethyl (4-chlorophenyl) sulfonylcarbamate mono-sodium salt The title compound was prepared according to the procedure described in step 2 of Example 11 from 2-[4-(2-ethyl-4-phenyl-1H-imidazol-1-yl)phenyl]ethyl (4-chlorophenyl)sulfonylcarbamate: MS (ESI) m/z 510 [M+H]$^+$, 508 [M−H]$^-$.

Example 13

2-[4-(2-BUTYL-4-PHENYL-1H-IMIDAZOL-1-YL) PHENYL]ETHYL (2-CHLOROPHENYL) SULFONYLCARBAMATE MONO-SODIUM SALT

STEP 1. 2-butyl-1-[4-(2-{[tert-butyl(dimethyl)silyl] oxy}ethyl)phenyl]-4-phenyl-1H-imidazole The title compound was prepared according to the procedure described in step 3 of Example 5 from 1-[4-(2-{[tert-butyl(dimethyl)silyl]oxy}ethyl)phenyl]-2-ethyl-4-phenyl-1H-imidazole and butyl iodide. MS (ESI) m/z 435 [M+H]$^+$.

STEP 2. 2-[4-(2-butyl-4-phenyl-1H-imidazol-1-yl)phenyl] ethanol

The title compound was prepared according to the procedure described in step 4 of Example 5 from 2-butyl-1-[4-(2-{[tert-butyl(dimethyl)silyl]oxy}ethyl)phenyl]-4-phenyl-1H-imidazole. MS (ESI) m/z 321 [M+H]$^+$.

STEP 3. 2-[4-(2-butyl-4-phenyl-1H-imidazol-1-yl)phenyl] ethyl (2-chlorophenyl) sulfonylcarbamate The title compound was prepared according to the procedure described in step 1 of Example 7 from 2-[4-(2-butyl-4-phenyl-1H-imidazol-1-yl)phenyl]ethanol. MS (ESI) m/z 538 [M+H]$^+$, 536 [M−H]$^-$, $^1$H-NMR (CDCl$_3$)δ0.84 (3H, t, J=7.3 Hz), 1.24–1.38 (2H, m), 1.57–1.68 (2H, m), 2.66–2.73 (2H, m), 2.92 (2H, t, J=6.8 Hz), 4.33 (2H, t, J=6.3 Hz), 7.23–7.28 (4H, m), 7.35–7.61 (6H, m), 7.80 (2H, d, J=8.0 Hz), 8.24 (2H, dd, J=7.9, 1.7 Hz).

STEP 4. 2-[4-(2-butyl-4-phenyl-1H-imidazol-1-yl)phenyl] ethyl (2-chlorophenyl) sulfonylcarbamate mono-sodium salt The title compound was prepared according to the procedure described in step 2 of Example 11 from 2-[4-(2-butyl-4-phenyl-1H-imidazol-1-yl)phenyl]ethyl (2-chlorophenyl)sulfonylcarbamate: MS (ESI) m/z 538[M+H]$^+$, 536 [M−H]$^-$.

Example 14

2-[4-(2-ISOBUTYL-4-PHENYL-1H-IMIDAZOL-1-YL)PHENYL]ETHYL (2-CHLOROPHENYL) SULFONYLCARBAMATE MONO-SODIUM SALT

STEP 1. 1-[4-(2-{[tert-butyl(dimethyl)silyl]oxy}ethyl) phenyl]-2-isobutyl-4-phenyl-1H-imidazole The title compound was prepared according to the procedure described in step 3 of Example 5 from 1-[4-(2-{[tert-butyl(dimethyl)silyl]oxy}ethyl)phenyl]-2-ethyl-4-phenyl-1H-imidazole and isobutyl iodide. MS (ESI) m/z 435 [M+H]$^+$.

STEP 2. 2-[4-(2-isobutyl-4-phenyl-1H-imidazol-1-yl) phenyl]ethanol

The title compound was prepared according to the procedure described in step 4 of Example 5 from 1-[4-(2-{[tert-butyl(dimethyl)silyl]oxy}ethyl)phenyl]-2-isobutyl-4-phenyl-1H-imidazole. MS (ESI) m/z 321 [M+H]$^+$.

STEP 3. 2-[4-(2-isobutyl-4-phenyl-1H-imidazol-1-yl) phenyl]ethyl (2-chlorophenyl) sulfonylcarbamate The title compound was prepared according to the procedure described in step 1 of Example 7 from 2-[4-(2-isobutyl-4-phenyl-1H-imidazol-1-yl)phenyl]ethanol. MS (ESI) m/z 538 [M+H]$^+$, 536 [M−H]$^-$, $^1$H-NMR (CDCl$_3$) δ0.85 (6H, d, J=6.6 Hz), 2.00–2.12 (1H, m), 2.59 (2H, d, J=7.3 Hz), 2.94 (2H, t, J=6.8 Hz), 4.33 (2H, t, J=6.8 Hz), 7.23–7.28 (4H, m), 7.35–7.61 (6H, m), 7.80 (2H, d, J=7.0 Hz), 8.24 (2H, dd, J=7.9, 1.7 Hz).

STEP 4. 2-[4-(2-isobutyl-4-phenyl-1H-imidazol-1-yl) phenyl]ethyl (2-chlorophenyl) sulfonylcarbamate mono-sodium salt The title compound was prepared according to the procedure described in step 2 of Example 11 from 2-[4-(2-isobutyl-4-phenyl-1H-imidazol-1-yl)phenyl]ethyl (2-chlorophenyl)sulfonylcarbamate: MS (ESI) m/z 538[M+H]$^+$, 536 [M−H]$^-$.

Example 15

2-[4-(2-ISOPROPYL-4-PHENYL-1H-IMIDAZOL-1-YL)PHENYL]ETHYL (2-CHLOROPHENYL) SULFONYLCARBAMATE MONO-SODIUM SALT

STEP 1. 2-{[4-(2-hydroxyethyl)phenyl]amino}-1-phenylethanone

The title compound was prepared according to the procedure described in step 1 of Example 3 from 2-bromoacetophenone. MS (ESI) m/z 256 [M+H]$^+$.

STEP 2. 2-[4-(2-isopropyl-4-phenyl-1H-imidazol-1-yl) phenyl]ethanol

The title compound was prepared according to the procedure described in step 1 of Example 10 from 2-{4-(2-hydroxyethyl)phenyl]amino}-1-phenylethanone and isobutyryl chloride. MS (EI) m/z 306 [M]$^+$.

STEP 3. 2-[4-(2-isopropyl-4-phenyl-1H-imidazol-1-yl) phenyl]ethyl (2-chlorophenyl) sulfonylcarbamate The title compound was prepared according to the procedure described in step 1 of Example 7 from 2-[4-(2-isopropyl-4-phenyl-1H-imidazol-1-yl)phenyl]ethanol. MS (ESI) m/z 524 [M+H]$^+$, 522 [M−H]$^-$, $^1$H-NMR (CDCl$_3$) δ1.30 (6H, d, J=7.0 Hz), 2.96 (2H, t, J=6.8 Hz), 4.34 (2H, t, J=6.8 Hz), 7.23–7.28 (4H, m), 7.35–7.61 (6H, m), 7.80 (2H, d, J=7.1 Hz), 8.24 (2H, dd, J=7.9, 1.5 Hz).

STEP 4. 2-[4-(2-isopropyl-4-phenyl-1H-imidazol-1-yl) phenyl]ethyl (2-chlorophenyl) sulfonylcarbamate mono-sodium salt The title compound was prepared according to the procedure described in step 2 of Example 11 from 2-[4-(2- isopropyl-4-phenyl-1H-imidazol-1-yl)phenyl]ethyl (2-chlorophenyl)sulfonylcarbamate: MS (ESI) m/z 524 [M+H]+, 522 [M–H]−.

Example 16

2-{4-[2-ETHYL-4-(4-FLUOROPHENYL)-1H-IMIDAZOL-1-YL]PHENYL]ETHYL (2-CHLOROPHENYL)SULFONYLCARBAMATE MONO-SODIUM SALT

STEP 1. 1-(4-fluorophenyl)-2-{[4-(2-hydroxyethyl)phenyl]amino}ethanone

The title compound was prepared according to the procedure described in step 1 of Example 3 from 4'-fluoro-2-bromoacetophenone. MS (EI) m/z 273 [M]+.

STEP 2. 2-{4-[2-ethyl-4-(4-fluorophenyl)-1H-imidazol-1-yl]phenyl}ethanol

The title compound was prepared according to the procedure described in step 1 of Example 10 from 1-(4-fluorophenyl)-2-{[4-(2-hydroxyethyl)phenyl]amino}ethanone. MS (EI) m/z 310 [M]+.

STEP 3. 2-{4-[2-ethyl-4-(4-fluorophenyl)-1H-imidazol-1-yl]phenyl}ethyl (2-chlorophenyl)sulfonylcarbamate The title compound was prepared according to the procedure described in step 1 of Example 7 from 2-{4-[2-ethyl-4-(4-fluorophenyl)-1H-imidazol-1-yl]phenyl}ethanol. MS (ESI) m/z 528 [M+H]+, 526 [M–H]−, $^1$H-NMR (DMSO-$d_6$) δ1.15 (3H, t, J=6.0 Hz), 2.64 (2H, q, J=6.0 Hz), 2.87 (2H, t, J=6.0 Hz), 4.21 (2H, t, J=6.3 Hz), 7.20 (2H, t, J=9.0 Hz), 7.33–7.41 (4H, m), 7.52–7.57 (1H, m), 7.66 (2H, d, J=6.0 Hz), 7.76 (1H, br, 7.80–7.84 (2H, m), 8.04 (1H, d, J=6.0 Hz).

STEP 4. 2-{4-[2-ethyl-4-(4-fluorophenyl)-1H-imidazol-1-yl]phenyl}ethyl (2-chlorophenyl)sulfonylcarbamate mono-sodium salt The title compound was prepared according to the procedure described in step 2 of Example 11 from 2-{4-[2-ethyl-4-(4-fluorophenyl)-1H-imidazol-1-yl]phenyl}ethyl (2-chlorophenyl)sulfonylcarbamate: MS (ESI) m/z 528 [M+H]+, 526 [M–H]−.

Example 17

2-CHLORO-N-[({2-[4-(2-ISOPROPYL-4-PHENYL-1H-IMIDAZOL-1-YL)PHENYL]ETHYL}AMINO)CARBONYL]BENZENESULFONAMIDE MONO-SODIUM SALT

STEP 1. 1-[4-(2-chloroethyl)phenyl]-2-isopropyl-4-phenyl-1H-imidazole

The title compound was prepared according to the procedure described in steps 1 of Example 6 from 2-[4-(2-isopropyl-4-phenyl-1H-imidazol-1-yl)phenyl]ethanol. $^1$H-NMR (CDCl$_3$)δ1.31 (6H, d, J=7.1 Hz), 2.92–3.07 (1H, m), 3.16 (2H, t, J=7.3 Hz), 3.79 (2H, t, J=7.3 Hz), 7.18–7.41 (7H, m), 7.77–7.84 (2H, m).

STEP 2. 1-[4-(2-azidoethyl)phenyl]-2-isopropyl-4-phenyl-1H-imidazole

The title compound was prepared according to the procedure described in steps 2 of Example 6 from 1-[4-(2-chloroethyl)phenyl]-2-isopropyl-4-phenyl-1H-imidazole. MS (EI) m/z 331 [M]+.

STEP 3. 2-[4-(2-isopropyl-4-phenyl-1H-imidazol-1-yl)phenyl]ethylamine

The title compound was prepared according to the procedure described in steps 3 of Example 6 from 1-[4-(2-azidoethyl)phenyl]-2-isopropyl-4-phenyl-1H-imidazole. MS (EI) m/z 305 [M]+.

STEP 4. 2-chloro-N-[({2-[4-(2-isopropyl-4-phenyl-1H-imidazol-1-yl)phenyl]ethyl}amino)carbonyl]benzenesulfonamide The title compound was prepared according to the procedure described in step 1 of Example 7 from 2-[4-(2-isopropyl-4-phenyl-1H-imidazol-1-yl)phenyl]ethylamine. MS (ESI) m/z 523 [M+H]+, 521 [M–H]−, $^1$H-NMR (CDCl$_3$) δ1.29 (6H, d, J=6.8 Hz), 2.85 (2H, t, J=7.1 Hz), 2.93–3.25 (1H, m), 3.51 (2H, m), 6.57 (1H, br), 7.18–7.30 (4H, m), 7.34–7.47 (4H, m), 7.59 (2H, d, J=3.8 Hz), 7.80 (2H, d, J=7.0 Hz), 8.00 (2H, d, J=7.7 Hz).

STEP 5. 2-chloro-N-[({2-[4-(2-isopropyl-4-phenyl-1H-imidazol-1-yl)phenyl]ethyl}amino)carbonyl]benzenesulfonamide mono-sodium salt The title compound was prepared according to the procedure described in step 2 of Example 11 from 2-chloro-N-[({2-[4-(2-isopropyl-4-phenyl-1H-imidazol-1-yl)phenyl]ethyl}amino)carbonyl]benzenesulfonamide: MS (ESI) m/z 523 [M+H]+, 521 [M–H]−.

Example 18

N-[({2-[4-(2-ETHYL-4-PHENYL-1H-IMIDAZOL-1-YL)PHENYL]ETHYL}AMINO)CARBONYL]-5-METHYL-2-PYRIDINESULFONAMIDE MONO-SODIUM SALT

STEP 1. phenyl 2-[4-(2-ethyl-4-phenyl-1H-imidazol-1-yl)phenyl]ethylcarbamate

To a stirred solution of 2-[4-(2-ethyl-4-phenyl-1H-imidazol-1-yl)phenyl]ethylamine (step 4 of EXAMPLE 3, 1.72 g, 5.9 mmol) and triethylamine (2.0 mL, 14.8 mmol) in dichloromethane (60 mL) was added phenyl chloroformate (900 μL, 7.0 mmol) at ambient temperature. After 1 h, the reaction mixture was partitioned between ethyl acetate (30 mL) and water (10 mL). The aqueous phase was extracted with ethyl acetate (3×30 mL) and the combined organic phase was dried (MgSO$_4$) and concentrated under reduced pressure. Purification by flash column chromatography on silica gel eluting with hexane/ethyl acetate (gradient elution from 3:1 to 1:1) to afford 2.0 g (83%) of the title compound as colorless amorphous: MS (ESI) m/z 412 [M+H]+, $^1$H-NMR (CDCl$_3$)δ1.27 (3H, d, J=7.5 Hz), 2.73 (2H, t, J=7.5 Hz), 2.99 (2H, t, J=7.1 Hz,) 3.59 (2H, t, J=7.0 Hz), 5.12 (1H, br), 7.12 (2H, d, J=7.5 Hz), 7.18–7.25 (2H, m), 7.29–7.41 (8H, m), 7.80 (2H, dd, J=8.3, 1.3 Hz).

STEP 2. N-[({2-[4-(2-ethyl-4-phenyl-1H-imidazol-1-yl)phenyl]ethyl}amino)carbonyl]-5-methyl-2-pyridinesulfonamide A mixture of phenyl 2-[4-(2-ethyl-4-phenyl-1H-imidazol-1-yl)phenyl]ethylcarbamate (203 mg, 0.50 mmol), 5-methylpyridine-2-sulfonamide (86 mg, 0.50 mmol) and DBU (82 μL, 0.55 mmol) in acetonitrile (5 mL) was stirred for overnight at ambient temperature. Then, the volatile components were removed by evaporation and the residue was dissolved in dichloromethane. The organic phase was washed with water, dried (MgSO$_4$) and concentrated. The residue was purified by TLC with dichloromethane/methanol (10:1) to afford 145 mg (60%) of the title compound as white solids: MS (ESI) m/z 490 [M+H]+, 488 [M–H]−, $^1$H-NMR (DMSO-$d_6$) δ 1.18 (3H, t, J=7.5 Hz), 2.37 (3H, s), 2.72–2.90 (4H, m), 3.23 (2H, q, J=6.0 Hz), 6.69 (1H, br), 7.40–7.59 (6H, m), 7.85–7.93 (4H, m), 8.24 (1H, s), 8.55 (1H, s).

STEP 3. N-[({2-[4-(2-ethyl-4-phenyl-1H-imidazol-1-yl)phenyl]ethyl}amino)carbonyl]-5-methyl-2-pyridinesulfonamide mono-sodium salt The title compound was prepared according to the procedure described in step 2 of Example 11 from N-[({2-[4-

(2-ethyl-4-phenyl-1H-imidazol-1-yl)phenyl]ethyl}amino) carbonyl]-5-methyl-2-pyridinesulfonamide: MS (ESI) m/z 490 [M+H]+, 488 [M−H]−.

Example 19

4-CHLORO-N-[({2-[4-(2-ETHYL-4-PHENYL-1H-IMIDAZOL-1-YL)PHENYL]ETHYL}AMINO) CARBONYL]BENZENESULFONAMIDE MONO-SODIUM SALT

STEP 1. 4-chloro-N-[({2-[4-(2-ethyl-4-phenyl-1H-imidazol-1-yl)phenyl]ethyl}amino)carbonyl]benzenesulfonamide The title compound was prepared according to the procedure described in step 2 of Example 18 from 2-[4-(2-ethyl-4-phenyl-1H-imidazol-1-yl)phenyl]ethylcarbamate and 4-chlorobenzenesulfonamide. MS (ESI) m/z 509 [M+H]+, 507 [M−H]−, $^1$H-NMR (DMSO-$d_6$) δ 1.14 (3H, t, J=7.5 Hz), 2.62 (2H, q, J=7.5 Hz), 2.72 (2H, t, J=7.1 Hz), 3.18–3.30 (2H, m), 6.60 (1H, t, J=5.7 Hz), 7.19 (1H, tt, J=7.3, 1.3 Hz), 7.28–7.38 (6H, m), 7.64–7.70 (2H, m), 7.76–7.80 (2H, m), 7.88 (2H, dt, J=11.2, 2.6 Hz).

STEP 2. 4-chloro-N-[({2-[4-(2-ethyl-4-phenyl-1H-imidazol-1-yl)phenyl]ethyl}amino)carbonyl]benzenesulfonamide mono-sodium salt The title compound was prepared according to the procedure described in step 2 of Example 11 from 4-chloro-N-[({2-[4-(2-ethyl-4-phenyl-1H-imidazol-1-yl)phenyl]ethyl}amino)carbonyl]benzenesulfonamide: MS (ESI) m/z 509 [M+H]+, 507 [M−H]−.

Example 20

4-FLUOLORO-N-[({2-[4-(2-ETHYL-4-PHENYL-1H-IMIDAZOL-1-YL)PHENYL]ETHYL}AMINO) CARBONYL]BENZENESULFONAMIDE MONO-SODIUM SALT

STEP 1. 4-fluoro-N-[({2-[4-(2-ethyl-4-phenyl-1H-imidazol-1-yl)phenyl]ethyl}amino)carbonyl]benzenesulfonamide The title compound was prepared according to the procedure described in step 2 of Example 18 from 2-[4-(2-ethyl-4-phenyl-1H-imidazol-1-yl)phenyl]ethylcarbamate and 4-fluorobenzenesulfonamide. MS (ESI) m/z 493 [M+H]+, 491 [M−H]−, $^1$H-NMR (CDCl$_3$) δ 1.23 (3H, t, J=7.5 Hz), 2.68 (2H, q, J=7.7 Hz), 2.87 (2H, t, J=7.0 Hz), 3.42–3.60 (2H, m), 6.46 (1H, br), 7.16–7.28 (7H, m), 7.37 (2H, t, J=7.3 Hz), 7.76 2H, d, J=7.1 Hz), 7.85–7.91 (2H, m).

STEP 2. 4-fluoro-N-[({2-[4-(2-ethyl-4-phenyl-1H-imidazol-1-yl)phenyl]ethyl}amino)carbonyl]benzenesulfonamide mono-sodium salt The title compound was prepared according to the procedure described in step 2 of Example 11 from 4-fluoro-N-[({2-[4-(2-ethyl-4-phenyl-1H-imidazol-1-yl)phenyl]ethyl}amino)carbonyl]benzenesulfonamide: MS (ESI) m/z 493 [M+H]+, 491 [M−H]−.

Example 21

4-CYANO-N-[({2-[4-(2-ETHYL-4-PHENYL-1H-IMIDAZOL-1-YL)PHENYL]ETHYL}AMINO) CARBONYL]BENZENESULFONAMIDE MONO-SODIUM SALT

STEP 1. 4-cyano-N-[({2-[4-(2-ethyl-4-phenyl-1H-imidazol-1-yl)phenyl]ethyl}amino)carbonyl]benzenesulfonamide The title compound was prepared according to the procedure described in step 2 of Example 18 from 2-[4-(2-ethyl-4-phenyl-1H-imidazol-1-yl)phenyl]ethylcarbamate and 4-cyanobenzenesulfonamide. MS (ESI) m/z 500 [M+H]+, 498 [M−H]−, $^1$H-NMR (DMSO-$d_6$) δ 1.14 (3H, t, J=7.5 Hz), 2.61 (2H, q, J=7.5 Hz), 2.72 (2H, t, J=7.1 Hz), 3.10–3.30 (2H, m), 6.60 (1H, br), 7.19 (1H, t, J=7.1 Hz), 7.28–7.39 (6H, m), 7.70 (1H, s), 7.78 (2H, d, J=7.1 Hz), 8.00–8.08 (4H, m).

STEP 2. 4-cyano-N-[({2-[4-(2-ethyl-4-phenyl-1H-imidazol-1-yl)phenyl]ethyl}amino) carbonyl]benzenesulfonamide mono-sodium salt The title compound was prepared according to the procedure described in step 2 of Example 11 from 4-cyano-N-[({2-[4-(2-ethyl-4-phenyl-1H-imidazol-1-yl)phenyl]ethyl}amino)carbonyl]benzenesulfonamide: MS (ESI) m/z 500 [M+H]+, 498 [M−H]−

Example 22

N-[({2-[4-(2-ETHYL-4-PHENYL-1H-IMIDAZOL-1-YL)PHENYL]ETHYL}AMINO)CARBONYL]-4-METHOXYBENZENESULFONAMIDE MONO-SODIUM SALT

STEP 1. 4-methoxy-N-[({2-[4-(2-ethyl-4-phenyl-1H-imidazol-1-yl)phenyl]ethyl}amino)carbonyl]benzenesulfonamide The title compound was prepared according to the procedure described in step 2 of Example 18 from 2-[4-(2-ethyl-4-phenyl-1H-imidazol-1-yl)phenyl]ethylcarbamate and 4-methoxybenzenesulfonamide. MS (ESI) m/z 505 [M+H]+, 503 [M−H]−, $^1$H-NMR (CDCl$_3$) δ 1.25 (3H, t, J=7.5 Hz), 2.72 (2H, q, J=7.5 Hz), 2.91 (2H, t, J=6.8 Hz), 3.40–3.55 (2H, m), 6.64 (1H, br), 6.96 (2H, d, J=9.0 Hz), 7.20–7.30 (5H, m), 7.38 (2H, t, J=7.3 Hz), 7.74 (2H, d, J=9.0 Hz), 7.79 (2H, d, J=8.4 Hz).

STEP 2. 4-methoxy-N-[({2-[4-(2-ethyl-4-phenyl-1H-imidazol-1-yl)phenyl]ethyl}amino)carbonyl]benzenesulfonamide mono-sodium salt The title compound was prepared according to the procedure described in step 2 of Example 11 from 4-methoxy-N-[({2-[4-(2-ethyl-4-phenyl-1H-imidazol-1-yl)phenyl]ethyl}amino)carbonyl]benzenesulfonamide: MS (ESI) m/z 505 [M+H]+, 503 [M−H].

Example 23

N-[({2-[4-(2-ETHYL-4-PHENYL-1H-IMIDAZOL-1-YL)PHENYL]ETHYL}AMINO)CARBONYL]-2-FLUOROBENZENESULFONAMIDE MONO-SODIUM SALT

STEP 1. 2-fluoro-N-[({2-[4-(2-ethyl-4-phenyl-1H-imidazol-1-yl)phenyl]ethyl}amino)carbonyl]benzenesulfonamide The title compound was prepared according to the procedure described in step 2 of Example 18 from 2-[4-(2-ethyl-4-phenyl-1H-imidazol-1-yl)phenyl]ethylcarbamate and 2-fluorobenzenesulfonamide. MS (ESI) n/z 500 [M+H]+, 498 [M−H]−, $^1$H-NMR (CDCl$_3$) δ 1.23 (3H, t, J=6.0 Hz), 2.71 (2H, q, J=6.0 Hz), 2.84 (2H, t, J=6.0 Hz), 3.44–3.52 (2H, m), 6.58 (1H, br), 7.18–7.30 (7H, m), 7.37 (2H, t, J=9.0 Hz), 7.59–7.65 (1H, m), 7.78 (2H, d, J=6.0 Hz), 7.84–7.90 (2H, m).

STEP 2. 2-fluoro-N-[({2-[4-(2-ethyl-4-phenyl-1H-imidazol-1-yl)phenyl]ethyl}amino)carbonyl]benzenesulfonamide mono-sodium salt The title compound was prepared according to the procedure described in step 2 of Example 11 from 2-fluoro-N-[({2-[4-(2-ethyl-4-phenyl-1H-imidazol-1-yl)phenyl]ethyl}amino)carbonyl]benzenesulfonamide: MS (ESI) m/z 500 [M+H]+, 498 [M−H].

Example 24

2-[4-(2-tert-BUTYL-4-PHENYL-1H-IMIDAZOL-1-YL)PHENYL]ETHYL (2-CHLOROPHENYL) SULFONYLCARBAMATE MONO-SODIUM SALT STEP 1. 2-[4-(2-tert-butyl-4-phenyl-1H-imidazol-1-yl)phenyl]ethanol The title compound was prepared according to the procedure described in step 1 of Example 10 from 2-{[4-(2-hydroxyethyl)phenyl]amino}-1-phenylethanone and trimethylacetyl chloride. MS (EI) m/z 320 [M]$^+$.

STEP 2. 2-[4-(2-tert-butyl-4-phenyl-1H-imidazol-1-yl)phenyl]ethyl (2-chlorophenyl)sulfonylcarbamate The title compound was prepared according to the procedure described in step 1 of Example 7 from 2-[4-(2-tert-butyl-4-phenyl-1H-imidazol-1-yl)phenyl]ethanol. MS (ESI) m/z 538 [M+H]$^+$, 536 [M−H]$^−$, $^1$H-NMR (CDCl$_3$) δ 1.27 (9H, s), 2.96 (2H, t, J=6.8 Hz), 4.33 (2H, t, J=7.0 Hz), 7.09 (1H, s), 7.18–7.39 (7H, m), 7.44–7.61 (3H, m), 7.78 (2H, dd, J=8.4, 1.5 Hz), 8.23 (1H, dd, J=8.3, 1.5 Hz).

STEP 3. 2-[4-(2-tert-butyl-4-phenyl-1H-imidazol-1-yl)phenyl]ethyl (2-chlorophenyl)sulfonylcarbamate mono-sodium salt The title compound was prepared according to the procedure described in step 2 of Example 11 from 2-[4-(2-tert-butyl-4-phenyl-1H-imidazol-1-yl)phenyl]ethyl (2-chlorophenyl)sulfonylcarbamate: MS (ESI) m/z 538 [M+H]$^+$, 536 [M−H].

Example 25

4-CHLORO-N-{[(2-{4-[4-PHENYL-2-(TRIFLUOROMETHYL)-1H-IMIDAZOL-1-YL]PHENYL}ETHYL)AMINO] CARBONYL}BENZENESULFONAMIDE MONO-SODIUM SALT

STEP 1. 2-{4-[4-phenyl-2-(trifluoromethyl)-1H-imidazol-1-yl]phenyl}ethanol

The title compound was prepared according to the procedure described in step 1 of Example 10 from 2-{[4-(2-hydroxyethyl)phenyl]amino}-1-phenylethanone and trifluoroacetic anhydride. MS (EI) m/z 332 [M]$^+$.

STEP 2. 2-{4-[4-phenyl-2-(trifluoromethyl)-1H-imidazol-1-yl]phenyl}ethyl methanesulfonate To a stirred solution of 2-{4-[4-phenyl-2-(trifluoromethyl)-1H-imidazol-1-yl]phenyl}ethanol (450 mg, 1.35 mmol) and triethylamine (377 μL, 2.70 mmol) in dichloromethane (13 mL) was added methanesulfonyl chloride (126 μL, 1.62 mmol) at ambient temperature. After 1 h, the reaction mixture was partitioned between dichloromethane and water. The aqueous phase was extracted with dichloromethane (3×10 mL) and the combined organic phase was dried (MgSO$_4$) and concentrated under reduced pressure to give the title compound as a brown oil (quant.). MS (EI) m/z 410 [M]$^+$.

STEP 3. 1-[4-(2-azidoethyl)phenyl]-4-phenyl-2-(trifluoromethyl)-1H-imidazole

A mixture of 2-{4-[4-phenyl-2-(trifluoromethyl)-1H-imidazol-1-yl]phenyl}ethyl methanesulfonate and sodium azide (175 mg, 2.70 mmol) and potassium iodide (224 mg, 1.35 mmol) in DMF (7 mL) was heated at 100° C. for overnight. After cooling, the reaction mixture was partitioned between ethyl acetate (20 mL) and water (10 mL). The aqueous phase was extracted with ethyl acetate (3×10 mL) and the combined organic phase was dried (MgSO$_4$) and concentrated under reduced pressure. Purification by flash column chromatography on silica gel eluting with hexane/ethyl acetate (gradient elution from 10:1 to 4:1) to afford 450 mg (93%) of the title compound as colorless amorphous: MS (EI) m/z 357 [M]$^+$.

STEP 4. 2-{4-[4-phenyl-2-(trifluoromethyl)-1H-imidazol-1-yl]phenyl}ethanamine

The title compound was prepared according to the procedure described in step 3 of Example 5 from 1-[4-(2-azidoethyl)phenyl]-4-phenyl-2-(trifluoromethyl)-1H-imidazole. MS (EI) m/z 331 [M]$^+$.

STEP 5. phenyl 2-{4-[4-phenyl-2-(trifluoromethyl)-1H-imidazol-1-yl]phenyl}ethylcarbamate The title compound was prepared according to the procedure described in step 1 of Example 18 from 2-{4-[4-phenyl-2-(trifluoromethyl)-1H-imidazol-1-yl]phenyl}ethanamine. MS (ESI) m/z 452 [M+H]$^+$.

STEP 6. 4-chloro-N-{[(2-{4-[4-phenyl-2-(trifluoromethyl)-1H-imidazol-1-yl]phenyl}ethyl)amino]carbonyl}benzenesulfonamide The title compound was prepared according to the procedure described in step 2 of Example 18 from phenyl 2-{4-[4-phenyl-2-(trifluoromethyl)-1H-imidazol-1-yl]phenyl}ethylcarbamate and 4-chlorobenzenesulfonamide. MS (ESI) m/z 549 [M+H]$^+$, 547 [M−H]$^−$, $^1$H-NMR (CDCl$_3$) δ 2.92 (2H, t, J=7.3 Hz), 3.40–3.60 (2H, m), 6.60 (1H, br), 7.24–7.45 (7H, m), 7.51 (2H, d, J=9.0 Hz), 7.77 (2H, d, J=9.0 Hz), 7.82 (2H, d, J=6.9 Hz).

STEP 7. 4-chloro-N-{[(2-{4-[4-phenyl-2-(trifluoromethyl)-1H-imidazol-1-yl]phenyl}ethyl)amino]carbonyl}benzenesulfonamide mono-sodium salt The title compound was prepared according to the procedure described in step 2 of Example 11 from 4-chloro-N-{[(2-{4-[4-phenyl-2-(trifluoromethyl)-1H-imidazol-1-yl]phenyl}ethyl)amino]carbonyl}benzenesulfonamide: MS (ESI) m/z 549 [M+H]$^+$, 547 [M−H].

Example 26

2-CHLORO-N-{[(2-{4-[2-ETHYL-4-(4-FLUOROPHENYL)-1H-IMIDAZOL-1-YL]PHENYL}ETHYL)AMINO] CARBONYL}BENZENESULFONAMIDE MONO-SODIUM SALT

STEP 1. 2-naphthylmethyl propanimidothioate hydrobromide

A mixture of propiothioamide (892 mg, 10 mmol) and 2-bromophenylnaphthalene (2.21 g, 10 mmol) in chloroform (80 mL) was heated at 80° C. for 2 h. After cooling, the mixture was poured into diethyl ether (100 mL) and cooled at 0° C. for 1 h. The resulting precipitate was corrected by filtration and dried under reduced pressure to give 2.85 g (92%) of the title compound as a colorless powder. MS (ESI) m/z 230 [M+H]$^+$.

STEP 2. tert-butyl 2-(4-aminophenyl)ethylcarbamate

To a stirred solution of 2-(4-aminophenyl)ethylamine (10.0 g, 73.4 mmol) in tetrahydrofuran (150 mL) was added di-t-butyl dicarbonate (16.0 g 73.4 mmol) in tetrahydrofuran (100 mL) at 0° C. Then, the mixture was stirred at ambient temperature for 1 h. The volatile components were removed by evaporation and the residue was dissolved in ethyl acetate. The organic phase was washed with water and dried (MgSO$_4$). Concentration of the organic solvent gave the 17.0 g (98%) of the title compound as a colorless powder. MS (ESI) m/z 237 [M+H]$^+$, $^1$H-NMR (CDCl$_3$) δ 1.43 (9H, s), 2.68 (2H, t, J=7.0 Hz), 3.26–3.38 (2H, m), 3.60 (2H, br), 4.53 (1H, br), 6.64 (2H, d, J=8.4 Hz), 6.97 (2H, d, J=8.3 Hz).

STEP 3. tert-butyl 2-[4-(propanimidoylamino)phenyl]ethylcarbamate

A mixture of tert-butyl 2-(4-aminophenyl)ethylcarbamate (709 mg, 3 mmol) and 2-naphthylmethyl propanimidothioate hydrobromide (930 mg, 3 mmol) in ethanol (10 mL) was stirred for overnight at ambient temperature. Then, the volatile components were removed by evaporation and the residue was partitioned between diethyl ether (10 mL) and water (10 mL). The aqueous phase was washed with diethyl ether (3×10 mL) and basified by NaOH to pH 10. The aqueous phase was extracted with chloroform (20×4) and the combined extract was dried ($MgSO_4$). Concentration of the organic solvent afforded 831 mg (95%) of the title compound as a colorless powder. MS (ESI) m/z 292 $[M+H]^+$.

STEP 4. tert-butyl 2-4-[2-ethyl-4-(4-fluorophenyl)-1H-imidazol-1-yl]phenyl}ethylcarbamate A mixture of tert-butyl 2-[4-(propanimidoylamino) phenyl]ethylcarbamate (831 mg, 2.9 mmol), 4'-fluoro-2-bromoacetophenone (928 mg, 4.3 mmol) and sodium bicarbonate (480 mg, 5.7 mmol) in 2-propanol (30 mL) was heated at 100° C. for overnight. After cooling, insoluble materials were removed by filtration and the filtrate was concentrated. Purification by flash column chromatography on silica gel eluting with hexane/ethyl acetate (gradient elution from 3:1 to 3:2) afforded 1.1 g (91%) of the title compound as colorless amorphous. MS (ESI) m/z 410 $[M+H]^+$.

STEP 5. phenyl 2-{4-[2-ethyl-4-(4-fluorophenyl)-1H-imidazol-1-yl]phenyl}ethylcarbamate A solution of tert-butyl 2-{4-[2-ethyl-4-(4-fluorophenyl)-1H-imidazol-1-yl]phenyl}ethylcarbamate (1.1 g, 2.6 mmol) in 10% HCl-MeOH (20 mL) was heated at 50° C. for 2 h. After cooling, the volatile components were removed by evaporation and the resulting amorphous was dried under reduced pressure. Then, the amorphous was suspended in dichloromethane at 0° C. To the cooled mixture was added triethylamine (1.4 mL, 10 mmol) and phenyl chloroformate (380 μL, 3.0 mmol). After 1 h, the reaction mixture was partitioned between ethyl acetate (30 mL) and water (10 mL). The aqueous phase was extracted with ethyl acetate (3×30 mL) and the combined organic phase was dried ($MgSO_4$) and concentrated under reduced pressure. Purification by flash column chromatography on silica gel eluting with hexane/ethyl acetate (gradient elution from 3:1 to 2:1) afforded 924 mg (85%) of the title compound as colorless amorphous. MS (ESI) m/z 430 $[M+H]^+$.

STEP 6. 2-chloro-N-{[(2-{4-[2-ethyl-4-(4-fluorophenyl)-1H-imidazol-1-yl]phenyl}ethyl)amino]carbonyl}benzenesulfonamide The title compound was prepared according to the procedure described in step 2 of Example 18 from phenyl 2-{4-[2-ethyl-4-(4-fluorophenyl)-1H-imidazol-1-yl]phenyl}ethylcarbamate and 2-chlorobenzenesulfonamide. MS (ESI) m/z 527 $[M+H]^+$, 525 $[M-H]^-$, $^1$H-NMR ($CDCl_3$) δ1.25 (3H, t, J=7.5 Hz), 2.71 (2H, q, J=7.5 Hz), 2.85 (2H, t, J=7.0 Hz), 3.47–3.54 (2H, m), 6.57 (1H, br), 7.07 (2H, t, J=8.8 Hz), 7.19 (1H, s), 7.26 (2H, s), 7.40–7.46 (1H, m), 7.57–7.61 (2H, m), 7.73–7.78 (2H, m), 8.00 (2H, d, J=7.5 Hz).

STEP 7. 2-chloro-N-{[(2-{4-[2-ethyl-4-(4-fluorophenyl)-1H-imidazol-1-yl]phenyl}ethyl)amino]carbonyl}benzenesulfonamide mono-sodium salt The title compound was prepared according to the procedure described in step 2 of Example 11 from 2-chloro-N-{[(2-{4-[2-ethyl-4-(4-fluorophenyl)-1H-imidazol-1 -yl] phenyl}ethyl)amino]carbonyl}benzenesulfonamide: MS (ESI) m/z 527 $[M+H]^+$, 525 $[M-H]^-$.

Example 27

4-CHLORO-N-{[(2-{4-[2-ETHYL-4-(4-FLUOROPHENYL)-1H-IMIDAZOL-1-YL]PHENYL}ETHYL)AMINO]CARBONYL}BENZENESULFONAMIDE MONO-SODIUM SALT

STEP 1. 4-chloro-N-{[(2-{4-[2-ethyl-4-(4-fluorophenyl)-1H-imidazol-1-yl]phenyl}ethyl)amino]carbonyl}benzenesulfonamide The title compound was prepared according to the procedure described in step 2 of Example 18 from phenyl 2-{4-[2-ethyl-4-(4-fluorophenyl)-1H-imidazol-1-yl]phenyl}ethylcarbamate and 4-chlorobenzenesulfonamide. MS (ESI) m/z 527 $[M+H]^+$, 525 $[M-H]^-$, $^1$H-NMR ($CDCl_3$) δ 1.24 (3H, t, J=7.5 Hz), 2.69 (2H, q, J=7.5 Hz), 2.83–2.90 (2H, m), 3.45–3.54 (2H, m), 6.50 (1H, br), 7.05 (2H, t, J=8.8 Hz), 7.18 (1H, s), 7.22–7.30 (2H, m), 7.42–7.52 (3H, m), 7.70–7.79 (4H, m).

STEP 2. 4-chloro-N-{[(2-{4-[2-ethyl-4-(4-fluorophenyl)-1H-imidazol-1-yl]phenyl}ethyl)amino]carbonyl}benzenesulfonamide mono-sodium salt The title compound was prepared according to the procedure described in step 2 of Example 11 from 4-chloro-N-{[(2-{4-[2-ethyl-4-(4-fluorophenyl)-1H-imidazol-1-yl] phenyl}ethyl)amino]carbonyl}benzenesulfonamide: MS (ESI) m/z 527 $[M+H]^+$, 525 $[M-H]^-$.

Example 28

2-CHLORO-N-{[(2-{4-[4-PHENYL-2-(TRIFLUOROMETHYL)-1H-IMIDAZOL-1-YL]PHENYL}ETHYL)AMINO]CARBONYL}BENZENESULFONAMIDE MONO-SODIUM SALT

STEP 1. 2-chloro-N-{[(2-{4-[4-phenyl-2-(trifluoromethyl)-1H-imidazol-1-yl]phenyl}ethyl)amino]carbonyl}benzenesulfonamide The title compound was prepared according to the procedure described in step 2 of Example 18 from phenyl 2-{4-[4-phenyl-2-(trifluoromethyl)-1H-imidazol-1-yl]phenyl}ethylcarbamate and 2-chlorobenzenesulfonamide. MS (ESI) m/z 549 $[M+H]^+$, 547 $[M-H]^-$, $^1$H-NMR ($CDCl_3$) δ 2.86 (2H, t, J=7.3 Hz), 3.48–3.55 (2H, m), 6.58 (1H, br), 7.25–7.28 (1H, m), 7.31–7.36 (3H, m), 7.25–7.28 (1H, m), 7.39–7.47 (4H, m), 7.58–7.61 (2H, m), 7.82 (2H, dd, J=8.4, 1.4 Hz), 8.00 (2H, d, J=7.5 Hz).

STEP 2. 2-chloro-N-{[(2-{4-[4-phenyl-2-(trifluoromethyl)-1H-imidazol-1-yl]phenyl}ethyl)amino]carbonyl}benzenesulfonamide mono-sodium salt The title compound was prepared according to the procedure described in step 2 of Example 11 from 2-chloro-N-{[(2-{4-[2-ethyl-4-(4-fluorophenyl)-1H-imidazol-1-yl] phenyl}ethyl)amino]carbonyl}benzenesulfonamide: MS (ESI) m/z 549 $[M+H]^+$, 547 $[M-H]^-$.

Example 29

4-CHLORO-N-{[(2-{4-[2-ETHYL-4-(2-PYRIDINYL)-1H-IMIDAZOL-1-YL]PHENYL}ETHYL)AMINO]CARBONYL}BENZENESULFONAMIDE MONO-SODIUM SALT

STEP 1. tert-butyl 2-{4-[2-ethyl-4-(2-pyridinyl)-1H-imidazol-1-yl]phenyl}ethylcarbamate The title compound was prepared according to the procedure described in step 4 of Example 26 from tert-butyl 2-[4-(propanimidoylamino)phenyl]ethylcarbamate and 2-bromo-1-(2-pyridinyl)ethanone hydrobromide (*J. Org. Chem.*, 1996, 61, 4623). MS (ESI) m/z 393 [M+H]$^+$.

STEP 2. phenyl 2-{4-[2-ethyl-4-(2-pyridinyl)-1H-imidazol-1-yl]phenyl}ethylcarbamate The title compound was prepared according to the procedure described in step 5 of Example 26 from tert-butyl 2-{4-[2-ethyl-4-(2-pyridinyl)-1H-imidazol-1-yl]phenyl}ethylcarbamate. MS (ESI) m/z 412 [M+H]$^+$.

STEP 3. 4-chloro-N-{[(2-{4-[2-ethyl-4-(2-pyridinyl)-1H-imidazol-1-yl]phenyl}ethyl)amino]carbonyl}benzenesulfonamide The title compound was prepared according to the procedure described in step 2 of Example 18 from phenyl 2-{4-[2-ethyl-4-(2-pyridinyl)-1H-imidazol-1-yl]phenyl}ethylcarbamate and 4-chlorobenzenesulfonamide. MS (ESI) m/z 510 [M+H]$^+$, 508 [M–H]$^-$, $^1$H-NMR (CDCl$_3$) □1.17 (3H, t, J=7.3 Hz), 2.65 (2H, q, J=7.7 Hz), 2.80–2.88 (2H, m), 3.42–3.55 (2H, m), 6.78 (1H, br), 7.15–7.28 (4H, m), 7.42 (2H, d, J=8.4 Hz), 7.58 (1H, s), 7.71 (1H, t, J=6.0 Hz), 7.80–7.89 (3H, m), 8.51 (1H, d, J=6.0 Hz).

STEP 4. 4-chloro-N-{[(2-{4-[2-ethyl-4-(2-pyridinyl)-1H-imidazol-1-yl]phenyl}ethyl)amino]carbonyl}benzenesulfonamide mono-sodium salt The title compound was prepared according to the procedure described in step 2 of Example 11 from 4-chloro-N-{[(2-{4-[2-ethyl-4-(2-pyridinyl)-1H-imidazol-1-yl]phenyl}ethyl)amino]carbonyl}benzenesulfonamide: MS (ESI) m/z 510 [M+H]$^+$, 508 [M–H].

Example 30

4-CHLORO-N-[({2-[4-(2-ISOPROPYL-4-PHENYL-1H-IMIDAZOL-1-YL)PHENYL]ETHYL}AMINO)CARBONYL]BENZENESULFONAMIDE MONO-SODIUM SALT

STEP 1. 4-chloro-N-[({2-[4-(2-isopropyl-4-phenyl-1H-imidazol-1-yl)phenyl]ethyl}amino)carbonyl]benzenesulfonamide The title compound was prepared according to the procedure described in step 1 of Example 12 from 2-[4-(2-isopropyl-4-phenyl-1H-imidazol-1-yl)phenyl]ethylamine. MS (ESI) m/z 523 [M+H]$^+$, 521 [M–H]$^-$, $^1$H-NMR (CDCl$_3$) δ1.29 (6H, d, J=6.8 Hz), 2.85 (2H, t, J=7.1 Hz), 2.93–3.25 (1H, m), 3.51 (2H, m), 6.57 (1H, br), 7.18–7.30 (4H, m), 7.34–7.47 (4H, m), 7.59 (2H, d, J=3.8 Hz), 7.80 (2H, d, J=7.0 Hz), 8.00 (2H, d J=7.7 Hz).

STEP 2. 4-chloro-N-[({2-[4-(2-isopropyl-4-phenyl-1H-imidazol-1-yl)phenyl]ethyl}amino)carbonyl]benzenesulfonamide mono-sodium salt The title compound was prepared according to the procedure described in step 2 of Example 11 from 4-chloro-N-[({2-[4-(2-isopropyl-4-phenyl-1H-imidazol-1-yl)phenyl]ethyl}amino)carbonyl]benzenesulfonamide. MS (ESI) m/z 523 [M+H]$^+$, 521 [M–H]$^-$.

Example 31

2-[4-(2-METHYL-4-PHENYL-1H-IMIDAZOL-1-YL)PHENYL]ETHYL (4-METHYLPHENYL)SULFONYLCARBAMATE MONO-SODIUM SALT

STEP 1. 1-[4-(2-{[tert-butyl(dimethyl)silyl]oxy}ethyl)phenyl]-2-methyl-4-phenyl-1H-imidazole The title compound was prepared according to the procedure described in step 3 of Example 5 from 1-[4-(2-{[tert-butyl(dimethyl)silyl]oxy}ethyl)phenyl]-4-phenyl-1H-imidazole and methyl iodide. MS (ESI) m/z 393 [M+H]$^+$.

STEP 2. 2-[4-(2-methyl-4-phenyl-1H-imidazol-1-yl)phenyl]ethanol

The title compound was prepared according to the procedure described in step 4 of Example 5 from 1-[4-(2-{[tert-butyl(dimethyl)silyl]oxy}ethyl)phenyl]-2-methyl-4-phenyl-1H-imidazole: MS (EI) m/z 278 [M]$^+$ $^1$H-NMR (CDCl$_3$) δ2.42 (3H, s), 2.94 (2H, t, J=6.4 Hz), 3.92 (2H, t, J=6.6 Hz), 7.27–7.30 (2H, m), 7.38–7.44 (4H, m), 7.54 (1H, d, J=1.2 Hz), 7.82-7.85 (3H, m)

STEP 3. 2-[4-(2-methyl-4-phenyl-1H-imidazol-1-yl)phenyl]ethyl (4-methylphenyl)sulfonylcarbamate The title compound was prepared according to the procedure described in step 3 of Example 3 from 2-[4-(2-methyl-4-phenyl-1H-imidazol-1-yl)phenyl]ethanol: MS (ESI) m/z 476 [M+H]$^+$, 474 [M–H]$^-$ $^1$H-NMR (CDCl$_3$) δ2.32 (3H, s), 2.43 (3H, s), 2.89 (2H, t, J=6.2 Hz), 4.30 (2H, t, J=6.1 Hz), 7.14 (2H, d, J=8.6 Hz), 7.20 (2H, d, J=8.6 Hz), 7.29–7.73 (4H, m), 7.75 (2H, d, J=7.1 Hz), 7.92 (2H, d, J=8.4 Hz)

STEP 4. 2-[4-(2-methyl-4-phenyl-1H-imidazol-1-yl)phenyl]ethyl (4-methylphenyl)sulfonylcarbamate mono-sodium salt The title compound was prepared according to the procedure described in step 2 of Example 11 from 2-[4-(2-methyl-4-phenyl-1H-imidazol-1-yl)phenyl]ethyl (4-methylphenyl)sulfonylcarbamate: MS (ESI) m/z 476 [M+H]$^+$, 474 [M–H]$^-$.

Example 32

4-CHLORO-N-{[(2-{4-[2-ETHYL-4-(1,3-THIAZOL-2-YL)-1H-IMIDAZOL-1-YL]PHENYL}ETHYL)AMINO]CARBONYL}BENZENESULFONAMIDE MONO-SODIUM SALT

STEP 1. tert-butyl 2-{4-[2-ethyl-4-(1,3-thiazol-2-yl)-1H-imidazol-1-yl]phenyl}ethylcarbamate The title compound was prepared according to the procedure described in step 4 of Example 26 from tert-butyl 2-[4-(propanimidoylamino)phenyl]ethylcarbamate and 1-(1,3-thiazol-2-yl)butan-1-one hydrobromide. (*Helv. Chim. Acta.*, 1948, 31, 1142). MS (ESI) m/z 399 [M+H]$^+$.

STEP 2. phenyl 2-{4-[2-ethyl-4-(1,3-thiazol-2-yl)-1H-imidazol-1-yl]phenyl}ethylcarbamate The title compound was prepared according to the procedure described in step 5 of Example 26 from tert-butyl 2-{4-[2-ethyl-4-(1,3-thiazol-2-yl)-1H-imidazol-1-yl]phenyl}ethylcarbamate. MS (ESI) m/z 419 [M+H]$^+$.

STEP 3. 4-chloro-N-{[(2-{4-[2-ethyl-4-(1,3-thiazol-2-yl)-1H-imidazol-1-yl]phenyl}ethyl)amino]carbonyl}benzenesulfonamide The title compound was prepared according to the procedure described in step 2 of Example 18 from phenyl 2-{4-[2-ethyl-4-(1,3-thiazol-2-yl)-1H-imidazol-1-yl]phenyl}ethylcarbamate and 4-chlorobenzenesulfonamide. MS (ESI) m/z 516 [M+H]$^+$, 514 [M–H]$^-$, $^1$H-NMR (CDCl$_3$) δ1.22 (3H, t, J=7.5 Hz), 2.69 (2H, q, J=7.5 Hz), 2.88 (2H, t, J=6.8 Hz), 3.49–3.56 (2H, m), 6.64 (1H, br), 7.21–7.30 (4H, m), 7.48 (2H, d, J=8.8 Hz), 7.58 (1H, s), 7.77 (2H, d, J=3.3 Hz), 7.80 (2H, d, J=8.8 Hz)

STEP 4. 4-chloro-N-{[(2-{4-[2-ethyl-4-(1,3-thiazol-2-yl)-1H-imidazol-1-yl]phenyl}ethyl)amino]carbonyl}benzenesulfonamide mono-sodium salt The title compound was prepared according to the procedure described in step 2 of Example 11 from 4-chloro-N-{[(2-{4-[2-ethyl-4-(1,3-thiazol-2-yl)-1H-imidazol-1-yl]phenyl}ethyl)amino]carbonyl}benzenesulfonamide: MS (ESI) m/z 516 [M+H]$^+$, 514 [M–H]$^-$.

Example 33

2-{4-[2-ETHYL-4-(4-METHYLPHENYL)-1H-IMIDAZOL-1-YL]PHENYL}ETHYL (2-CHLOROPHENYL)SULFONYLCARBAMATE MONO-SODIUM SALT

STEP 1. 2-{[4-(2-hydroxyethyl)phenyl]amino}-1-(4-methylphenyl)ethanone

The title compound was prepared according to the procedure described in step 1 of Example 3 from 2-bromo-1-(4-methylphenyl)ethanone. MS (EI) m/z 269 [M]$^+$.

STEP 2. 2-{4-[2-ethyl-4-(4-methylphenyl)-1H-imidazol-1-yl]phenyl}ethanol

The title compound was prepared according to the procedure described in step 1 of Example 10 from 2-{[4-(2-hydroxyethyl)phenyl]amino}-1-(4-methylphenyl)ethanone. MS (EI) m/z 306 [M]$^+$.

STEP 3. 2-{4-[2-ethyl-4-(4-methylphenyl)-1H-imidazol-1-yl]phenyl}ethyl (2-chlorophenyl)sulfonylcarbamate The title compound was prepared according to the procedure described in step 1 of Example 7 from 2-{4-[2-ethyl-4-(4-methylphenyl)-1H-imidazol-1-yl]phenyl}ethanol. MS (ESI) m/z 524 [M+H]$^+$, 522 [M−H]$^-$, $^1$H-NMR (DMSO-d$_6$) δ1.15 (3H, t, J=7.5 Hz), 2.29 (3H, s), 2.49 (3H, s), 2.65 (2H, q, J=7.5 Hz), 2.87 (2H, t, J=6.6 Hz), 4.19 (2H, t, J=6.4 Hz), 7.18 (2H, d, J=8.0 Hz), 7.34 (2H, d, J=8.8 Hz), 7.39 (2H, d, J=8.8 Hz), 7.50–7.55 (1H, m), 7.62–7.75 (5H, m), 8.02 (1H, d, J=7.5 Hz).

STEP 4. 2-{4-[2-ethyl-4-(4-methylphenyl)-1H-imidazol-1-yl]phenyl}ethyl (2-chlorophenyl)sulfonylcarbamate monosodium salt The title compound was prepared according to the procedure described in step 2 of Example 11 from 2-{4-[2-ethyl-4-(4-methylphenyl)-1H-imidazol-1-yl]phenyl}ethyl (2-chlorophenyl)sulfonylcarbamate: MS (ESI) m/z 524 [M+H]$^+$, 522 [M−H]$^-$.

Example 34

N-[({2-[4-(2-ETHYL-4,5,6,7-TETRAHYDRO-1H-BENZIMIDAZOL-1-YL)PHENYL]ETHYL}AMINO)CARBONYL]-4-METHYLBENZENESULFONAMIDE

STEP 1. 2-[4-(2-NITROANILINO)PHENYL]ETHANOL

A mixture of 2-chloronitrobenzene (3.9 g, 25 mmol) and 4-aminophenylethyl alcohol (4.1 g, 30 mmol) was placed in a sealed tube and heated at 150° C. for 3 h. The reaction mixture was cooled and purified by flash column chromatography on silica gel eluting with hexane/ethyl acetate (2:1) to afford 3.5 g (55%) of the title compound as orange solids: $^1$H-NMR (CDCl$_3$)δ2.90 (2H, t, J=6.5 Hz), 3.91 (2H, t, J=6.5 Hz), 6.81–6.70 (1H, m), 7.40–7.16 (6H, m), 8.21 (1H, dd, J=1.5, 8.8 Hz), 9.47 (1H, s).

STEP 2. 2-[4-(2-Aminoanilino)phenyl]ethanol

To a stirred solution of 2-[4-(2-nitroanilino)phenyl]ethanol (2.0 g, 7.6 mmol) in methanol (15 mL) was added 10% Pd—C (160 mg). The mixture was stirred at room temperature for 6 h under hydrogen atmosphere. The palladium catalyst was removed by filtration and washed with ethanol (100 mL). The filtrate was concentrated under reduced pressure to afford 1.6 g (92%) of the title compound as pale yellow solids: $^1$H-NMR (CDCl$_3$)δ2.79 (2H, t, J=6.6 Hz), 3.75 (2H, br), 3.80 (2H, t, J=6.6 Hz), 5.14 (1H, s), 6.82–6.66 (4H, m), 7.15–6.96 (4H, m).

STEP 3. 2-[4-(2-Ethyl-1H-benzimidazol-1-yl)phenyl]ethyl propionate

To a stirred suspension of 2-[4-(2-aminoanilino)phenyl]ethanol (1.6 g, 7 mmol) in toluene (70 mL) was added propionyl chloride (1.5 g, 16 mmol) dropwise at 0° C., and the reaction mixture was heated at reflux temperature for 2 h. After cooling, the mixture was poured into water (50 mL) and extracted with ethyl acetate (100 mL). The organic layer was washed with 2N aqueous NaOH (50 mL) and brine (50 mL), then dried (MgSO$_4$). Removal of solvent gave 1.3 g (58%) of the title compound as brown solids: MS (EI) m/z 322 (M$^+$)

STEP 4. 2-[4-(2-Ethyl-1H-benzimidazol-1-yl)phenyl]ethanol

To a solution of 2-[4-(2-ethyl-1H-benzimidazol-1-yl)phenyl]ethyl propionate (1.3 g, 4 mmol) in methanol/THF (v/v, 1:1, 32 mL) was added 4N aqueous LiOH (8 mL, 8 mmol) and the resulting mixture was stirred at room temperature. After 3 h, the mixture was concentrated. The residue was dissolved in water (30 mL) and extracted with ethyl acetate (100 mL). The organic layer was washed with brine (50 mL), dried (MgSO$_4$), and concentrated. Purification by flash column chromatography on silica gel eluting with hexane/ethyl acetate (gradient elution from 2:1 to 0:1) to afford 920 g (86%) of the title compound as pale brown solids: $^1$H-NMR (CDCl$_3$)δ1.26 (3H, t, J=7.5 Hz), 2.80 (2H, q, J=7.5 Hz), 3.00 (2H, t, J=6.5 Hz), 3.98 (2H, t, J=6.5 Hz), 7.25–7.08 (3H, m), 7.31 (2H, d, J=8.3 Hz), 7.45 (2H, d, J=8.3 Hz), 7.81–7.75 (1H, m).

STEP 5. 2-[4-(2-Ethyl-1H-benzimidazol-1-yl)phenyl]ethyl azide

A mixture of 2-[4-(2-ethyl-1H-benzimidazol-1-yl)phenyl]ethanol (914 mg, 3.4 mmol) in TUF (40 mL) was added diethyl azodicarboxylate (DEAD) (1.2 mg, 7 mmol), triphenylphosphine (1.8 g, 7 mmol) and diphenylphosphoryl azide (DPPA) (1.9 g, 7 mmol). The mixture was stirred at room temperature for 4.5 h. After removal of solvent, the residue was purified by flash column chromatography on silica gel eluting with hexane/ethyl acetate (gradient elution from 1:1 to 1:2) to afford 1000 mg (74%) of the title compound as a brown oil: MS (EI) m/z 291 (M$^+$)

STEP 6. 2-[4-(2-Ethyl-1H-benzimidazol-1-yl)phenyl]ethylamine

To a solution of 2-[4-(2-ethyl-1H-benzimidazol-1-yl)phenyl]ethyl azide (990 mg, 3.4 mmol) in methanol (20 mL) was added 10% Pd—C (100 mg). The resulting mixture was stirred for 4 h under hydrogen atmosphere. The mixture was filtered through a pad of Celite and the filtrate was concentrated. The residue was purified by flash column chromatography on silica gel eluting with dichloromethane/methanol/triethylamine (100:5:1) to afford 855 mg (94%) of the title compound as white solids: $^1$H-NMR (CDCl$_3$)δ1.26 (3H, t, J=7.5 Hz), 2.76 (2H, q, J=7.5 Hz), 2.89 (2H, t, J=6.5 Hz), 3.06 (2H, t, J=6.5 Hz), 7.45–7.06 (7H, m),7.80–7.74 (1H, m).

STEP 7. 2-Ethyl-1-(4-{2-[({[(4-methylphenyl)sulfonyl]amino}carbonyl)amino]ethyl}phenyl)-1H-benzimidazole The title compound was prepared according to the procedure described in step 3 of Example 3 from 2-[4-(2-Ethyl-1H-benzimidazol-1-yl)phenyl]ethylamine: $^1$H-NMR (CDCl$_3$)δ1.33 (3H, t, J=7.0 Hz), 2.41 (3H, s), 2.79 (2H, q, J=7.0 Hz), 2.94 (2H, t, J=6.3 Hz), 3.62–3.54 (2H, m), 6.68 (1H, br), 7.07 (1H, d, J=8.8 Hz), 7.39–7.14 (8H, m), 7.71 (2H, d, J=8.3 Hz), 7.75 (1H, d, J=8.8 Hz), STEP 8. N-[({2-[4-(2-ethyl-4,5,6,7-tetrahydro-1H-benzimidazol-1-yl)phenyl]ethyl}amino)carbonyl]-4-methylbenzenesulfonamide A mixture of 2-Ethyl-1-(4-{2-[({[(4-methylphenyl)sulfonyl]amino}carbonyl) amino]ethyl}phenyl)-1H-benzimidazole (100 mg, 0.20 mmol) and platinum (IV) oxide (22 mg, 0.096 mmol) in 2 M HCl (10 mL) and CH$_3$OH (2 mL) was stirred for 8 h under hydrogen atmosphere (3 kgf/cm$^2$). The mixture was filtered through a pad of Celite and the filtrate was concentrated. The crude product was purified by TLC with ethyl acetate/ethanol (10:1) to afford 18 mg (14%) of the title compound as colorless solid: MS (ESI) m/z 467 [M+H]$^+$, 465 [M–H]$^-$, $^1$H-NMR (CDCl$_3$) δ1.15 (3H, t, J=7.6 Hz), 1.78 (2H, br), 2.26 (2H, br), 2.41 (3H, s), 2.55 (2H, q, J=7.6 Hz), 2.65 (2H, br), 2.83 (2H, br), 2.86 (2H, m), 3.49 (2H, m), 6.71 (1H, br), 7.10 (2H, d, J=8.4 Hz), 7.28 (4H, m), 7.79 (2H, d, J=8.2 Hz).

Example 35

N-[({2-[4-(4-TERT-BUTYL-2-ETHYL-1H-IMIDAZOL-1-YL)PHENYL]ETHYL}AMINO) CARBONYL]-4-CHLOROBENZENESULFONAMIDE MONO-SODIUM SALT

STEP 1. tert-butyl 2-[4-(4-tert-butyl-2-ethyl-1H-imidazol-1-yl)phenyl]ethylcarbamate The title compound was prepared according to the procedure described in step 4 of Example 26 from tert-butyl 2-[4-(propanimidoylamino)phenyl]ethylcarbamate and 1-bromo-3,3-dimethylbutan-2-one: MS (ESI) m/z 372 [M+H]$^+$.

STEP 2. phenyl 2-[4-(4-tert-butyl-2-ethyl-1H-imidazol-1-yl)phenyl]ethylcarbamate The title compound was prepared according to the procedure described in step 5 of Example 26 from tert-butyl 2-[4-(4-tert-butyl-2-ethyl-1H-imidazol-1-yl)phenyl] ethylcarbamate. MS (ESI) m/z 392[M+H]$^+$.

STEP 3. N-[({2-[4-(4-tert-butyl-2-ethyl-1H-imidazol-1-yl) phenyl]ethyl}amino)carbonyl]-4-chlorobenzenesulfonamide The title compound was prepared according to the procedure described in step 2 of Example 18 from phenyl 2-[4-(4-tert-butyl-2-ethyl-1H-imidazol-1-yl)phenyl] ethylcarbamate and 4-chlorobenzenesulfonamide. MS (ESI) m/z 489 [M+H]$^+$, 487 [M–H]$^-$, $^1$H-NMR (CDCl$_3$)δ1.12 (3H, t, J=7.5 Hz), 1.31 (9H, s), 2.62 (2H, q, J=7.5 Hz), 2.84 (2H, t, J=7.0 Hz), 3.45–3.54 (2H, m), 6.48 (1H, br),6.65 (1H, s), 7.17 (2H, d, J=8.5 Hz), 7.24 (2H, d, J=8.5 Hz), 7.43 (2H, d, J=8.4 Hz), 7.82 (2H, d, J=8.8 Hz).

STEP 4. N-[({2-[4-(4-tert-butyl-2-ethyl-1H-imidazol-1-yl) phenyl]ethyl}amino)carbonyl]-4-chlorobenzenesulfonamide mono-sodium salt The title compound was prepared according to the procedure described in step 2 of Example 11 from N-[({2-[4-(4-tert-butyl-2-ethyl-1H-imidazol-1-yl)phenyl] ethyl}amino)carbonyl]-4-chlorobenzenesulfonamide: MS (ESI) m/z 489 [M+H]$^+$, 487 [M–H]$^-$.

Example 36

2-CHLORO-N-{[(2-{4-[4-(4-CYANOPHENYL)-2-ETHYL-1H-IMIDAZOL-1-YL]PHENYL}ETHYL) AMINO] CARBONYL}BENZENESULFONAMIDE MONO-SODIUM SALT

STEP 1. tert-butyl 2-{4-[4-(4-cyanophenyl)-2-ethyl-1H-imidazol-1-yl]phenyl}ethylcarbamate The title compound was prepared according to the procedure described in step 4 of Example 26 from tert-butyl 2-[4-(propanimidoylamino)phenyl]ethylcarbamate and 4-(bromoacetyl)benzonitrile: MS (ESI) m/z 417 [M+H]$^+$.

STEP 2. phenyl 2-{4-[4-(4-cyanophenyl)-2-ethyl-1H-imidazol-1-yl]phenyl}ethylcarbamate The title compound was prepared according to the procedure described in step 5 of Example 26 from tert-butyl 2-{4-[4-(4-cyanophenyl)-2-ethyl-1H-imidazol-1-yl] phenyl}ethylcarbamate. MS (ESI) m/z 437 [M+H]$^+$.

STEP 3. 2-chloro-N-{([2-{4-[4-(4-cyanophenyl)-2-ethyl-1H-imidazol-1-yl]phenyl}ethyl)amino]carbonyl}benzenesulfonamide The title compound was prepared according to the procedure described in step 2 of Example 18 from phenyl 2-{4-[4-(4-cyanophenyl)-2-ethyl-1H-imidazol-1-yl] phenyl}ethylcarbamate and 2-chlorobenzenesulfonamide. MS (ESI) m/z 534 [M+H]$^+$, 532 [M–H]$^-$, $^1$H-NMR (CDCl$_3$) δ1.26 (3H, t, J=7.5 Hz), 2.70 (2H, q, J=7.7 Hz), 2.86 (2H, t, J=7.1 Hz), 3.47–3.55 (2H, m), 6.58 (1H, br), 7.23–7.31 (3H, m), 7.36 (1H, s), 7.41–7.47 (1H, m), 7.57–7.66 (4H, m), 7.89 (2H, d, J=8.6 Hz),8.01 (1H, d, J=8.4 Hz)

STEP 4. 2-chloro-N-{[(2-{4-[4-(4-cyanophenyl)-2-ethyl-1H-imidazol-1-yl]phenyl}ethyl)amino]carbonyl}benzenesulfonamide mono-sodium salt The title compound was prepared according to the procedure described in step 2 of Example 11 from 2-chloro-N-{[(2-{4-[4-(4-cyanophenyl)-2-ethyl-1H-imidazol-1-yl] phenyl}ethyl)amino]carbonyl}benzenesulfonamide: MS (ESI) m/z 534 [M+H]$^+$, 532 [M–H]$^-$.

Example 37

2-{4-[2-AMINO-5-(4-FLUOROPHENYL)-4-METHYL-1H-IMIDAZOL-1-YL] PHENYL}ETHYL (4-METHYLPHENYL) SULFONYLCARBAMATE

STEP. 1 1-(4-fluorophenyl)-1-1-{[4-(2-hydroxyethyl) phenyl]amino}acetone

The title compound was prepared according to the procedure described in step 1 of Example 3 from 1-bromo-1-(4-fluorophenyl)acetone: MS (ESI) m/z MS (ESI) m/z 288 [M+H]$^+$, 286 [M–H]$^-$, $^1$H-NMR (CDCl$_3$)δ2.12 (3H, s), 2.69 (2H, t, J=6.9 Hz), 3.74 (2H, q, J=6.2 Hz), 4.96 (1H, d, J=3.9 Hz), 5.34(1H, br), 6.49 (2H, d. J=8.4 Hz), 6.96 (2H, d, J=8.4 Hz), 7.04–7.10 (2H, m), 7.40–7.45(2H, m).

STEP 2. 2-{4-[2-amino-5-(4-fluorophenyl)-4-methyl-1H-imidazol-1-yl]phenyl}ethanol The title compound was prepared according to the procedure described in step 2 of Example 3 from 1-(4-fluorophenyl)-1-{[4-(2-hydroxyethyl)phenyl] amino}acetone: MS (ESI) m/z 312 [M+H]$^+$.

STEP 3. 2-{4-[2-amino-5-(4-fluorophenyl)-4-methyl-1H-imidazol-1-yl]phenyl}ethyl (4-methylphenyl) sulfonylcarbamate The title compound was prepared according to the procedure described in step 3 of Example 3 from 2-{4-[2-amino-5-(4-fluorophenyl)-4-methyl-1H-imidazol-1-yl] phenyl}ethanol: MS (ESI) m/z 509 [M+H]$^+$, 507 [M–H]$^-$, $^1$H-NMR (CDCl$_3$)δ2.20 (3H, s), 2.87 (2H, t, J=6.3 Hz), 3.48 (3H, s), 3.89 (2H, t, J=6.4 Hz), 6.86–7.06 (8H, m), 7.27 (4H, m).

Example 39

3-CHLORO-N-[({2-[4-(2-ETHYL-4-PHENYL-1H-IMIDAZOL-1-YL)PHENYL]ETHYL}AMINO) CARBONYL]BENZENESULFONAMIDE MONO-SODIUM SALT

STEP 1. 3-chloro-N-[({2-[4-(2-ethyl-4-phenyl-1H-imidazol-1-yl)phenyl]ethyl}amino)carbonyl] benzenesulfonamide The title compound was prepared according to the procedure described in step 2 of Example 18 from 2-[4-(2-ethyl-4-phenyl-1H-imidazol-1-yl)phenyl]ethylcarbamate and 3-chlorobenzenesulfonamide. MS (ESI) m/z 509

[M+H]+, 507 [M−H]−, 1H-NMR (CDCl3) δ1.22 (3H, t, J=7.5 Hz), 2.68 (2H, q, J=7.5 Hz), 2.86 (2H, t, J=6.6 Hz), 3.47–3.56 (2H, m), 6.44 (1H, br), 7.23–7.28 (5H, m), 7.36 (2H, t, J=7.3 Hz), 7.45 (2H, t, J=8.1 Hz), 7.58 (2H, d, J=8.1 Hz), 7.73–7.78 (2H, m), 7.87 (1H, m).

STEP 2. 3-chloro-N-[({2-[4-(2-ethyl-4-phenyl-1H-imidazol-1-yl)phenyl]ethyl}amino)carbonyl]benzenesulfonamide mono-sodium salt The title compound was prepared according to the procedure described in step 2 of Example 11 from 3-chloro-N-[({2-[4-(2-ethyl-4-phenyl-1H-imidazol-1-yl)phenyl]ethyl}amino)carbonyl]benzenesulfonamide: MS (ESI) m/z 509 [M+H]+, 507 [M−H]−.

Example 40

4-CHLORO-N-{[(2-{4-[4-(4-CYANOPHENYL)-2-ETHYL-1H-IMIDAZOL-1-YL]PHENYL}ETHYL)AMINO]CARBONYL}BENZENESULFONAMIDE MONO-SODIUM SALT

STEP 1. 4-chloro-N-{[(2-{4-[4-(4-cyanophenyl)-2-ethyl-1H-imidazol-1-yl]phenyl}ethyl)amino]carbonyl}benzenesulfonamide The title compound was prepared according to the procedure described in step 2 of Example 18 from phenyl 2-{4-[4-(4-cyanophenyl)-2-ethyl-1H-imidazol-1-yl]phenyl}ethylcarbamate and 4-chlorobenzenesulfonamide. MS (ESI) m/z 534 [M+H]+, 532 [M−H]−, 1H-NMR (CDCl3) δ1.26 (3H, t, J=7.5 Hz), 2.70 (2H, q, J=7.7 Hz), 2.92 (2H, t, J=7.1 Hz), 3.47–3.55 (2H, m), 6.61 (1H, br), 7.27–7.37 (4H, m), 7.50 (2H, d, J=8.8 Hz), 7.64 (2H, d, J=8.6 Hz), 7.77 (2H, d, J=8.6 Hz), 7.89 (2H, d, J=8.6 Hz).

STEP 2. 4-chloro-N-{[(2-{4-[4-(4-cyanophenyl)-2-ethyl-1H-imidazol-1-yl]phenyl}ethyl)amino]carbonyl}benzenesulfonamide mono-sodium salt The title compound was prepared according to the procedure described in step 2 of Example 11 from 4-chloro-N-{[(2-{4-[4-(4-cyanophenyl)-2-ethyl-1H-imidazol-1-yl]phenyl}ethyl)amino]carbonyl}benzenesulfonamide: MS (ESI) m/z 534 [M+H]+, 532 [M−H]−.

Example 41

4-CHLORO-N-{[(2-{4-[2-ETHYL-4-(6-METHYLPYRIDIN-2-YL)-1H-IMIDAZOL-1-YL]PHENYL}ETHYL)AMINO]CARBONYL}BENZENESULFONAMIDE MONO-SODIUM SALT

STEP 1. tert-butyl 2-{4-[2-ethyl-4-(6-methylpyridin-2-yl)-1H-imidazol-1-yl]phenyl}ethylcarbamate The title compound was prepared according to the procedure described in step 4 of Example 26 from tert-butyl 2-[4-(propanimidoylamino)phenyl]ethylcarbamate and 2-bromo-1-(6-methylpyridin-2-yl)ethanone hydrobromide (*J. Med. Pharm. Chem.*, 1961, 3, 561). MS (ESI) m/z 407 [M+H]+.

STEP 2 4-chloro-N-{[(2-{4-[2-ethyl-4-(6-methylpyridin-2-yl)-1H-imidazol-1-yl]phenyl}ethyl)amino]carbonyl}benzenesulfonamide The title compound was prepared according to the procedure described in step 5 of Example 26 from tert-butyl 2-{4-[2-ethyl-4-(6-methylpyridin-2-yl)-1H-imidazol-1-yl]phenyl}ethylcarbamate and 4-chlorobenzenesulfonyl isocyanate. MS (ESI) m/z 524 [M+H]+, 522 [M−H]−, 1H-NMR (DMSO d-6) δ1.20 (3H, t, J=7.3 Hz), 2.49 (3H, s), 2.67 (2H, q, J=7.5 Hz), 2.78 (2H, t, J=7.1 Hz), 3.25–3.32 (2H, m), 6.66 (1H, t, J=5.5 Hz), 7.10 (2H, 1, J=6.4 Hz), 7.33 (2H, d, J=8.4 Hz), 7.42 (2H, d, J=8.4 Hz), 7.7–7.76 (4H, m), 7.93 (1H, d, J=8.6 Hz).

STEP 3. 4-chloro-N-{[(2-{4-[2-ethyl-4-(6-methylpyridin-2-yl)-1H-imidazol-1-yl]phenyl}ethyl)amino]carbonyl}benzenesulfonamide mono-sodium salt The title compound was prepared according to the procedure described in step 2 of Example 11 from 4-chloro-N-{[(2-{4-[2-ethyl-4-(6-methylpyridin-2-yl)-1 H-imidazol-1-yl]phenyl}ethyl)amino]carbonyl}benzenesulfonamide: MS (ESI) m/z 524 [M+H]+, 522 [M−H]−

What is claimed is:

1. A compound of the following formula (I):

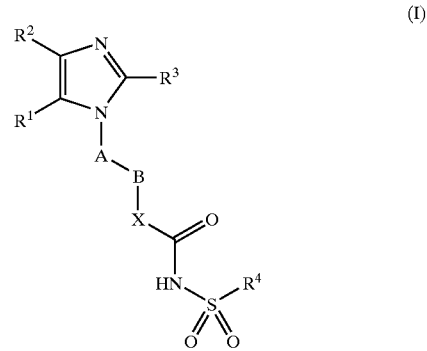

wherein:
either $R^1$ represents a hydrogen atom, an alkyl group having from 1 to 6 carbon atoms, an aryl group or a heteroaryl group; and $R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group; or $R^1$ and $R^2$ groups are joined together to form an alkylene chain having 3 to 6 carbon atoms;

$R^3$ represents a hydrogen atom, a halogen atom, an alkyl group having from 1 to 6 carbon atoms, an amino group, mono- or di-alkylamino groups, with alkyl group(s) having from 1 to 6 carbon atoms, a haloalkyl group having from 1 to 6 carbon atoms, a cycloalkyl group having from 3 to 8 carbon atoms, a cycloalkenyl group having from 3 to 10 carbon atoms, an aralkyl group, an aryl group or a heteroaryl group;

$R^4$ represents an aryl group, or a heteroaryl group;

A represents an aryl[1] group having from 6 to 10 carbon atoms or an heteroaryl[1] group having from 5 to 7 atoms, wherein 1 to 4 of said atoms of the heteroaryl[1] group are independently selected from the group consisting of sulfur atoms, oxygen atoms and nitrogen atoms;

B represents an alkylene group having from 1 to 6 carbon atoms;

X represents NH, N[($C_1$–$C_6$)alkyl], oxygen or sulfur;

said aryl groups have from 6 to 14 carbon atoms;

said heteroaryl groups are 5- to 14-membered aromatic heterocyclic groups containing from 1 to 4 heteroatoms selected from the group consisting of sulfur atoms, oxygen atoms and nitrogen atoms;

said aryl groups and said heteroaryl groups are unsubstituted or are substituted by at least one substituent selected from the group consisting of substituents α, defined below;

said aralkyl groups are alkyl groups having from 1 to 6 carbon atoms and which are substituted by at least one aryl group as defined above;

said substituents α are selected from the group consisting of alkyl group having from 1 to 6 carbon atoms, an aryl group defined above, a heteroaryl group defined above, hydroxy groups, halogen atom, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, with alkyl group(s) having from 1 to 6 carbon atoms in the alkyl and alkoxy part, alkylsulfonylamino group having from 1 to 6 carbon atoms and aminosulfonyl group;

with the proviso that said aryl groups and said heteroaryl groups in said substituents α are not substituted by an aryl group or an heteroaryl group: or a pharmaceutically acceptable ester of such compound, or a pharmaceutically acceptable salt thereof.

2. A compound according to claim 1, wherein
$R^1$ represents a hydrogen atom, an alkyl group having from 1 to 6 carbon atoms or an unsubstituted aryl group having from 6 to 10 carbon atoms.

3. A compound according to claim 1, wherein
$R^2$ represents a hydrogen atom, a halogen atom, an alkyl group having from 1 to 6 carbon atoms, a cycloalkyl group having from 3 to 8 carbon atoms, an aralkyl group, an aryl group or a heteroaryl group.

4. A compound according to claim 1, wherein
$R^2$ represents a hydrogen atom, an alkyl group having from 1 to 6 carbon atoms, a cycloalkyl group having from 3 to 8 carbon atoms, an aryl group having from 6 to 10 carbon atoms or a heteroaryl group having from 5 to 7 atoms, wherein 1 to 4 of said atoms are independently selected from the group consisting of sulfur atoms, oxygen atoms and nitrogen atoms;

said aryl groups and said heteroaryl groups are unsubstituted or are substituted by at least one substituent selected from the group consisting of substituents α, defined below;

said substituents α are selected from the group consisting of alkyl groups having from 1 to 6 carbon atoms, hydroxy groups, halogen atoms, alkoxy groups having from 1 to 6 carbon atoms, alkanoylamino groups having from 1 to 6 carbon atoms, di-alkylamino group, with alkyl group(s) having from 1 to 6 carbon atoms, haloalkyl groups having from 1 to 6 carbon atoms and carbamoyl groups.

5. A compound according to claim 1, wherein
$R^3$ represents a hydrogen atom, an alkyl group having from 1 to 6 carbon atoms, an amino group, a haloalkyl group having from 1 to 6 carbon atoms, or an aryl group having from 6 to 10 carbon atoms.

6. A compound according to claim 1, wherein
$R^4$ represents an aryl or a heteroaryl group;
said aryl group and said heteroaryl group are unsubstituted or are substituted by at least one substituent selected from the group consisting of substituents α, defined below;

said substituents α are selected from the group consisting of alkyl groups having from 1 to 6 carbon atoms, hydroxy groups, halogen atoms, alkoxy groups having from 1 to 6 carbon atoms, haloalkoxy groups having from 1 to 6 carbon atoms, alkanoyl groups having from 1 to 6 carbon atoms, alkanoylaminoalkyl groups having from 1 to 6 carbon atoms in the alkanoyl and alkyl part, haloalkyl groups having from 1 to 6 carbon atoms, carbamoyl groups, cyano groups and aminosulfonyl groups.

7. A compound according to claim 1, wherein
$R^4$ represents a aryl group having from 6 to 10 carbon atoms, or a heteroaryl group having from 5 to 7 atoms, wherein 1 to 4 of said atoms are independently selected from the group consisting of sulfur atoms, oxygen atoms and nitrogen atoms;

said aryl groups and said heteroaryl groups are unsubstituted or are substituted by at least one substituent selected from the group consisting of substituents α, defined below; and said substituents a are selected from the group consisting of alkyl groups having from 1 to 6 carbon atoms, hydroxy groups, halogen atoms, alkoxy groups having from 1 to 6 carbon atoms, alkanoyl groups having from 1 to 6 carbon atoms, haloalkyl groups having from 1 to 6 carbon atoms, carbamoyl groups, cyano groups and aminosulfonyl groups.

8. A compound according to claim 1, wherein
A represents a phenylene or pyridylene.

9. A compound according to claim 1, wherein
X represents NH, oxygen or sulfur.

10. A compound according to claim 1 selected from

2-[4-(4-phenyl-1H-imidazole-1-yl)phenyl]ethyl (4-methylphenyl)sulfonylcarbamate;

2-[4-(2-amino-4,5-diphenyl-1H-imidazol-1-yl)phenyl] ethyl (4-methylphenyl) sulfonylcarbamate;

2-[4-(2-ethyl-4-phenyl-1Himidazole-1-yl)phenyl]ethyl (4-methylphenyl) sulfonylcarbamate;

N-[({2-[4-(2-ethyl-4-phenyl-1H-imidazol-1-yl)phenyl] ethyl}amino)carbonyl]-4-methylbenzenesulfonamide;

2-chloro-N-[({2-[4-(2-ethyl-4-phenyl-1H-imidazol-1-yl) phenyl]ethyl}amino) carbonyl]benzenesulfonamide;

2-[4-(2,4-diphenyl-1H-imidazol-1-yl)phenyl]ethyl (4-methylphenyl)sulfonylcarbamate;

2-[4-(2-butyl-4-phenyl-1H-imidazol-1-yl)phenyl]ethyl (2-chlorophenyl) sulfonylcarbamate;

2-[4-(2-isobutyl-4-phenyl-1H-imidazol-1-yl)phenyl]ethyl (2-chlorophenyl) sulfonylcarbamate;

2-[4-(2-isopropyl-4-phenyl-1H-imidazol-1-yl)phenyl] ethyl (2-chlorophenyl) sulfonylcarbamate;

N-[({2-[4-(2-ethyl-4-phenyl-1H-imidazol-1-yl)phenyl] ethyl}amino)carbonyl]-5-methyl-2-pyridinesulfonamide;

4-chloro-N-[({2-[4-(2-ethyl-4-phenyl-1H-imidazol-1-yl) phenyl]ethyl}amino)carbonyl]benzenesulfonamide;

4-fluoro-N-[({2-[4-(2-ethyl-4-phenyl-1H-imidazol-1-yl) phenyl]ethyl}amino) carbonyl]benzenesulfonamide;

2-[4-(2-tert-butyl-4-phenyl-1H-imidazol-1-yl)phenyl] ethyl (2-chlorophenyl) sulfonylcarbamate; and 4-chloro-N-[({2-[4-(2-isopropyl-4-phenyl-1H-imidazol-1-yl)phenyl]ethyl}amino) carbonyl] benzenesulfonamide or an ester of such compound, and salts thereof.

11. A compound according to claim 1 selected from

2-[4-(2-amino-4,5-diphenyl-1H-imidazol-1-yl)phenyl]ethyl (4-methylphenyl) sulfonylcarbamate;

2-[4-(2-ethyl-4-phenyl-1H-imidazole-1-yl)phenyl]ethyl (4-methylphenyl) sulfonylcarbamate;

N-[({2-[4-(2-ethyl-4-phenyl-1H-imidazol-1-yl)phenyl]ethyl}amino)carbonyl]-4-methylbenzenesulfonamide;

2-chloro-N-[({2-[4-(2-ethyl-4-phenyl-1H-imidazol-1-yl)phenyl]ethyl}amino) carbonyl]benzenesulfonamide;

2-[4-(2-butyl -4-phenyl-1H-imidazol-1-yl)phenyl]ethyl (2-chlorophenyl) sulfonylcarbamate;

2-[4-(2-isobutyl-4-phenyl-1H-imidazol-1-yl)phenyl]ethyl (2-chlorophenyl) sulfonylcarbamate;

2-[4-(2-isopropyl-4-phenyl-1H-imidazol-1-yl)phenyl]ethyl (2-chlorophenyl) sulfonylcarbamate;

4-chloro-N-[({2-[4-(2-ethyl-4-phenyl-1H-imidazol-1-yl)phenyl]ethyl}amino)carbonyl]benzenesulfonamide;

N-[({2-[4-(2-ethyl-4-phenyl-1H-imidazol-1-yl)phenyl]ethyl}amino)carbonyl]-4-methoxybenzenesulfonamide; and 2-[4-(2-tert-butyl-4-phenyl-1H-imidazol-1-yl)phenyl]ethyl (2-chlorophenyl) sulfonylcarbamate;

or an ester of such compound, and salts thereof.

12. A pharmaceutical composition comprising a therapeutically effective amount of a compound according to claim 1, and a suitable pharmaceutically acceptable diluent or carrier.

13. A pharmaceutical composition for the treatment of a disorder or condition in a mammal, selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; allergic rhinitis, atopic dermatitis, asthma or eosinophil related disorders, Alzheimer's disease, sleep disorders, bone loss; osteoporosis; promotion of bone formation; kidney disease; and presurgery, which comprises a therapeutically effective amount of a compound according to claim 1, and a suitable pharmaceutically acceptable diluent or carrier.

14. A method of treating a disorder selected from pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; allergic rhinitis, atopic dermatitis, asthma or eosinophil related disorders, Alzheimer's disease, sleep disorders, bone loss; osteoporosis; promotion of bone formation; kidney disease; and presurgery; comprising administering to a mammal in need of such treatment a therapeutically effective amount of a compound of claim 1.

* * * * *